United States Patent
Borromeo et al.

(10) Patent No.: US 6,939,946 B2
(45) Date of Patent: Sep. 6, 2005

(54) RING MODIFIED CYCLIC PEPTIDE ANALOGS

(75) Inventors: Peter Stanley Borromeo, Fishers, IN (US); Jeffrey Daniel Cohen, Indianapolis, IN (US); George Stuart Gregory, Fishers, IN (US); Stacy Kay Henle, Indianapolis, IN (US); Stephen Andrew Hitchcock, Carmel, IN (US); Louis Nickolaus Jungheim, Indianapolis, IN (US); Daniel Ray Mayhugh, Carmel, IN (US); Timothy Alan Shepherd, Indianapolis, IN (US); William Wilson Turner, Jr., Bloomington, IN (US)

(73) Assignee: Eli Lilly and Company, Indianapolis, IN (US)

( * ) Notice: Subject to any disclaimer, the term of this patent is extended or adjusted under 35 U.S.C. 154(b) by 17 days.

(21) Appl. No.: 10/676,575

(22) Filed: Sep. 30, 2003

(65) Prior Publication Data

US 2004/0068094 A1 Apr. 8, 2004

Related U.S. Application Data

(63) Continuation of application No. 09/763,114, filed as application No. PCT/US99/18908 on Aug. 18, 1999, now Pat. No. 6,653,281.
(60) Provisional application No. 60/097,228, filed on Aug. 20, 1998.

(51) Int. Cl.[7] .................................................. C07K 7/50
(52) U.S. Cl. ...................... 530/317; 530/338; 530/339; 530/343
(58) Field of Search ...................... 514/9, 11; 530/317, 530/323, 337, 338, 339, 343

(56) References Cited

U.S. PATENT DOCUMENTS

| | | | | |
|---|---|---|---|---|
| 4,293,489 | A | 10/1981 | Debono | 530/317 |
| 4,320,052 | A | 3/1982 | Abbott et al. | 530/317 |
| 5,166,135 | A | 11/1992 | Schmatz | 514/11 |
| 5,541,160 | A | 7/1996 | Balkovec et al. | 514/11 |
| 5,696,084 | A | 12/1997 | Lartey et al. | 514/9 |
| 5,932,543 | A | 8/1999 | Burkhardt et al. | 514/11 |
| 5,965,525 | A | 10/1999 | Burkhardt et al. | 514/11 |
| 6,653,281 | B1 * | 11/2003 | Borromeo et al. | 514/11 |

FOREIGN PATENT DOCUMENTS

| | | |
|---|---|---|
| EP | 0 359 529 | 3/1990 |
| EP | 0 447 186 | 9/1991 |
| EP | 0 448 343 | 9/1991 |
| EP | 0 448 353 | 9/1991 |
| EP | 0 448 354 | 9/1991 |
| EP | 0 448 355 | 9/1991 |
| EP | 0 462 531 | 12/1991 |
| EP | 0 503 960 | 9/1992 |
| EP | 0 525 889 | 2/1993 |
| EP | 0 561 639 | 9/1993 |
| GB | 2241956 | 9/1991 |
| GB | 2242194 | 9/1991 |
| WO | WO 96/31228 | 10/1996 |
| WO | WO 96/37509 | 11/1996 |
| WO | WO 96/37510 | 11/1996 |
| WO | WO 96/37511 | 11/1996 |
| WO | WO 96/37512 | 11/1996 |
| WO | WO 97/05163 | 2/1997 |
| WO | WO 97/27864 | 8/1997 |
| WO | WO 99/06062 | 2/1999 |
| WO | WO 99/43337 | 9/1999 |
| WO | WO 00/11023 | 3/2000 |
| WO | WO 00/12540 | 3/2000 |
| WO | WO 00/35944 | 6/2000 |
| WO | WO 00/35945 | 6/2000 |

OTHER PUBLICATIONS

U.S. Appl. No. 07/992,390, filed Dec. 16, 1992, Burkhardt et al.

U.S. Appl. No. 08/032,228, filed Mar. 17, 1993, Burkhardt et al.

Baba, N., et al. (1989). "Intramolecular Asymmetric Lactonization Using Optically Active 1,2–Diphenylethylenediamine as a Chiral Auxiliary," *Chemistry Letters* 5: 889–892.

Baldwin, J.E. and Finn, A., (1987). "Use of L–Aspartic Acid β–Semialdehyde in the Synthesis of More Complex Non–Protein Amino Acids," *Tetrahedron Letters* 28(31): 3605–3608.

Curphey, et al. (1979). "Trifluoroacetylation of Amino Acids and Peptides by Ethyl Trifluoroacetate," *J. Org. Chem.* 44(15): 2805–2807.

Evans, D.A., and Weber, A.E., (1987). "Synthesis of Cyclic Hexapeptide Echinocandin D. New Approaches to the Asymmetric Synthesis of β–Hydroxy α–Amino Acids," *J. Am. Chem. Soc.* 109: 7151–7157.

Hensens, D.O. et al. (1992) "Pneumocandins from Zalerion arboricola" *Journal of Antibiotics* 45(12):1875–1885.

(Continued)

*Primary Examiner*—Jeffrey Edwin Russel
(74) *Attorney, Agent, or Firm*—Morrison & Foerster LLP

(57) ABSTRACT

A method for modifying the cyclic peptide ring system of Echinocandin-type compounds to produce new analogs having antifungal activity is provided. The inventive process comprises opening the cyclic peptide ring, cleaving the terminal ornithine unit, inserting at least one new amino acid or other synthetic unit and closing the ring to produce a new cyclic peptide ring structure. The process allows one to incorporate features such as water-solubility into the cyclic peptide ring nucleus, sites for further modification, increase or decrease the number of amino acid or peptide units within the ring nucleus, and increase or decrease the total number of members within the ring. The invention further provides novel Echinocandin type compounds and their use as antifungal or anti-parasitic agents.

18 Claims, No Drawings

OTHER PUBLICATIONS

Jamison, J.A. et al. (1998) "The synthesis and antifungal activity of nitrogen containing hemiaminal ethers of LY303366" *Journal of Antibiotics* 51(2):239–242.

Kurokawa, N. and Ohfune, Y., (1986). "Total Synthesis of Echinocandins 1. Stereocontrolled Synthesis of the Constituent Amino Acids," *J. Am. Chem. Soc* 108: 6041–6043.

Kurokawa, N. and Ohfune, Y., (1993). "Synthetic Studies on Antifungal Cyclic Peptides Echinocandins. Stereoselective Total Synthesis of Echinocandin D via a Novel Peptide Coupling," *Tetrahedron* 49(28): 6195–6222.

Sasaki, N.A., et al. (1987). "A Novel Approach to the Synthesis of Optically Pure Non Protein αAmino Acids in Both L and D Configuration from L–Serine," *Tetrahedron Letters* 28(48): 6069–6072.

Tanaka, K., et al. (1985). "Asymmetric Synthesis of γ–Alkyl–α–Methylene–γ–Butyrolactone Via 1,6–Remore Induciton Using 2-[Tributylstannyl)Methyl]Propenamides," *Tetrahedron Letters* 26(10): 1337–1340.

Turner, W.W. and Rodriguez, M.J. (1996). "Recent Advances in the Medicinal Chemistry of Antifungal Agents," *Current Pharmaceutical Design* 2: 209–224.

Yamamoto, Y., et al. (1991). "Asymmetric Synthesis of 5– and 6–Membered Lactones from Cyclic Substrates Bearing a $C_2$–Chiral Auxiliary," *J. Org Chem* 56(3): 1112–1119.

Yoda, H., et al. (1989). "New Synthetic Method of γ– and δ– Lactones via Successive Alkylation and Reduction of Cyclic Imides," *Chemistry Express* 4(8): 515–518.

Zambias, R.A. et al., (1992). "Preparation and Structure–Activity Relationships of Simplified Analogues of Antifungal Agent Cilofungin: A Total Synthesis Approach," *J. Med. Chem.* 35: 2843–2855.

* cited by examiner

RING MODIFIED CYCLIC PEPTIDE ANALOGS

CROSS-REFERENCE TO RELATED APPLICATIONS

This application is a continuation of U.S. application Ser. No. 09/763,114, now U.S. Pat. No. 6,653,281 B1, filed May 24, 2001, which is a U.S. National Phase filing of PCT Application No. PCT/US99/18908, filed Aug. 18, 1999, which claims the benefit of U.S. Provisional Application No. 60/097,228, filed Aug. 20, 1998, the contents of all of which are incorporated herein by reference in their entireties.

TECHNICAL FIELD

The present invention relates to the preparation of ring modified cyclic peptide analogs by replacing peptide unit(s) in the cyclic peptide ring nucleus of natural products or semi-synthetic derivatives thereof, in particular, Echinocandin-type compounds, and novel semi-synthetic cyclic peptide compounds produced therefrom.

BACKGROUND ART

Echinocandin B is a natural product with antifungal activity that has been modified in the past in a variety of ways. For example, simple derivatives have been made including dihydro- and tetrahydro-reduction products and modification of active groups pendant from the ring nucleus. The most common approach has been replacement of the N-acyl side chain. For example, U.S. Pat. Nos. 4,293,489; 4,320,052; 5,166,135; and 5,541,160; and EP 359529; 448353; 447186; 462531; and 561639 describe a variety of N-acyl derivatized Echinocandin-type compounds that provide varying degrees of antifungal and antiprotozoal activities.

Other modifications have included acylation of the hydroxyl group of the pendant phenolic group. For example, GB 2,242,194; and EP 448343; 448354; 503960 and 525889 describe the introduction of acyl, phosphono and sulfo radicals having a charged group at neutral pH to impart water solubility.

GB 2,241,956 and EP 448355 describe hydrogen-reduction products of cyclohexapeptide compounds.

A review of the Echinocandin families and their semi-synthetic analogs may be found in Turner, W., et al, *Current Pharmaceutical Design*, 2, 209–224 (1996). The review compares the in vitro and in vivo activities of the Echinocandin natural products and their semi-synthetic analogs.

Each of the approaches described above are limited to reactions with active groups pendant to the cyclic peptide ring nucleus. Some have attempted to build the entire cyclic peptide nucleus synthetically. (See, i.e., U.S. Pat. No. 5,696,084; *J. Am. Chem. Soc.*, 108, 6041 (1986); Evans, D. A., et al., *J. Am. Chem. Soc.*, 109, 5151 (1987); *J. Med. Chem.*, 35, 2843 (1992); and Kurokawa, N., et al., *Tetrahedron*, 49, 6195 (1993).) However, this approach is not cost effective and may lead to racemic mixtures. Therefore, there is a need to provide a more flexible and cost effective process for modifying the cyclic hexapeptide nucleus of natural products to broaden the scope of potential antifungal candidates.

Several investigators have disclosed the preferential cleavage of an amide bond in compounds bearing hydroxyl groups in the delta and gamma positions relative to the amide bond to provide asymmetric lactones using acids such as hydrochloric acid and trifluoroacetic acid; however, none have applied the process to the cleavage of a terminal amino acid group of a linear peptide. (See, i.e., K. Tanaka, et al., *Tetrahedron Lett*, 26(10), 1337 (1985); N. Baba, et al., *Chem Lett* (5), 889 (1989); H. Yoda, et al, *Chem Express*, 4(8), 515 (1989); and Y. Yamamoto, et al., *J Org Chem*, 56(3), 112 (1991).)

BRIEF SUMMARY OF THE INVENTION

The present invention provides a method for modifying the cyclic peptide ring system of Echinocandin-type compounds to produce new analogs having antifungal activity. The inventive process allows one to make changes in the cyclic peptide structure of natural and semi-synthetic products that were previously not possible. For example, one may incorporate features such as water-solubility into the cyclic peptide ring nucleus, sites for further modification, increase or decrease the number of amino acid or peptide units within the ring nucleus, and increase or decrease the total number of members (or atoms) in the ring nucleus.

The process includes the steps of (i) providing a cyclic peptide compound comprising a peptide unit having a γ-hydroxyl group; (ii) opening the ring of the cyclic peptide compound to provide a first linear peptide wherein the peptide unit having a γ-hydroxyl group is the N-terminus peptide unit of the first linear peptide; (iii) cleaving-off the peptide unit having a γ-hydroxyl group to provide a second linear peptide (preferably by adding trifluoroacetic acid or hydrochloric acid to the first linear peptide in an organic solvent); (iv) attaching at least one amino acid, a dipeptide unit or a synthetic unit to the second linear peptide to produce a third linear peptide; (v) cyclizing the third linear peptide to produce a modified cyclic peptide compound having a modified ring nucleus. Alternatively, a second peptide unit may be cleaved-off the second linear peptide produced in step (iii) prior to attaching the amino acid, dipeptide or synthetic unit(s) in step (iv) and subsequent cyclization in step (v). The addition of two or more units in step (iv) may be accomplished in a stepwise fashion (e.g., first one unit is attached then a second unit is attached). Of particular interest is the modification of Echinocandin-type compounds to produce novel cyclic hexapeptide and heptapeptide compounds that show inhibition of fungal and parasitic activity. The process also provides a convenient means to produce cyclic peptide compounds having the formulas I and II (including pharmaceutically acceptable salts, esters and hydrates thereof).

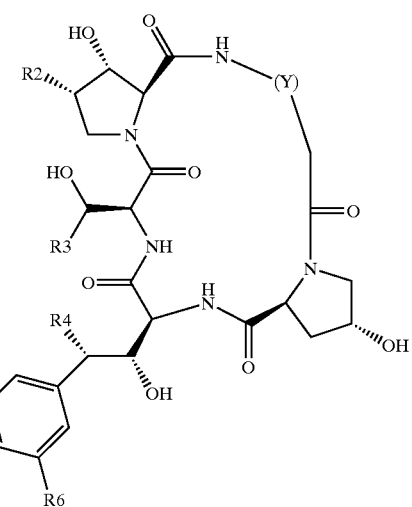

wherein
R is an alkyl group, an alkenyl group, an alkynyl group, an aryl group, or heteroaryl group;

$R^2$ is —H or —$CH_3$;
$R^3$ is —H, —$CH_3$, —$CH_2CONH_2$ or —$CH_2CH_2NH_2$;
$R^4$ is —H or —OH;
$R^5$ is —OH, —$OPO_3H_2$, or —$OSO_3H$;
$R^6$ is —H or —$OSO_3H$;
$R^7$ is —$CH_3$ or —H;

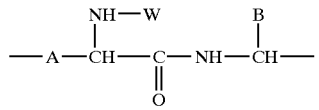

wherein
A is —$(CH_2)_a$— where a=1, 2, or 4,
—CHR'—CHR''—$(CH_2)_b$—, where R' and R'' are independently —H, —OH, $C_6H_5O$—, —SH, —$NH_2$, $C_nH_{2n+1}NH$—, $C_nH_{2n+1}O$—, $C_nH_{2n+1}S$— or $C_nH_{2n+1}$, where n=1–4 and b=0–1,
—$(CH_2)_c$—C(O)NH$(CH_2)_d$—, where c=1–2 and d=1–2,
—N=CH—$(CH_2)_e$— where e=0–2,
—NR'''$(CH_2)_f$—, where R''' is —H, —C(O)$CH_2NH_2$, —C(O)CH($NH_2$)$CH_2NH_2$ or —$C_nH_{2n+1}$ where n=1–4 and f=1–3,
—$(CH_2)_g$—$SO_2$—$(CH_2)_h$— where g=1–2 and h=1–2,

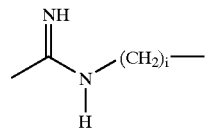

where i=1 or 2, or

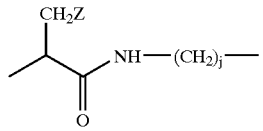

where j is 1 or 2 and Z is an amino group, alkylamino group, or piperidyl amino group;
B is a substituted or unsubstituted C1 to C6 alkyl group (e.g., isopropyl, p-hydroxybenzyl, hydroxymethyl, or α-hydroxyethyl); and W is a hydrogen or C(O)R where R is as defined above.

In another embodiment of the present invention, novel cyclic peptide compounds are provided having the formulas I and II (above) wherein
A is —$(CH_2)_a$— where a=1, 2 or 4,
—CHR'—CHR''—$(CH_2)_b$— where R' and R'' are independently —H, —OH, $C_6H_5O$—, —SH, —$NH_2$, $C_nH_{2n+1}NH$—, $C_nH_{2n+1}O$—, $C_nH_{2n+1}S$— or $C_nH_{2n+1}$, where n=1–4 and b=0,
—$(CH_2)_c$—C(O)NH$(CH_2)_d$— where c=1–2 and d=1–2,
—N=CH—$(CH_2)_e$— where e=0–2,
—NR'''$(CH_2)_f$— where R''' is —H, —C(O)$CH_2NH_2$, —C(O)CH($NH_2$)$CH_2NH_2$ or $C_nH_{2n+1}$ where n=1–4 and f=1–3,
—$(CH_2)_g$—$SO_2$—$(CH_2)_h$— where g=1–2 and h=1–2,

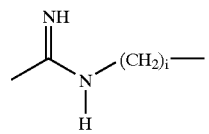

where i=1 or 2, or

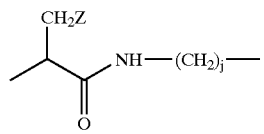

where j is 1 or 2 and Z is an amino group, alkylamino group, or piperidylamino group.

In yet another embodiment of the present invention, a pharmaceutical composition is provided comprising the novel compounds I and II described above (including pharmaceutically acceptable salts, esters and hydrates thereof) in a pharmaceutically inert carrier. Methods for using the novel compounds and pharmaceutical compositions described above for inhibiting fungal growth and parasitic activity are also provided, as well as a method for treating a fungal infection in a human comprising administering to a human in need of such treatment a therapeutically effective amount of the novel antifungal compound described above.

As used herein, the term "Echinocandin-type compounds" refers to compounds having the following general structure including any simple derivatives thereof:

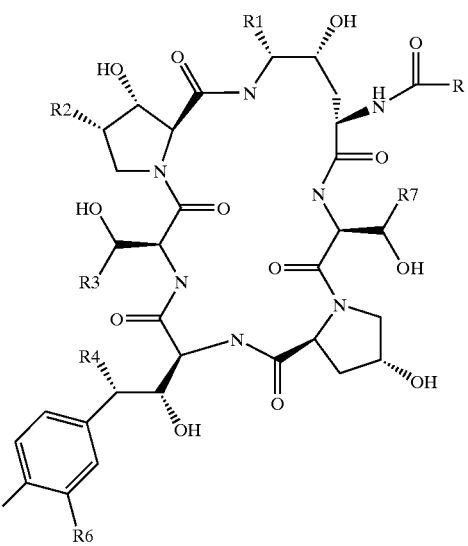

wherein R is an alkyl group, an alkenyl group, an alkynyl group, an aryl group, or heteroaryl group; $R^1$ is —H or —OH; $R^2$ is —H or —$CH_3$; $R^3$ is —H, —$CH_3$, —$CH_2CONH_2$ or —$CH_2CH_2NH_2$;
$R^4$ is —H or —OH; $R^5$ is —OH, —$OPO_3H_2$, or —$OSO_3H$; and $R^6$ is —H or —$OSO_3H$.

The term "alkyl" refers to a hydrocarbon radical of the general formula $C_nH_{2n+1}$ containing from 1 to 30 carbon atoms unless otherwise indicated. The alkane radical may be straight, branched, cyclic, or multi-cyclic. The alkane radical may be substituted or unsubstituted. Similarly, the alkyl portion of an alkoxy group or alkanoate have the same definition as above.

The term "alkenyl" refers to an acyclic hydrocarbon containing at least one carbon-carbon double bond. The alkene radical may be straight, branched, cyclic, or multi-cyclic. The alkene radical may be substituted or unsubstituted. The term "alkynyl" refers to an acyclic hydrocarbon containing at least one carbon-carbon triple bond. The alkyne radical may be straight, or branched. The alkyne radical may be substituted or unsubstituted.

The term "aryl" refers to aromatic moieties having single (e.g., phenyl) or fused ring systems (e.g., naphthalene, anthracene, phenanthrene, etc.). The aryl groups may be substituted or unsubstituted. Substituted aryl groups include a chain of aromatic moieties (e.g., biphenyl, terphenyl, phenylnaphthalyl, etc.)

The term "heteroaryl" refers to aromatic moieties containing at least one heteroatom within the aromatic ring system (e.g., pyrrole, pyridine, indole, thiophene, furan, benzofuran, imidazole, pyrimidine, purine, benzimidazole, quinoline, etc.). The aromatic moiety may consist of a single or fused ring system. The heteroaryl groups may be substituted or unsubstituted.

Within the field of organic chemistry and particularly within the field of organic biochemistry, it is widely understood that significant substitution of compounds is tolerated or even useful. In the present invention, for example, the term alkyl group allows for substituents which is a classic alkyl, such as methyl, ethyl, propyl, hexyl, isooctyl, dodecyl, stearyl, etc. The term group specifically envisions and allows for substitutions on alkyls which are common in the art, such as hydroxy, halogen, alkoxy, carbonyl, keto, ester, carbamato, etc., as well as including the unsubstituted alkyl moiety. However, it is generally understood by those skilled in the art that the substituents should be selected so as to not adversely affect the pharmacological characteristics of the compound or adversely interfere with the use of the medicament. Suitable substituents for any of the groups defined above include alkyl, alkenyl, alkynyl, aryl, halo, hydroxy, alkoxy, aryloxy, mercapto, alkylthio, arylthio, mono- and di-alkyl amino, quaternary ammonium salts, aminoalkoxy, hydroxyalkylamino, aminoalkylthio, carbamyl, carbonyl, carboxy, glycolyl, glycyl, hydrazino, guanyl, and combinations thereof.

DETAILED DESCRIPTION OF THE INVENTION

The synthetic scheme outlined below illustrates the general procedures for modifying the cyclic peptide ring system of Echinocandin-type compounds while maintaining chirality. The cyclic peptide ring of any Echinocandin-type natural product or semi-synthetic derivative can be opened and the terminal ornithine peptide unit cleaved so long as the γ-hydroxyl group of the ornithine peptide unit is present and not blocked. The term "natural product" refers to those secondary metabolites, usually of relatively complex structure, which are of more restricted distribution and more characteristic of a specific source in nature. Suitable natural product starting materials belonging to the Echinocandin cyclic peptide family include Echinocandin B, Echinocandin C, Aculeacin Aγ, Mulundocandin, Sporiofungin A, Pneumocandin $A_0$, WF 11899A, and Pneumocandin $B_0$. For illustrative purposes, the following synthetic scheme starts with Cilofungin.

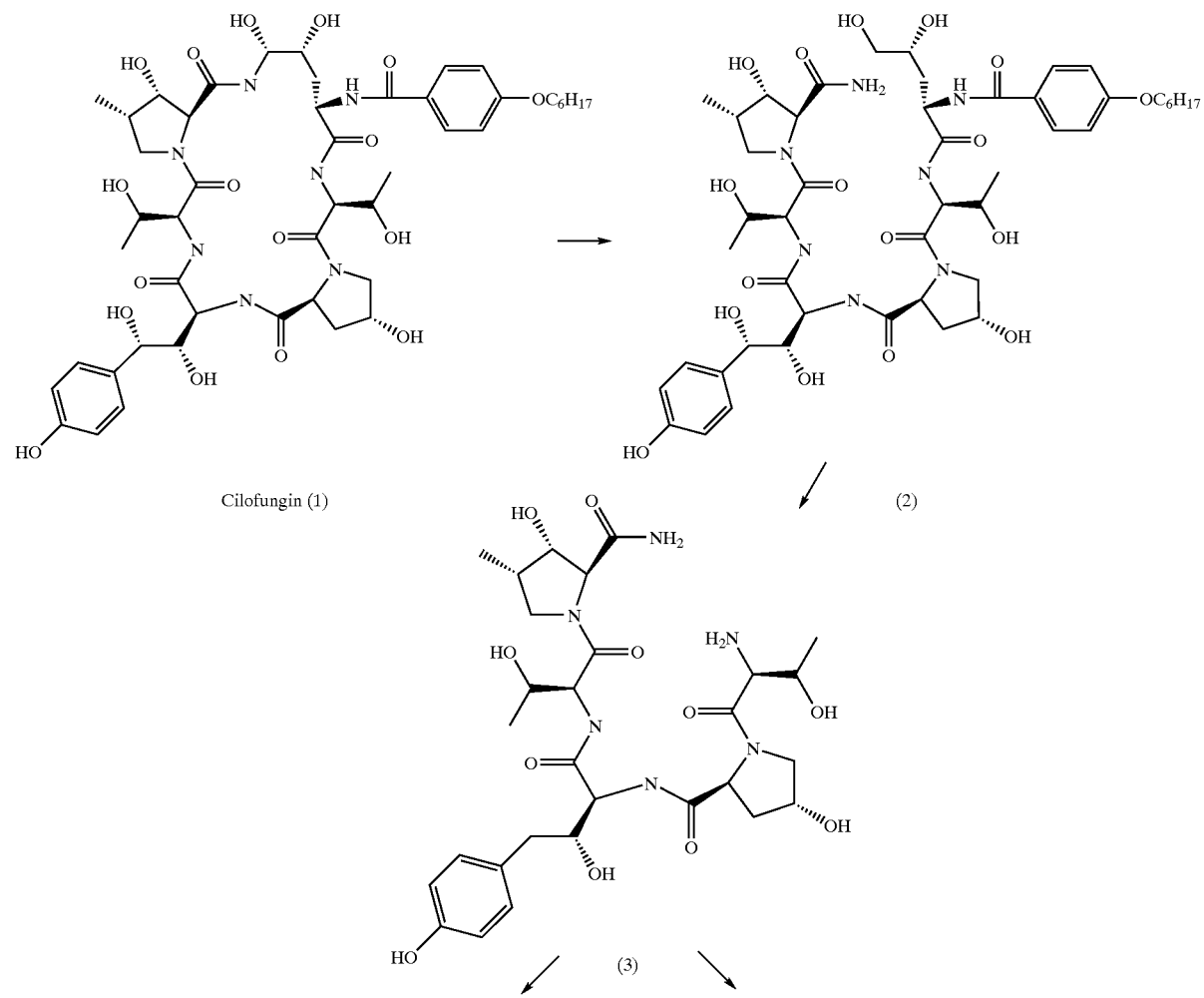

7 8
-continued
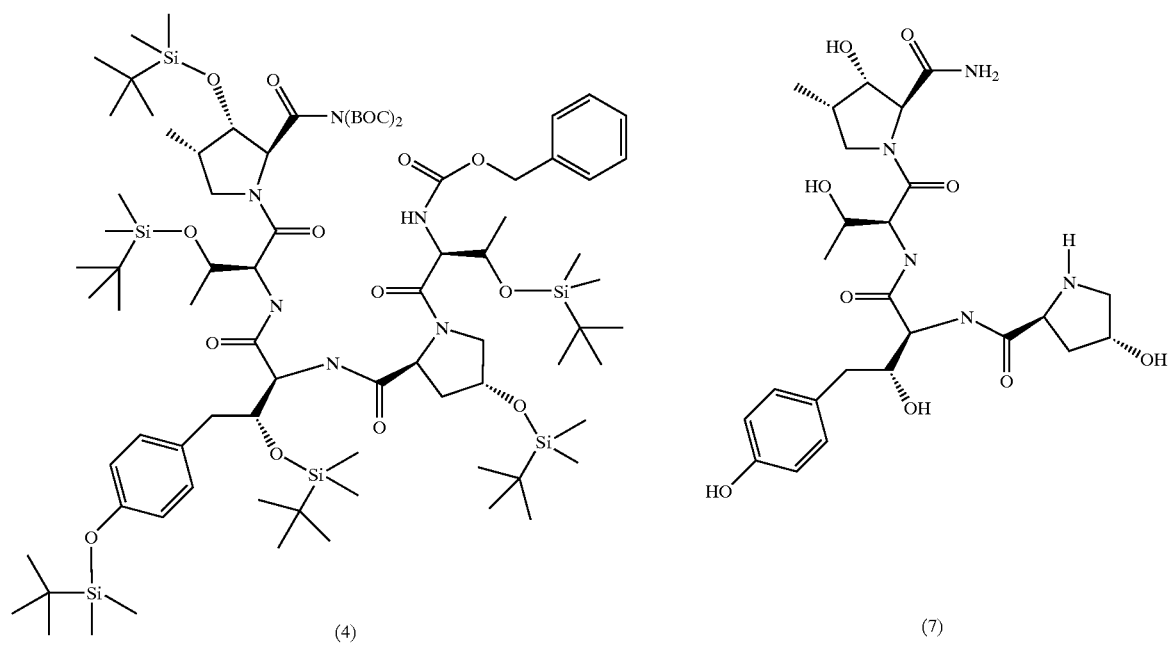
(4) (7)
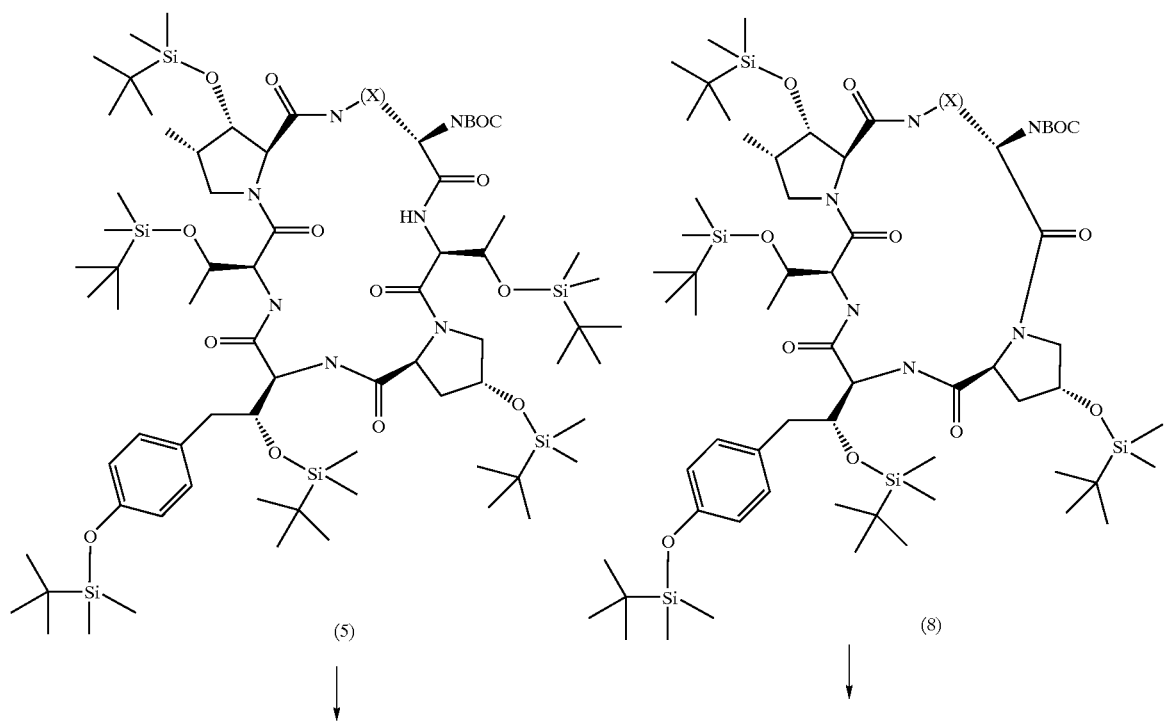
(5) (8)

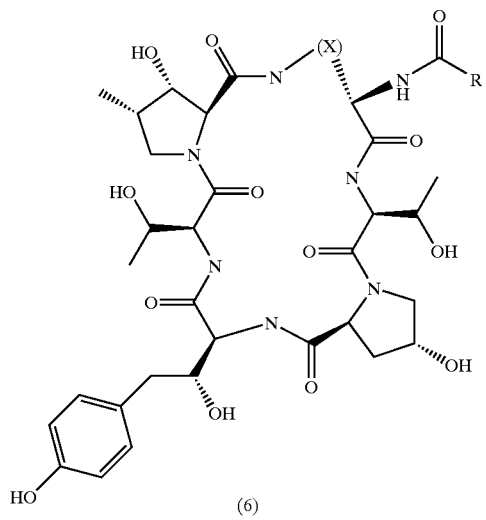

(6)

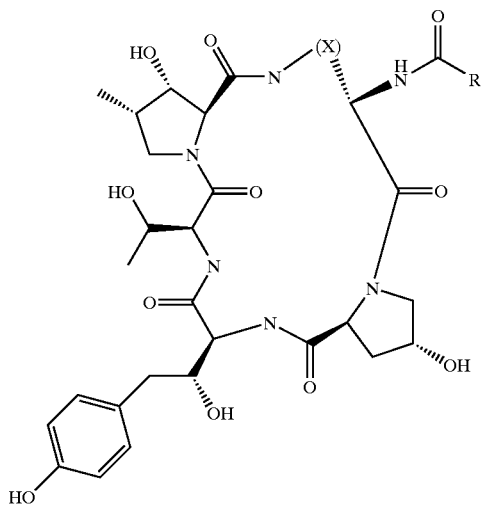

As shown above, the cyclic hexapeptide ring (1) is first opened using base catalysis and then reduced with sodium borohydride to give the linear hexapeptide (2). Upon treatment with triethyl silane in trifluoroacetic acid (TFA), the benzylic hydroxyl is removed and the ornithine unit is cleaved to give the linear pentapeptide (3). The linear pentapeptide (3) can now be protected and the primary amide activated to provide an intermediate (4) which can be recyclized with a new amino acid unit or other synthetic unit to produce a new cyclic compound (5). Cyclic compound (5) can be further modified by deprotecting and acylating the pendant amino group (if present) to provide modified cyclic compound (6) having an N-acyl side chain. Those skilled in the art will appreciate that the N-acyl side chain encompasses a variety of side chain moieties known in the art. Suitable side chain moieties include substituted and unsubstituted alkyl groups, alkenyl groups, alkynyl groups, aryl groups, heteroaryl groups and combinations thereof. Preferably, the side chain contains both a linearly rigid section and a flexible alkyl section to maximize antifungal potency. In addition, further modifications can be made on any new functionality introduced by the incorporation of the new amino acid, peptide or synthetic unit(s) containing such new functionality.

Alternatively, another peptide unit can be cleaved from intermediate (3) to provide a tetrapeptide (7) which can be recyclized with a new amino acid unit, dipeptide unit, or other synthetic unit to produce a new cyclic compound (8). Like cyclic compound (5), compound (8) can also be further modified by deprotecting and acylating the pendant amino group (if present) to attach an N-acyl side chain or modification of any new functionality introduced through the incorporation of the new amino acid, peptide or synthetic units.

As illustrated in the synthetic scheme above, the ring nucleus is selectively opened at the C-terminus L-proline, N-terminus R-ornithine linkage using standard base catalysis well known to those skilled in the art. Once the cyclic hexapeptide is open, then the terminal ornithine amino acid may be cleaved and a new amino acid (or other synthetic unit) attached using standard peptide formation processes (or condensation processes) well known to those skilled in the art. The terminal ornithine unit is cleaved with trifluoroacetic acid or hydrochloric acid in an organic solvent such as methylene chloride, toluene, or dioxane. The preferred reaction condition is trifluoroacetic acid in methylene chloride.

Any amino acid or peptide unit may be attached to the linear peptide. Theoretically, it is also possible to condense other synthetic units onto the peptide that are capable of cyclization. For example, a sulfonamide linkage may be formed between a terminal amino group on the linear peptide and a sulfonyl group on a synthetic unit. Any number of other linkages may also be envisioned; however, the pharmaceutical activity of such compounds are currently unknown.

The insertion of a new amino acid, dipeptide unit or other synthetic unit allows one to change the size of the cyclopeptide ring. The number of atoms in the ring system may be increased or decreased from the original 21 membered Echinocandin ring structure depending upon the particular compound(s) inserted into the ring. Theoretically, the ring size is limited only by the configuration of the linear peptide. If the linear peptide is too short or too long, the ends cannot come into close enough proximity to react and the ends may polymerize with another linear peptide rather than close to form a ring. The optimum configuration of the linear peptide for ring closure will vary depending upon the particular amino acids that make-up the peptide structure. For Echinocandin-type compounds, preferably, the final ring structure contains between 19 to 22 members, more preferably, the final ring structure is a 21- or 22-membered ring, most preferably the final ring structure is a 21-membered ring.

It is well-known that the acyl side chain pendant from the Echinocandin ring structure plays an important role in the activity of both the natural products and semi-synthetic Echinocandin type materials. Consequently, any amino acid or synthetic unit may be used for insertion into the ring so long as the final cyclized product contains at least one amino group capable of acylation.

When the inserted compound contains more than one unit, the units may be attached one at a time to the linear penta- or tetra-peptide or the individual units can be combined and then added to the linear penta- or tetra-peptide as a block unit. Preferably, the units are added as a block unit to minimize racemization.

Acylation of the amino group may be accomplished in a variety of ways well known to those skilled in the art. For example, the amino group may be acylated by reaction with an appropriately substituted acyl halide, preferably in the presence of an acid scavenger such as a tertiary amine (e.g., triethylamine). The reaction is typically carried out at a temperature between about −20° C. to 25° C. Suitable reaction solvents include polar aprotic solvents, such as dioxane or dimethylformamide. Solvent choice is not critical so long as the solvent employed is inert to the ongoing reaction and the reactants are sufficiently solubilized to effect the desired reaction.

The amino group may also be acylated by reaction with an appropriately substituted carboxylic acid, in the presence of a coupling agent Suitable coupling agents include dicyclohexylcarbodiimide (DCC), N,N'-carbonyldiimidazole, bis (2-oxo-3-oxazolidinyl)phosphinic chloride (BOP-Cl), N-ethoxycarbonyl-2-ethoxy-1,2-dihydroquinoline (EEDQ), benzotriazole-1-yloxy-tripyrrolidinophosphonium hexafluorophosphate (PyBOP) and the like.

Alternately, the amino group may be acylated with an activated ester of a carboxylic acid such as p-nitrophenyl, 2,4,5-trichlorophenyl, hydroxybenzotriazole hydrate (HOBT.H$_2$O), pentafluorophenol, and N-hydroxysuccinimide carboxylate esters. Preferred acylating moieties are the 2,4,5-trichlorophenyl and HOBT carboxylate esters. The reaction is typically ran 1 to 65 hours at a temperature from about 0° C. to 30° C. in an aprotic solvent. The reaction is generally complete after about 24 to 48 hours when carried out at a temperature between about 15° C. to 30° C. Suitable solvents include tetrahydrofuran and dimethylformamide or mixtures thereof. The amino group is generally present in equimolar proportions relative to the activated ester or with a slight excess of the amino group.

The compounds of the present invention may be isolated and used per se or in the form of its pharmaceutically acceptable salt or hydrate. The term "pharmaceutically acceptable salt" refers to non-toxic acid addition salts derived from inorganic and organic acids. Suitable salt derivatives include halides, thiocyanates, sulfates, bisulfates, sulfites, bisulfites, arylsulfonates, alkylsulfates, phosphonates, monohydrogenphosphates, dihydrogenphosphates, metaphosphates, pyrophosphonates, alkanoates, cycloalkylalkanoates, arylalkonates, adipates, alginates, aspartates, benzoates, fumarates, glucoheptanoates, glycerophosphates, lactates, maleates, nicotinates, oxalates, palmitates, pectinates, picrates, pivalates, succinates, tartarates, citrates, camphorates, camphorsulfonates, digluconates, trifluoroacetates, and the like.

The ring-modified compounds may be used in a variety of pharmaceutical formulations. A typical formulation comprises the ring-modified compound (or its pharmaceutically acceptable salt, ester or hydrate) in combination with a pharmaceutically acceptable carrier, diluent or excipient. The active ingredient is typically formulated into pharmaceutical dosage forms to provide an easily controllable dosage of the drug and to give the patient an elegant and easily handleable product. Formulations may comprise from 0.1% to 99.9% by weight of active ingredient, more generally from about 10% to about 30% by weight.

As used herein, the term "unit dose" or "unit dosage" refers to physically discrete units that contain a predetermined quantity of active ingredient calculated to produce a desired therapeutic effect. When a unit dose is administered orally or parenterally, it is typically provided in the form of a tablet, capsule, pill, powder packet, topical composition, suppository, wafer, measured units in ampoules or in multidose containers, etc. Alternatively, a unit dose may be administered in the form of a dry or liquid aerosol which may be inhaled or sprayed.

The dosage to be administered may vary depending upon the physical characteristics of the patient, the severity of the patient's symptoms, and the means used to administer the drug. The specific dose for a given patient is usually set by the judgment of the attending physician.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the active ingredient is being applied. The formulations may also include wetting agents, lubricating agents, emulsifiers, suspending agents, preservatives, sweeteners, stabilizers, perfuming agents, flavoring agents and combinations thereof.

A pharmaceutical composition may be administered using a variety of methods. Suitable methods include topical (e.g., ointments or sprays), oral, injection and inhalation. The particular treatment method used will depend upon the type of infection being addressed.

Echinocandin-type compounds have been shown to exhibit antifungal and antiparasitic activity such as growth inhibition of various infectious fungi including *Candida* spp. (i.e., *C. Albicans, C. Parapsilosis, C. Krusei, C. Glabrata, C. Tropicalis*, or *C. Lusitaniaw*); *Torulopus* spp. (i.e., *T. Glabrata*); *Aspergillus* spp. (i.e., *A. Fumigatus*); *Histoplasma* spp. (i.e., *H. Capsulatum*); *Cryptococcus* spp. (i.e., *C. Neoformans*); *Blastomyces* spp. (i.e., *B. Dermatitidis*); *Fusarium* spp.; *Trichophyton* spp., *Pseudallescheria boydii, Coccidioides immits, Sporothrix schenckii*, etc.

Compounds of this type also inhibit the growth of certain organisms primarily responsible for opportunistic infections in immunosuppressed individuals, such as growth inhibition of *Pneumocystis carinii* (the causative organism of pneumocystis pneumonia (PCP) in AIDS and other immunocompromised patients. Other protozoans that are inhibited by Echinocandin-type compounds include *Plasmodium* spp., *Leishmania* spp., *Trypanosoma* spp., *Cryptosporidium* spp., *Isospora* spp., *Cyclospora* spp., *Trichomnas* spp., *Microsporidiosis* spp., etc.

The compounds of the present invention are useful in combating either systemic fungal infections or fungal skin infections. Accordingly, a method is provided for inhibiting fungal activity comprising contacting a compound of formula I or II (or a pharmaceutically acceptable salt, ester or hydrate thereof) with a fungus. A preferred method includes inhibiting *Candida albicans* or *Aspergillus fumigatis* activity. The term "contacting" includes a union or junction, or apparent touching or mutual tangency of a compound of the invention with a parasite or fungus. The term does not imply any further limitations to the process, such as by mechanism of inhibition. The methods are defined to encompass the inhibition of parasitic and fungal activity by the action of the compounds and their inherent antiparasitic and antifungal properties.

A method for treating a fungal infection which comprises administering an effective amount of a compound of formula I or II (or a pharmaceutically acceptable salt, ester or hydrate thereof) to a host in need of such treatment is also provided. A preferred method includes treating a *Candida albicans* or *Aspergillus fumigatis* infection. The term "effective amount" refers to an amount of active compound which is capable of inhibiting fungal activity. The dose administered will vary depending on such factors as the nature and severity of the infection, the age and general health of the host and the tolerance of the host to the antifungal agent. The particular dose regimen likewise may vary according to these factors. The medicament may be given in a single daily dose or in multiple doses during the day. The regimen may last from about 2–3 days to about 2–3 weeks or longer. A typical daily dose (administered in single or divided doses) contains a dosage level between about 0.01 mg/kg to 100 mg/kg of body weight of an active compound. Preferred daily doses are generally between about 0.1 mg/kg to 60 mg/kg and more preferably between about 2.5 mg/kg to 40 mg/kg.

Although the compounds described herein may be used for inhibiting fungal and parasitic activity in a variety of circumstances (e.g., humans, animals, agriculture, etc.), preferably, the methods of use are limited to the treatment of humans to reduce the potential for developing resistance to the pharmaceutical.

EXAMPLES

Unless indicated otherwise, all chemicals can be acquired from commercial suppliers such as Aldrich Chemical (Milwaukee, Wis.), Sigma, and other commercial sources well-known to those skilled in the art. The following acronyms are representative of the corresponding functional groups or compounds:

BOC=t-butoxycarbonyl, $(CH_3)_3C—O—C(O)—$

CBZ=benzyloxycarbonyl, $C_6H_5CH_2—O—C(O)—$ o-Cl-CBZ=ortho-chlorobenzyloxycarbonyl FMOC=fluorenylmethyloxycarbonyl TBDMS=t-butyldimethylsilyl TFA=trifluoroacetic acid AcN=acetonitrile DMF=dimethylformamide THF=tetrahydrofuran TDM=4,4'-tetramethyl-diamino-diphenylmethane CAM=ceric ammonium molybdate The following set of examples illustrate the general reaction conditions for cleaving and inserting new unit(s) into a cyclohexapeptide nucleus.

Preparation of Key Intermediates
Ring Opening and Reduction of Cilofungin (1) to Give Intermediate I-2.

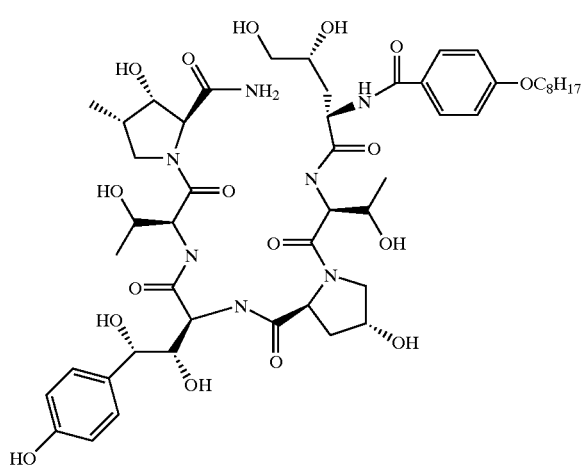

I-2

To a stirred solution of Cilofungin (1) (100 g; 96 mmol) in 350 ml of 55% acetonitrile/45% water was added 1 N sodium hydroxide solution (40 ml). The reaction was monitored by high pressure liquid chromatography (C-18 column, 50% AcN/water, 230 nm). After 1 hour, the reaction mixture contained >90% of the intermediate aldehyde. Next, sodium borohydride (1.8 g; 48 mmol) was added and the stirring continued for 20 min. HPLC showed complete conversion to the final alcohol product. The reaction was quenched by adding acetic acid dropwise until the evolution of gas was complete. Most of the acetonitrile was removed by rotary evaporation followed by lyophilization to remove the remainder to give 98.1 g of a mixture of the solid product I-2 and inorganic salts. (93% pure by HPLC)

Peptide Cleavage and Deoxygenation of I-2 to Give Pentapeptide (I-3)

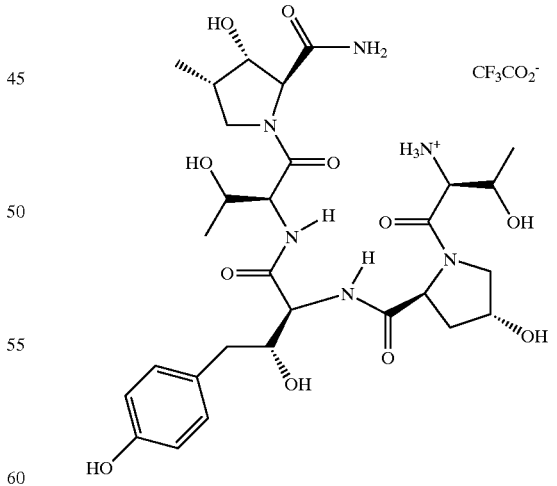

I-3

The unpurified mixture of Compound I-2 (98.1 g) described above was dissolved in trifluoroacetic acid (300 ml) and dichloromethane (100 ml). The mixture was cooled in an ice bath. Triethylsilane (32 ml; 0.2 mol) was added and the reaction was stirred at 0° C. for 1 hour. The ice bath was removed and the reaction was left at ambient temperature for 18 hrs. The solvent was removed in vacuo and the residue redissolved in methanol for HPLC purification. The residue was purified by passage through a C-18 column with 50% acetonitrile/water; 0.1% TFA to remove more lipophilic byproducts. The polar peaks were purified with 10% acetonitrile/water; 0.1% TFA. Lyophilization gave 57.8 g (98% yield) of pure pentapeptide trifluoroacetic acid salt (I-3). FAB MS=653.3 (M+1)

Preparation of CBZ Pentapeptide (I-4)

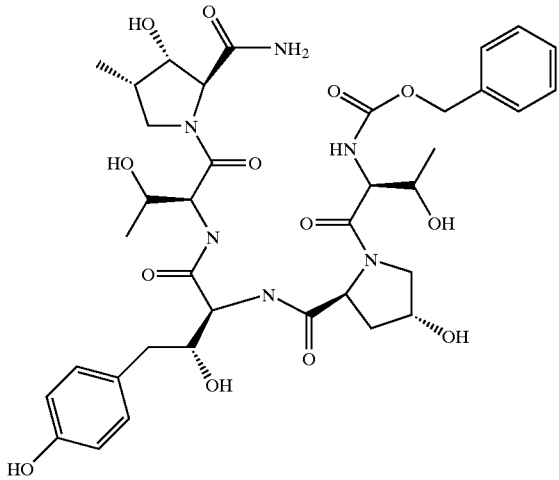

I-4

To an ice bath cooled solution of I-3 (50.3 g, 66 mmol) in water (200 ml) and tetrahydrofuran (100 ml) was added excess solid sodium bicarbonate until no additional foaming occurred and pH>8. Carbobenzyloxy chloride (10 ml, 70 mmol) was added and the reaction was monitored by HPLC (25% AcN/water, 0.1% TFA, 230 nm). The pH was monitored and occasionally more sodium bicarbonate was added to keep the solution basic. After 1 hour, the reaction was complete and the solvent was removed in vacuo. The residue was slurried in methanol, the solid inorganics removed by filtration, and the solution was passed through a preparative HPLC (25% methanol/water). Removal of solvents gave 25.2 g (49% yield) of I-4 as a white foam. FAB MS=787.38 (M+1)

Preparation of Silyl CBZ Pentapeptide (I-5)

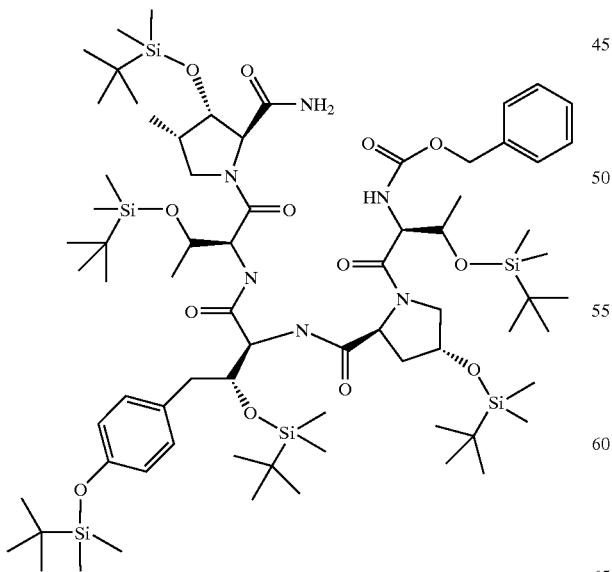

I-5

Compound I-4 (25.2 g, 32 mmol), imidazole (20.6 g, 303 mmol), and t-butyldimethylsilyl chloride 45.6 g, 303 mmol) in dimethylformamide (250 ml) were mixed while following the reaction by TLC (25% ethyl acetate/hexane). After 6 hours, the solvent was removed in vacuo and the residue was slurried and sonicated in ether. The ether solution was washed with 1N HCl, dried over MgSO₄ and reduced in vacuo to give a foam. The crude product was purified by flash chromatography (600 g silica, 25% ethyl acetate/hexane) to give 32.9 g (70% yield) of a white foam. NMR data was consistent with the structure I-5.

FAB MS=1472.9 (M)

Preparation of DiBOC CBZ Silyl Pentapeptide (I-6)

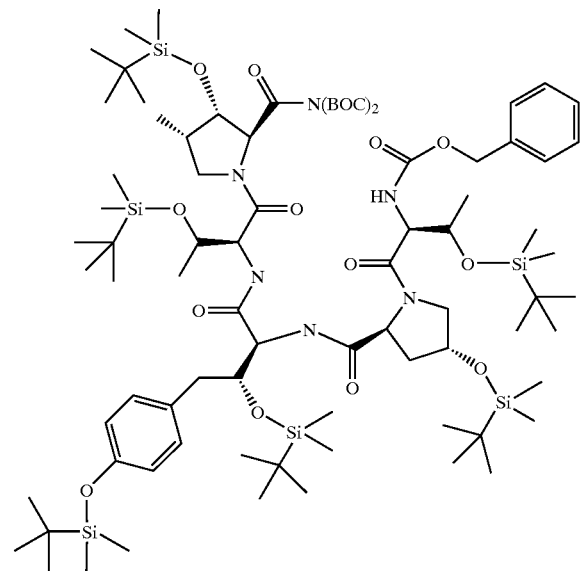

I-6

Compound I-5 (32.9 g, 22.3 mmol) was dissolved in acetonitrile (250 ml) and tetrahydrofuran (50 ml). Di-t-butyl dicarbonate (16.1 g, 73.6 mmol) and dimethylaminopyridine (299 mg, 2.2 mmol) were added with stirring. The reaction was followed by TLC (20% ethyl acetate/hexane) and an additional 3 g of di-t-butyl dicarbonate was added after 2 hrs. After an additional 2.5 hours, several ml of acetic acid were added to quench the dimethylaminopyridine. The solvent was removed in vacuo keeping the temperature less than 40° C. The residue was chromatographed (500 g silica, 15% ethyl acetate/hexane) to give 33.6 g (89% yield) of a white foam. NMR data was consistent with the structure I-6.

FAB MS=1672.0 (M)

Preparation of the Intermediate Linear Tetrapeptide (I-7):

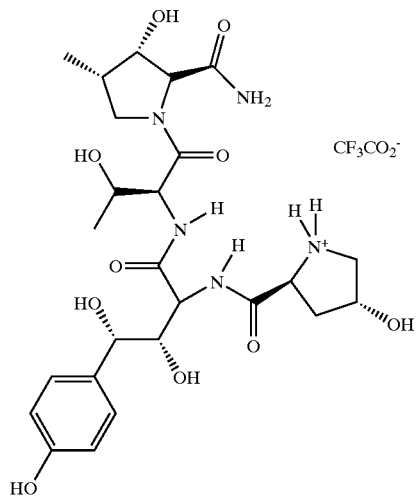

I-7

To a solution of Pentapeptide Compound I-3 (5.75 g, 7.50 mmol) in anhydrous DMF (200 ml) was added NaHCO$_3$ (690 mg, 8.25 mmol) and phenyl isothiocyanate (0.99 ml, 8.25 mmol), and the reaction stirred at room temperature for 36 hours. The solids were removed by filtration and the filtrate was concentrated in vacuo. The resulting oil was dissolved in TFA (70 ml) and stirred at room temperature for 1 hour, followed by removal of the solvent in vacuo. The resulting solids were treated with water (150 ml), sonicated, and the insoluble materials were removed by filtration. Reverse phase HPLC of the filtrate (eluting with 4% AcN/ 0.1% TFA/H$_2$O) followed by lyophilization gave 3.20 g of a fluffy white solid, 64% yield. The $^1$H NMR (300 MHz) spectrum was consistent with the structure I-7. FAB MS (M$^+$ of free base)=552.

Example 1 illustrates the general reaction conditions for converting pentapeptide intermediate (I-6) into a cyclic hexapeptide analog of an Echinocandin-type compound.

Example 1

Preparation of DiBOC Silyl o-Cl-CBZ Hexapeptide (E1-1)

A solution of N-α-BOC-N-γ-(2-chloro CBZ)-L-ornithine (480 mg, 1.2 mmol), N-hydroxysuccinimide (138 mg, 1.2 mmol), and dicyclohexylcarbodiimide (247 mg, 1.2 mmol) in 4 ml of tetrahydrofuran was stirred overnight to form the active ester. A solution of I-6 (1.0 g, 0.598 mmol) in ethanol (5 ml) was added to a slurry of 10% Pd/C (250 mg) in 5 ml of ethanol followed by 10 ml of glacial acetic acid. The mixture was put under a balloon of H$_2$ and after 1 hour the starting material was gone. The catalyst was removed by filtration and the solution was carefully reduced under high vacuum keeping the temperature under 40° C. The resulting oil was dissolved in ether and the previously prepared tetrahydrofuran solution of active ester was added followed by excess triethylamine until the solution was basic to pH paper. After stirring for 2 hours, the solution was extracted with saturated NaHCO$_3$ solution followed by dilute HCl solution and then another portion of saturated NaHCO$_3$ solution. The organic layer was dried over MgSO$_4$ and reduced in vacuo to give 0.85 g of the crude product. Purification by flash chromatography (25% ethyl acetate/ hexane) gave 0.53 g of coupled product E1-1

(47% yield). NMR data was consistent with the structure E1-1. FAB MS=1922.2 (M+1)

Cyclization of E1-1 to BOC Silyl Cyclohexapeptide (E1-2)

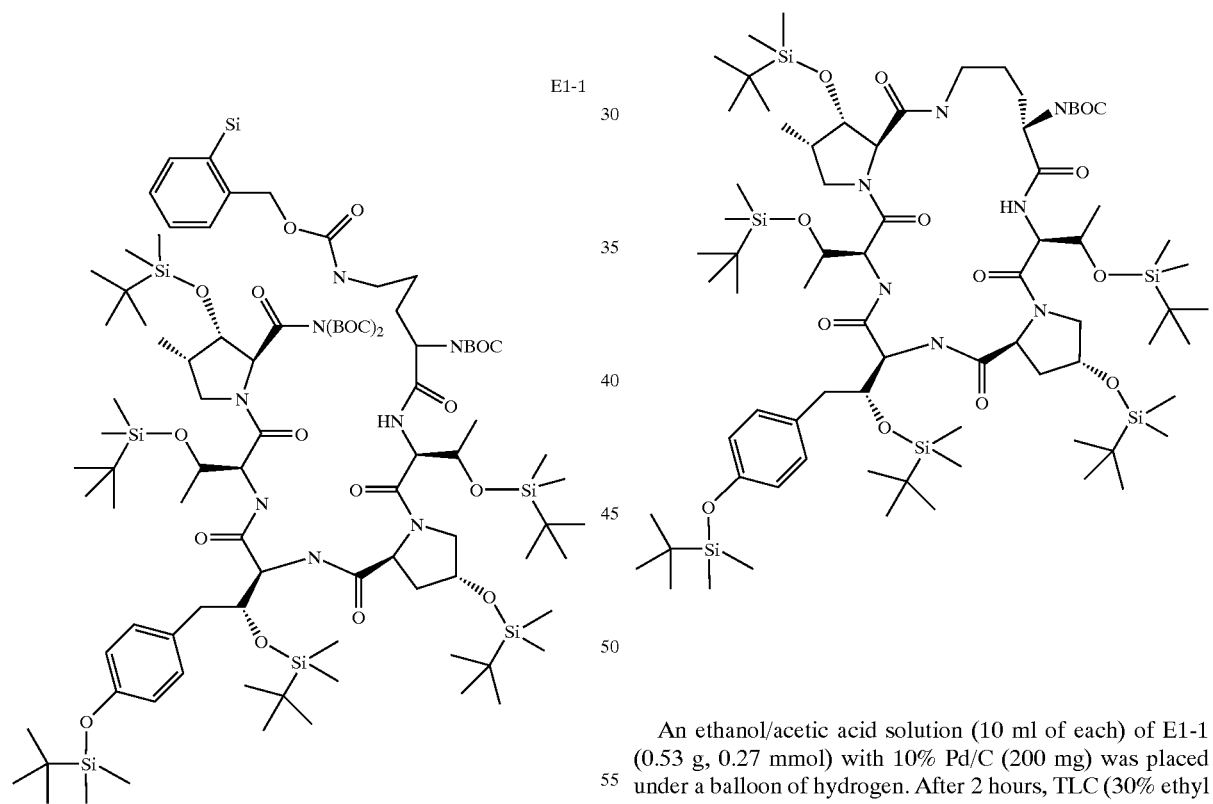

An ethanol/acetic acid solution (10 ml of each) of E1-1 (0.53 g, 0.27 mmol) with 10% Pd/C (200 mg) was placed under a balloon of hydrogen. After 2 hours, TLC (30% ethyl acetate/hexane) indicated a complete reaction. The catalyst was removed by filtration and the solvent reduced in vacuo at 40° C. until the residue was a thick oil. The residue was dissolved in ethyl ether (150 ml) and excess triethylamine was added until the solution was basic to pH paper (~2 ml). After 18 hours, TLC indicated a single product spot. The solvent was removed in vacuo and the residue purified over a flash column to provide 343 mg of a white solid (81% yield). NMR data was consistent with the structure E1-2.

FAB MS=1536.0 (M+1)

Removal of Protecting Groups and Coupling of the Side Chain to Give E1-3

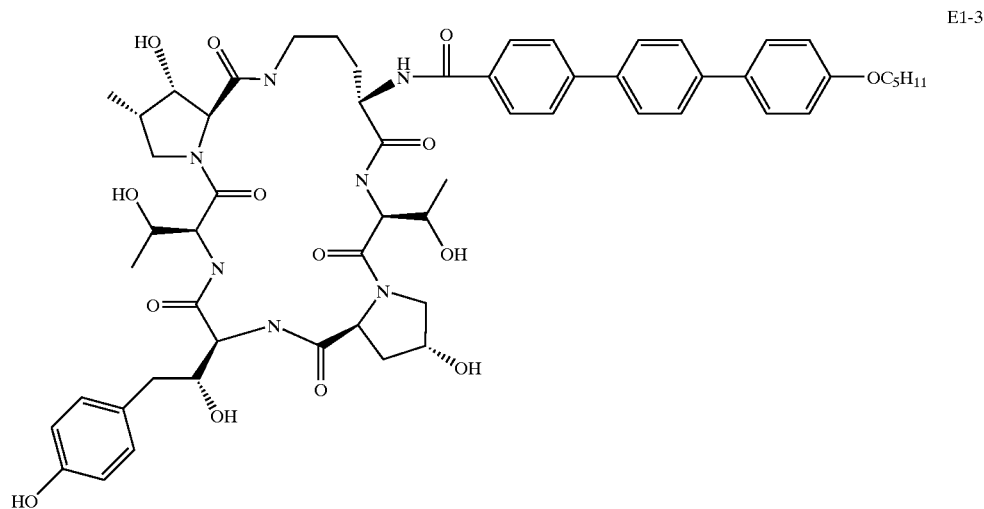

E1-3

Compound E1-2 (510 mg, 0.332 mmol) was dissolved in 5 ml trifluoroacetic acid at 0° C. After 0.5 hour, water (0.5 ml) was added and the mixture stirred for 0.5 hour longer. The solvent was removed in vacuo and the residue was dissolved in 1N HCl (2 ml) and tetrahydrofuran (2 ml). The solution was refrigerated for 48 hours after which HPLC analysis (15% AcN/water, 230 nm) showed a single product peak. The solvent was removed under high vacuum giving a foam residue which was dissolved in dimethylformamide (8 ml). The terphenyl hydroxybenzotriazole active ester (191 mg, 0.4 mmol) and triethylamine (0.2 ml, 1.4 mmol) were added to the solution. After 4 hours, HPLC (60% AcN/water, 230 nm) showed complete conversion to a new product peak. The solvent was removed under high vacuum and purified by preparative HPLC using the analytical conditions. Solvent removal from the pure fractions gave 238 mg (66% yield) of a white solid. NMR data was consistent with the structure E1-3. FAB MS calculated for $C_{58}H_{74}N_7O_{14}$ 1092.5294. found 1092.5301 (M).

The following examples provide further illustrations of converting key intermediate (I-6) into a cyclic hexapeptide analog. In a similar manner I-6 was converted to each of the following cyclic peptides:

Coupling with Nα-BOC-Nδ-CBZ-D-ornithine and subsequent cyclization gave 63.9 mg of E1-4 (21-membered ring). FAB MS calculated for $C_{58}H_{74}N_7O_{14}$ 1092.5294. found 1092.5280.

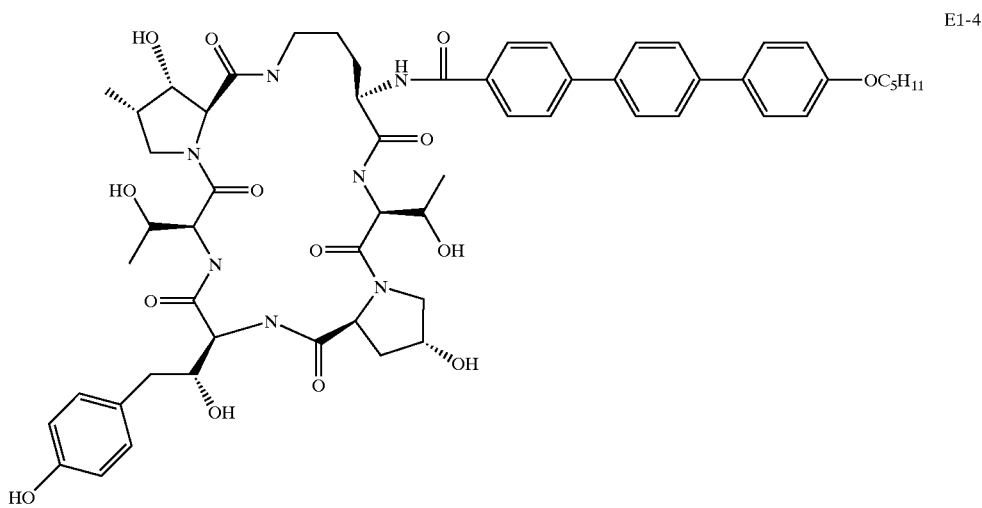

E1-4

Coupling with Nα-BOC-Nε-CBZ-L-lysine and subsequent cyclization gave 44.1 mg of E1-5 (22-membered ring). FAB MS calculated for $C_{59}H_{76}N_7O_{14}$ 1106.5450. found 1106.5464.

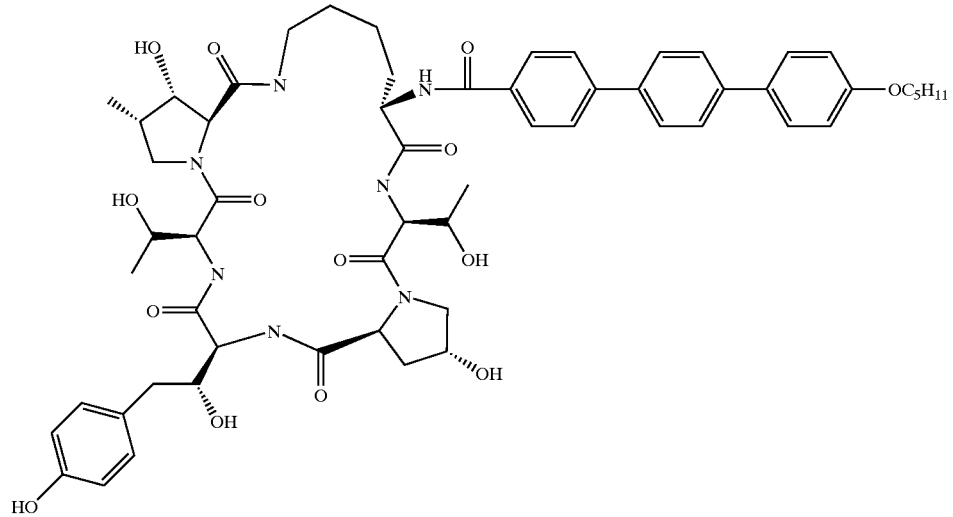

E1-5

Coupling with Nα-FMOC-Nδ-CBZ-L-2,4-diaminobutyric acid and subsequent cyclization gave 65.0 mg of E1-6 (20-membered ring). FAB MS calculated for $C_{57}H_{72}N_7O_{14}=1078.5137$. found 1078.5128.

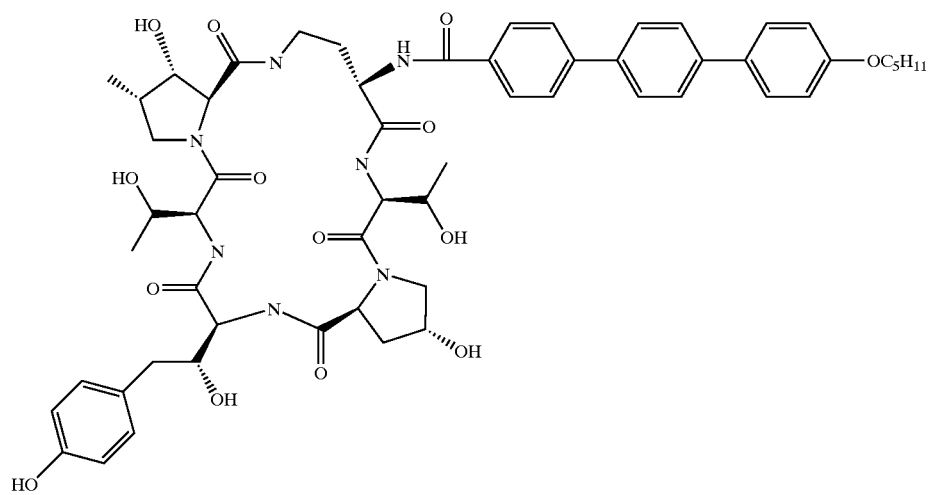

E1-6

Coupling with Nα-BOC-Nβ-CBZ-L-2,3-diaminopropionic acid and subsequent cyclization gave 25.5 mg of E1-7 (19-membered ring). FAB MS calculated for $C_{56}H_{70}N_7O_{14}$ 1064.4981. found 1064.4994.

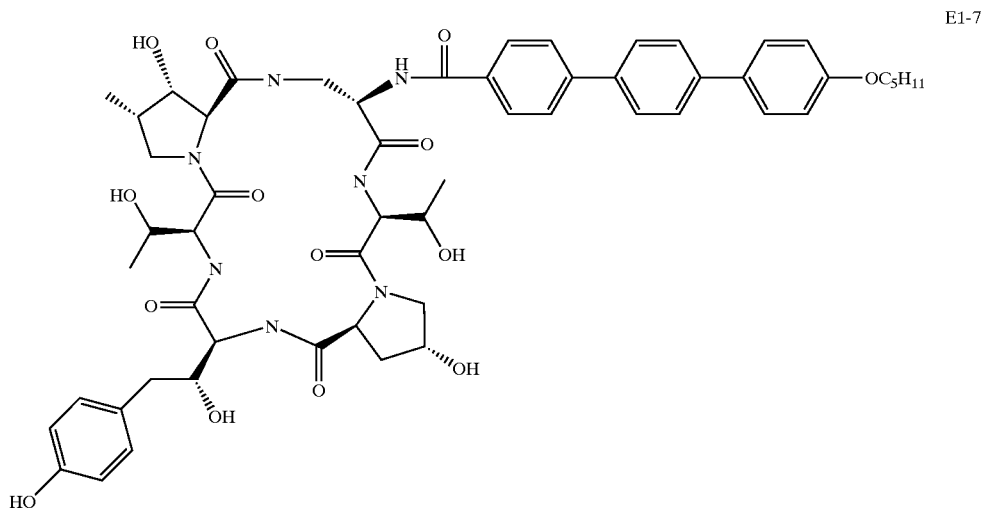

E1-7

Table 1 summarizes the activity data for compounds E1-3 through E1-7 in comparison with the following comparative semi-synthetic Echinocandin compound C1 which has proven in vitro and in vivo antifungal activity. In a murine model of organ recovery, Compound C1 significantly reduced the number of A. Fumigatus recovered from the kidneys and was as effective as amphotericin B on a mg/kg basis when both were administered intraperitoneally. In a Pneumocystis carinii model, Compound C1 reduced the number of cysts in the lungs of heavily infected, immuno-suppressed rats by more than 99% when administered orally at 5 mg/kg once daily for 4 days. Prophylactic oral administration of 1 mg/kg twice daily for 4 weeks resulted in >90% reduction in all life cycle forms. (see Turner, W. W. and M. J. Rodriguez, *Current Pharmaceutical Design*, 1996, 2, p214.)

Antifungal activity of the comparative and test compounds were determined in vitro by obtaining the minimum inhibitory concentration (MIC) of the compound using a standard agar dilution test or a disc-diffusion test.

TABLE 1

| Example No. | Minimal Inhibitory Concentration MIC ($\mu$g/ml) | | | |
| --- | --- | --- | --- | --- |
| | C. albicans | C. parapsilosis | A. fumigatus | Histoplasma capsulatum |
| Comparative C1 (21-membered ring) | 0.01 | 0.156 | 0.02 | 0.01 |

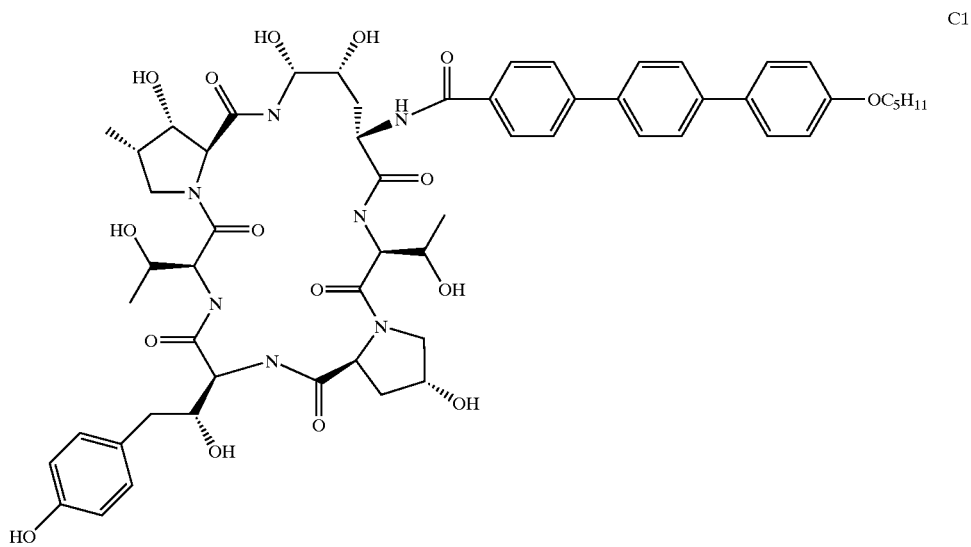

C1

TABLE 1-continued

|  | Minimal Inhibitory Concentration MIC (µg/ml) | | | |
| --- | --- | --- | --- | --- |
| Example No. | C. albicans | C. parapsilosis | A. fumigatus | Histoplasma capsulatum |
| E1-3 (21-membered ring) | 0.005 | 0.156 | 0.078 | 0.156 |
| E1-4 (21-membered ring) | 1.25 | >20 | 20.0 | 5.0 |
| E1-5 (22-membered ring) | 0.02 | >20 | 2.5 | 0.156 |
| E1-6 (20-membered ring) | 0.039 | >20 | 20 | 0.078 |
| E1-7 (19-membered ring) | 0.312 | >20 | 0.625 | 0.625 |

Example 2 illustrates the conversion of intermediate I-6 into an azacyclic hexapeptide analog of an Echinocandin-type compound.

Example 2
Preparation of the N-BOC, Benzyl, Aldehyde Derivative of L-Homoserine (E2-1)

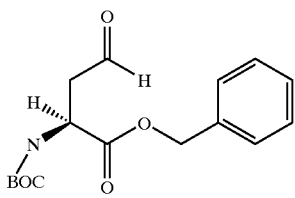

E2-1

The following procedure described in Baldwin & Flinn, *Tetrahedron Lett.*, 26(31), 3605, (1987) was used to prepare E2-1. A suspension of L-homoserine (5 g, 42 mmol) in 20 ml of water was treated with solid sodium bicarbonate (3.5 g, 42 mmol). The mixture was stirred at room temperature for approx. 10 minutes. A solution of di-t-butyl dicarbonate (BOC anhydride) (13.75 g, 63 mmol) in 20 ml of p-dioxane was added to the mixture and then stirred vigorously at room temperature for approx. 60 hours. The resulting homogenous solution was reduced in vacuo to yield a colorless oil. A solution of benzyl bromide (10.8 g, 63 mmol) in 50 ml of dimethyl formamide was added to the residue. Another 1.8 g (0.5 eq more) of solid sodium bicarbonate was added to the reaction and the mixture was allowed to stir at room temperature overnight. The reaction was monitored by thin layer chromatography (1:1 chloroform/methanol, plus 1 drop of glacial acetic acid, developed using TDM stain). The volatiles were removed in vacuo and ethyl acetate was added to the resulting residue. The organic layer was washed with water (2 times), then brine. The organic layer was dried over sodium sulfate, filtered and concentrated to yield 14.7 g of a light-yellow oil. The residue was dissolved in 50 ml of dimethyl sulfoxide. Triethylamine (12.7 g, 126 mmol) was added and the mixture was cooled in an ice-bath. A suspension of sulfur trioxide/pyridine complex (20 g, 126 mmol) in 50 ml of dimethylsulfoxide was added with stirring. The ice-bath was removed and the mixture was allowed to warm to room temperature. After approx. 10 minutes, the reaction mixture was poured into 200 ml of ice-water. The aqueous layer was extracted twice with ethyl acetate, the ethyl acetate extract was washed once with 0.1N sodium bisulfate, once with water and then finally with brine. The organic layer was dried over sodium sulfate, filtered and concentrated in vacuo to yield a yellow oil. Flash silica gel column purification chromatography (approx. 250 g, 30% ethyl acetate/hexane) yielded 11.1 g (86%) of a light-yellow oil. NMR and elemental analysis (C,H,N) data were consistent with structure E2-1. MS(FD+)=308 (M+H)

Preparation of the Dimethyl Acetal of Compound E2-1 (E2-2)

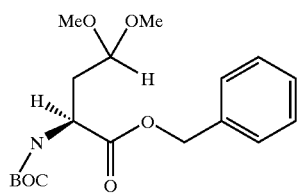

E2-2

Compound E2-1 (4 g) was dissolved in 50 ml of methanol and then cooled in an ice-bath. A light blanket of HCl gas was introduced over the stirring solution (approx. 2–3 seconds of gas allowed in) and the solution was allowed to continue to stir cold. The reaction was monitored by TLC (30% ethyl acetate/hexane, CAM stain). Additional amounts of HCl gas were added as necessary to drive the reaction to completion. After approx. 2 hours, the reaction appeared to be complete. While still cold, the reaction was quenched by adding solid sodium bicarbonate and keeping the pH slightly on the basic side. The volatiles were removed in vacuo. Ether was added to the residue. The ether layer was washed once with saturated sodium bicarbonate. The aqueous layer was back-extracted with ether. The combined ether extracts were then washed once with brine and dried over sodium sulfate, filtered and concentrated in vacuo to yield 4.6 g (100%) of a clear, colorless oil. NMR and elemental analysis (CHN) data were consistent with the structure E2-2.
MS(FD+)=354 (M+H)
Debenzylation of Compound E2-2 (E2-3)

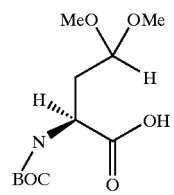

E2-3

Compound E2-2 (4.2 g, 11.9 mmol) was dissolved in 50 ml of ethyl acetate. The solution was evacuated/purged with nitrogen 3 times, then 1.9 g of 5% palladium on charcoal catalyst was added. The flask was evacuated one more time and then hydrogen was introduced into the flask. The reaction was monitored by TLC (40% ethyl acetate/hexane) and after approx. 2 hours, the reaction was complete. The hydrogen was removed in vacuo, the solution was purged with nitrogen, Celite filter aid was added, stirred, filtered through a small bed of Celite on a sintered glass funnel, rinsed with ethyl acetate and the filtrate concentrated in vacuo to yield 3.1 g (100%) of a colorless oil. NMR data was consistent with the structure E2-3. MS(FD+)=264 (M+H) Elemental Analysis (CHN): Theoretical % (C—50.18; H—8.04; N—5.32) Observed % (C—51.14; H—7.56; N—5.65)

Coupling of Compound 2–3 to the Di-BOC-Silyl-CBZ Pentapeptide (I-6) to Give (E2-4)

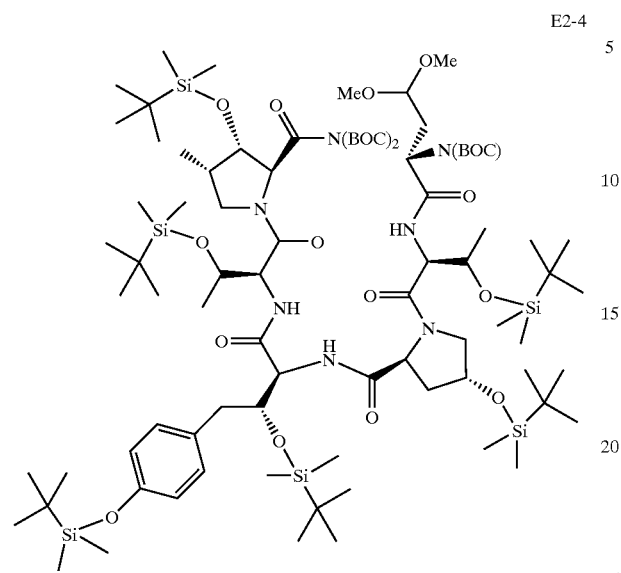

E2-4

Compound I-6 was dissolved in 5 ml of ethanol and added to a slurry of 200 mg of 10% Palladium on charcoal in 10 ml of ethanol (all under an atmosphere of nitrogen). Glacial acetic acid (2 ml) was added and then a hydrogen atmosphere was introduced via a balloon.

Meanwhile, compound E2-3 (0.2 g, 0.76 mmol) was dissolved in 2 ml of tetrahydrofuran (Sure Seal, or freshly distilled from lithium aluminum hydride), 96 mg (0.84 mmol) of N-hydroxysuccinimide was added, followed by 172 mg (0.84 mmol) of dicyclohexylcarbodiimide. The reaction mixture was stirred at room temperature. After approx. 10 minutes, a heavy precipitate was observed. Both reactions were allowed to stir at room temperature approx. 2 to 3 hours and monitored by TLC (25% ethyl acetate/hexane, CAM stain).

After completion of the hydrogenation reaction, the mixture was purged with nitrogen, Celite filter aid was added, stirred, and then filtered through a bed of Celite in a sintered glass funnel. The filtrate was concentrated in vacuo, not letting the bath temperature rise above 45° C. The residue was dissolved in 8 ml of tetrahydrofuran and then approx. 2 ml of triethylamine was added to bring the pH to between 6 to 7. The newly formed active ester from the second reaction was filtered directly into this vessel and enough triethylamine was added to keep the reaction mixture basic (approx. pH 9–10). The reaction was stirred at room temperature overnight. The reaction monitored by TLC (25% ethyl acetate/hexane, CAM stain).

The volatiles were removed in vacuo, chloroform was added to the residue, the organic layer was washed once with 1N hydrochloric acid, once with saturated sodium bicarbonate solution, once more time with 1N hydrochloric acid, and finally once with brine. The solution was dried over sodium sulfate, filtered, and concentrated in vacuo to yield 1 g of E2-4 as a white foam. The material was used without further purification in the subsequent reaction. However, purification can be accomplished using flash silica gel purification chromatography (approx. 100 g of silica, 20% ethyl acetate/hexane). Yield=395 mg (37%) of a white foam. NMR data was consistent with structure E2-4.

MS(FAB)=1726 (M-t-Butyl)

Preparation of the Acyl Hydrazone of Compound E2-4 (E2-5)

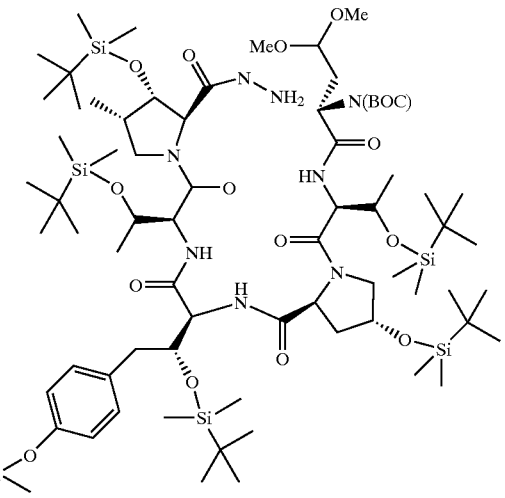

E2-5

A flask was charged with compound E2-4 (374 mg, 0.21 mmol) and 8 ml of tetrahydrofuran. Hydrazine hydrate (13.6 mg, 0.27 mmol, 13.6 μl) was added and stirred at room temperature. The reaction was monitored by TLC (25% ethyl acetate/hexane, CAM stain). After approx. 15 minutes, the volatiles were removed to yield a white foam. Flash silica gel column chromatography (approx. 25 g, 25%→50% ethyl acetate/hexane) yielded 250 mg (75%) of a white foam. NMR data was consistent with the structure E2-5. MS(FAB)=1541(M-t-Butyl)

Cyclization of Compound E2-5 (E2-6)

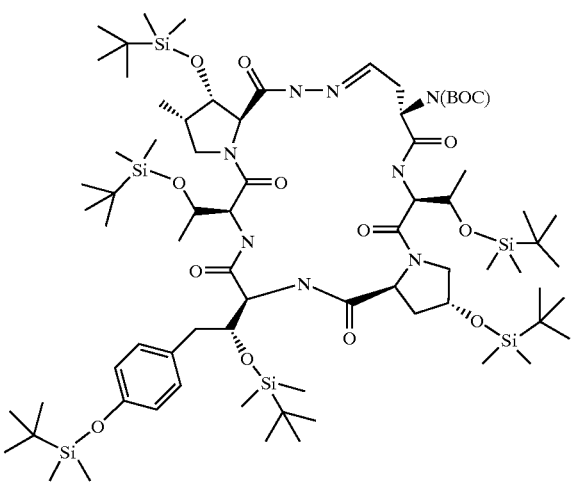

E2-6

Stannous chloride (1.5 g) and solid sodium bicarbonate (400 mg) was suspended in 800 ml of methylene chloride. The mixture was stirred for approx. 15 minutes at room temperature. A solution of compound E2-5 (3.2 g) was added in 100 ml of methylene chloride. The container containing compound E2-5 was rinsed with another 100 ml of solvent and added to the reaction vessel. The reaction was monitored by TLC (40% ethyl acetate/hexane, CAM stain). After approx. 3 hours, the residual solids were filtered off and the filtrate concentrated in vacuo to yield 3 g (100%) of E2-6 as a pale-yellow solid. Any attempt at purification failed due to instability. MS(FAB)=1534 (parent ion)

Borohydride Reduction of Compound E2-6 (E2-7)

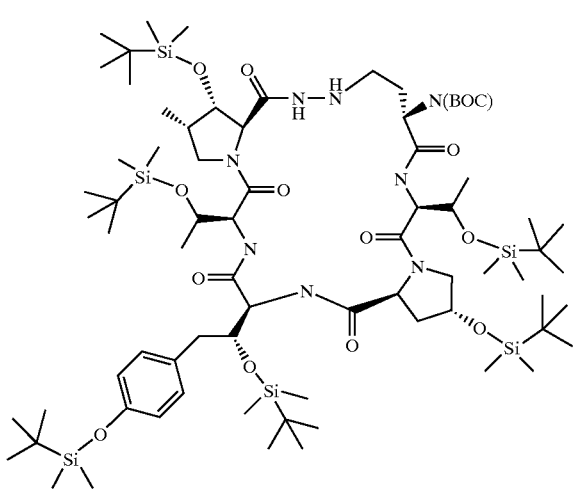

E2-7

Compound E2-6 (6 g, 3.9 mmol) was dissolved in 400 ml of tetrahydrofuran, 425 mg (6.76 mmol) of sodium cyanoborohydride was added followed by 1 ml of glacial acetic acid. The mixture was allowed to stir at room temperature while monitoring by TLC (40% ethyl acetate/hexane, CAM stain). After approx. 2 hours, the volatiles were removed in vacuo, ethyl acetate was added to the residue, washed twice with water, once with brine, dried over sodium sulfate, filtered, and concentrated in vacuo to yield 5.2 g of a white foam. The solid was dissolved in 125 ml of methanol and allowed to stir at room temperature for 6 days. The volatiles were removed in vacuo to yield 4.8 g of a white foam. Flash silica gel column chromatography (approx. 200 g, 25%→35% ethyl acetate/hexane) yielded 2.2 g (37%) of a white foam. NMR data was consistent with the structure E2-7. MS(FAB+)=1537 (M+H)

CBz Protection of Compound E2-7 (E2-8)

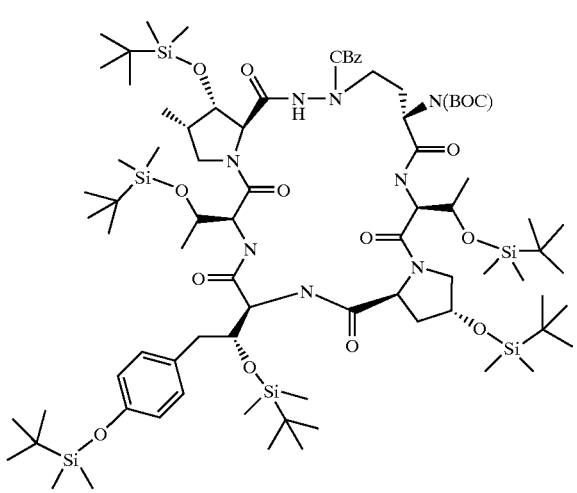

E2-8

A solution of Compound E2-7 (650 mg, 0.4 mmol) in 15 ml of tetrahydrofuran and solid sodium bicarbonate (67 mg) were added to a reaction vessel fitted with rubber septum and stir bar. The solution was flushed with nitrogen and stirred. The mixture was cooled in an ice-bath and benzyl chloroformate (144 mg, 0.8 mmol, 12 µl) was added via syringe. The mixture was stirred cold for approx. 1 hour. The ice-bath was removed and the mixture was allowed to stir at room temperature for approx. 3 hrs. The reaction was monitored by TLC (20% and 40% ethyl acetate/hexane, CAM stain). The volatiles were removed in vacuo. The residue was dissolved in ether, washed twice with water, once with dilute hydrochloric acid quickly, once with saturated sodium bicarbonate solution, once with brine, dried over sodium sulfate, filtered, and concentrated in vacuo to yield 700 mg of a white foam. Flash silica gel column chromatography (35 g of silica, 20% ethyl acetate/hexane) yielded 460 mg (65%) of a white foam. NMR data was consistent with the structure E2-8. MS(FAB)=1670 (parent ion)

Deprotection of Compound E2-8 (E2-9)

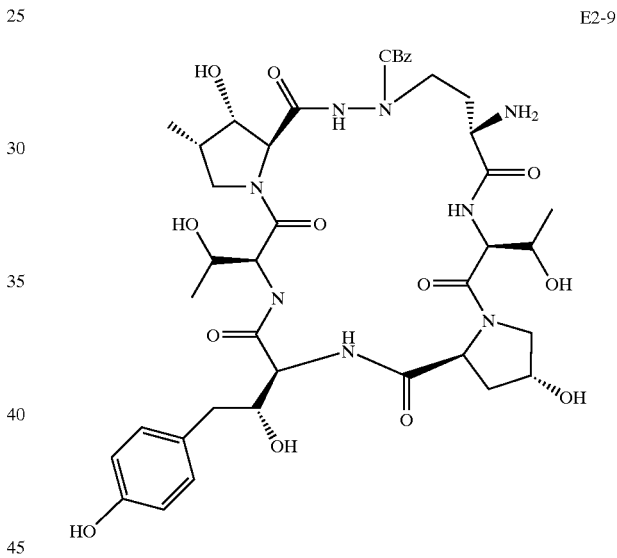

E2-9

Compound E2-8 (1.2 g, 0.72 mmol) was dissolved in cold trifluoroacetic acid (10 ml), placed in an ice-bath and stirred for approx. 1.5 hrs. Cold water (5 ml) was added and stirring continued in the ice-bath for approx. 1 hr. The volatiles were removed in vacuo, 5 ml of tetrahydrofuran and 5 ml of 1N hydrochloric acid was added and stirred overnight at room temperature.

The volatiles were removed in vacuo, toluene was added to the residue and then evaporated. The procedure was repeated two more times in order to remove the excess trifluoroacetic acid. Ether was added to the residue and then sonicated to yield a white solid. The ether was filtered off and the residue rinsed several times with ether. The residue was dried under high vacuum to yield 660 mg (100%) of a white solid. Analysis by RP-HPLC (C-18 Bondapak, 70:20:10 AcN/water/1% TFA, 230 nm) shows material to be 97% pure. NMR data was consistent with the structure E2-9. MS(FAB) 885.5 (M+H)

Preparation of Compound (E2-10(b))

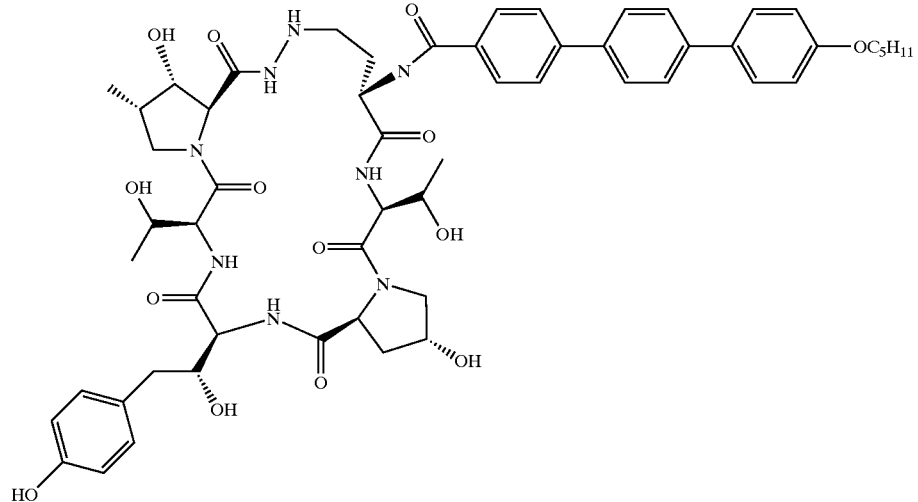

Compound E2-9 (600 mg, 0.68 mmol) was dissolved in 10 ml of dimethylformamide and enough diisopropyl ethylamine added to make the solution basic to pH paper (approx. 0.5 ml). The hydroxybenzotriazole active ester of the terphenyl side chain (388 mg, 0.81 mmol) was added to the reaction vessel and allowed to stir at room temperature overnight. The reaction was monitored by RP-HPLC (60:40 AcN/water, 230 nm).

The solvent was removed in vacuo, and a 1:1 mixture of methanol/acetonitrile was added to the resulting residue, followed by stirring and then filtration. The resulting white solid was suspended in ether, stirred, filtered, and the process repeated. The same procedure was performed using methylene chloride, then finally one time more with ether. The residue was dried under vacuum to yield 735 mg (88%) of a white solid—Compound E2-10(a). MS(FAB)=1227.6 (parent ion)

The white solid (632 mg, 0.5 mmol) was suspended in glacial acetic acid (100 ml) and subjected to catalytic hydrogenation under a balloon of hydrogen, overnight (100 mg of 10% palladium on charcoal). The reaction was monitored by reverse-phase HPLC (C-18 Bondapak, 60:30:10 AcN/water/1% TFA, 230 nm). The reaction vessel was purged with nitrogen, Celite filter aid was added, stirred, filtered through a bed of Celite in a sintered glass funnel, the catalyst was washed with a 1:1:1 mixture of methanol/AcN/water, and the filtrate was concentrated to dryness. Toluene was added and then allowed to evaporate to dryness yielding 440 mg (81%) of a white solid—Compound E2-10(b). MS(FAB)=1093.5 (parent ion)

Alkylation of Deprotected Acyl Hydrazide Nucleus E2-10 (b), where R is Methyl, Ethyl or n-Propyl (E2-11)

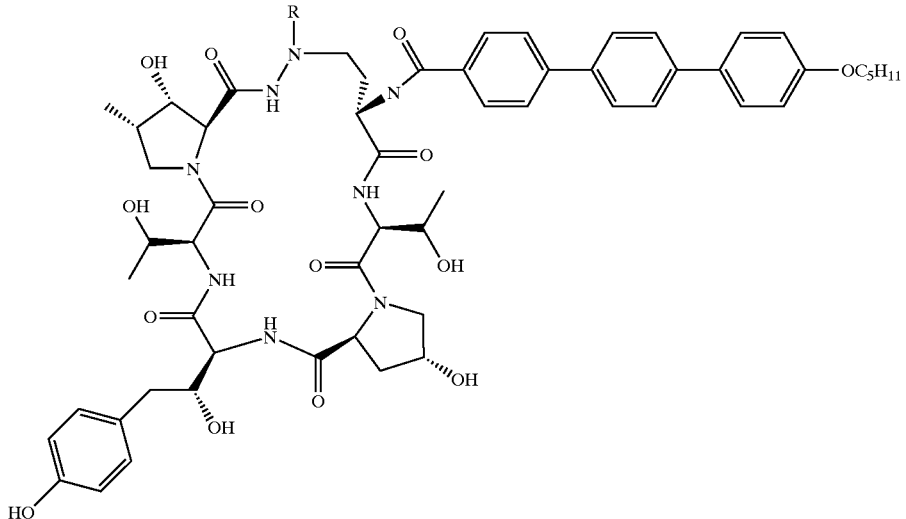

The following procedure illustrates a typical preparation for the alkylations. Compound E2-10(b) (100 mg, 0.086 mmol) was dissolved or suspended in 10 ml of dimethyl formamide. Two equivalents of the corresponding aldehyde (for formaldehyde use 5.2 mg (15 μl)) was added (for acetaldehyde use 7.6 mg (10 μl) and for propionaldehyde use 10 mg (12.5 μl), all are 0.173 mmol), followed by enough glacial acetic acid (approx. 3–4 drops) to make the mixture acidic. Sodium cyanoborohydride (11 mg, 0.173 mmol) was added and the mixture stirred at room temperature, overnight. The reaction was monitored by reverse-phase HPLC (C-18 Bondapak, AcN/water/1% TFA (55:35:10), 280 nm). The reaction was quenched with water to obtain a clear solution and a white gummy material in the bottom of the flask. The solvents were removed in vacuo, acetonitrile was added, filtered, and washed with ether to obtain a white powder (150 mg for methyl, 250 mg for ethyl, and 250 mg for propyl). All alkylated materials were isolated using preparative RP-HPLC (50:40:10 AcN/water/1% HCl, 230 nm for methyl and ethyl and 55:35:10 AcN/water/1% HCl, 230 nm for propyl).

Yield: 64 mg for the methyl derivative E2-11(a) having a MS(FAB)=1107.54 (exact mass)

59 mg for the ethyl derivative E2-11(b) having MS(FAB)=1121.55 (exact mass)

73 mg for the propyl derivative E2-11(c) having a MS(FAB)=1135.57 (exact mass)

Preparation of the Product from Coupling Glycine to Compound E2-7 (E2-12)

sodium sulfate, filtered and concentrated in vacuo to yield 3.3 g (92%) of a light-pink solid. The material had consistent NMR data.

Compound E2-7 (700 mg, 0.45 mmol) was dissolved in 15 ml of tetrahydrofuran. The active ester from above (504 mg, 1.3 mmol) was added, plus a few drops of triethylamine. The mixture was heated near reflux for approx. 4 hours, then cooled to room temperature and allowed to stir overnight. The volatiles were removed in vacuo, ether was added to the residue, washed twice with 1N sodium hydroxide, once with brine, dried over sodium sulfate, filtered, and concentrated in vacuo to yield 1.1 g of a white foam. Flash silica gel column cleanup (20⊠30% ethyl acetate/hexane) yielded 0.75 g (95%) of a white foam. The material had satisfactory NMR data. MS(FAB): 1727.9 (parent ion)

The silyl and BOC protecting groups were removed following the previous procedure for preparation of compound E2-9. The reaction was monitored by RP-HPLC (25:65:10 AcN/water/1% TFA, 230 nm). Yield=490 mg of a white powder The terphenyl side chain was coupled to the above product according to the method for preparation of compound E2-10(b). Reacting amounts: 490 mg of the above compound, 260 mg (0.544 mmol) of the terphenyl active ester, 10 ml of dimethyl formamide, and enough diisopropylethylamine to make the reaction basic. The reaction was followed by RP-HPLC (25:65:10 AcN/water/1% TFA for starting material, 230 nm and 60:30:10 AcN/water/1% TFA for product, 280 nm). The solvent was removed under high

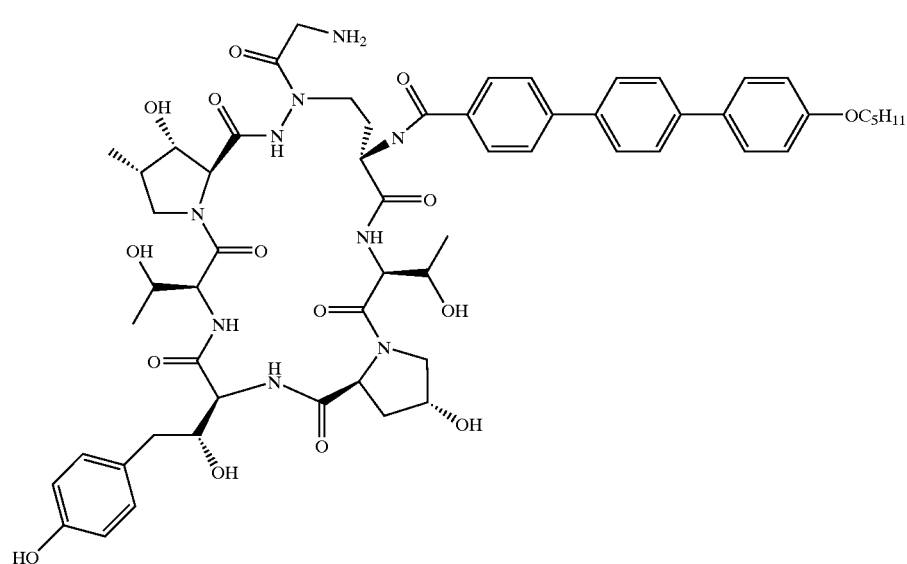

E2-12

CBz-Glycine (2 g, 9.6 mmol) was dissolved in 25 ml of tetrahydrofuran, pentafluorophenol (2.2 g, 11.9 mmol) was added, followed by 1-[3-(dimethylamino)propyl]-3-ethylcarbodiimide hydrochloride (EDAC) (2.2 g, 11.5 mmol). The mixture was stirred at room temperature under nitrogen. The reaction was monitored by TLC (40% ethyl acetate/hexane, UV and CAM stain). After approx. 1 hour, the solvent was removed in vacuo, the residue dissolved in methylene chloride, the organic layer washed once with 1 M sodium bisulfate solution, thrice with 1N sodium hydroxide and finally once with brine. The organic layer was dried over vacuum to yield a white, gummy residue. Trituration from ether (2 washes) yielded 800 mg of a pale-yellow powder.

The above product was subjected to the same hydrogenolysis conditions as that for compound E2-10(a). Reagent amounts: 400 mg of 10% palladium on charcoal, 100 ml of glacial acetic acid. Overnight reaction yielded 600 mg of an off-white solid. The product was isolated using RP-HPLC (AcN/water/1% TFA (50:40:10), 280 nm).

Yield=188 mg of a white powder. NMR data was consistent with structure E2-12. MS(FAB)=1150.54 (exact mass)

Preparation of the Product from Coupling Diaminopropionic Acid to Compound E2-7 (E2-13)

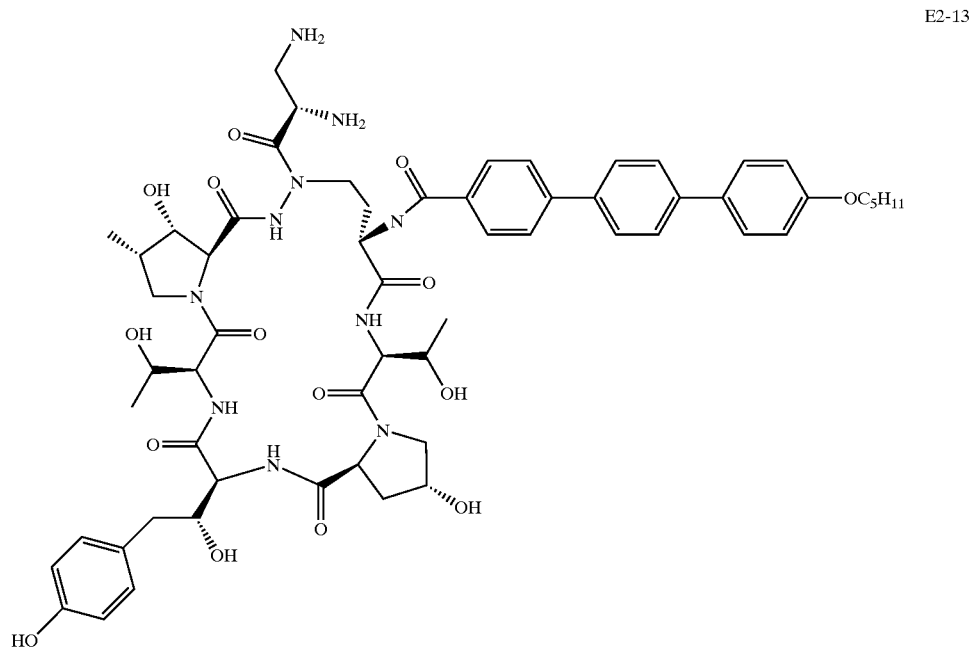

E2-13

Following the above procedure for the preparation of compound E2-12, the active ester of L-di-CBz-diaminopropionic acid was prepared. Reacting stoichiometries were: L-di-CBz-diaminopropionic acid—581 mg (1.56 mmol), pentafluorophenol—344 mg (1.87 mmol), 1-[3-(dimethylamino) propyl]-3-ethylcarbodiimide hydrochloride (EDAC)—360 mg (1.87 mmol), tetrahydrofuran—12 ml. TLC system: chloroform/methanol/glacial acetic acid, 75:25:drop, for starting material; 40% ethyl acetate/hexane, TDM stain for product. Same workup yielded 720 mg (86%) of a white solid. The material had satisfactory NMR data.

Again, following the above procedure for coupling the active ester (710 mg, 1.32 mmol) to compound E2-7 (800 mg, 0.52 mmol) and refluxing for 2 days, standard workup yielded 1.1 g of a white foam. Flash silica gel column chromatography (100 g of silica, 20% ethyl acetate/hexane) yielded 0.56 g (57% yield) of a white foam. MS(FAB)=1891 (parent ion)

The silyl and BOC protecting groups were removed following the previous procedure for preparation of compound E2-9. The reaction was monitored by RP-HPLC (50:40:10 AcN/water/1% TFA, 230 nm). Yield=550 mg The terphenyl side chain was coupled to the above product according to the method for preparation of compound E2-10(b). Reacting amounts: 550 mg of the above compound, 239 mg (0.5 mmol) of the terphenyl active ester, 10 ml of dimethylformamide, and enough diisopropylethylamine to make the reaction basic. The reaction was followed by RP-HPLC (70:20:10 AcN/water/1% TFA for starting material, 230 nm and 40:50:10 AcN/water/1% TFA for product, 280 nm). The solvent was removed under high vacuum to yield a white, gummy residue. Trituration from ether (2 washes) yielded 850 mg of an off-white powder.

The above product was subjected to the same hydrogenolysis conditions as that for compound E2-10(a). Reagent amounts: 400 mg of 10% palladium on charcoal, 100 ml of glacial acetic acid. Overnight reaction yielded 580 mg of an off-white solid. The product was isolated using RP-HPLC (gradient AcN/water/1% TFA (45/45/10→55/10 elution scheme, 280 nm). Two separate products were isolated, both having the same molecular weight. It was never determined what the relative stereochemistries of the two compounds were. The yield of one E2-13 isomer was 76 mg and the yield of the other E2-13 isomer was 116 mg. MS(FAB)=1179.6 (parent ion) for both Table 2 summarizes the activity data for compounds E2-9 through E2-13 in comparison with the comparative semi-synthetic Echinocandin compound C1. The same testing procedures were used as described in Example 1 above.

TABLE 2

| Example No. | Minimal Inhibitory Concentration (MIC) μg/ml | | | |
|---|---|---|---|---|
| | C. albicans | C. parapsilosis | A. fumigatus | Histoplasma capsulatum |
| Comparative C1 | 0.01 | 0.156 | 0.02 | 0.01 |
| E2-10(a) | 0.625 | >20 | 0.625 | 5.0 |
| E2-10(b) | 0.01 | 0.156 | 0.156 | 0.156 |
| E2-11(a) R = methyl TFA salt | 0.005 | 0.156 | 0.039 | 0.78 |
| E2-11(a) R = methyl HCl salt | 0.001 | 0.156 | 0.078 | 0.02 |

TABLE 2-continued

| | Minimal Inhibitory Concentration (MIC) μg/ml | | | |
|---|---|---|---|---|
| Example No. | C. albicans | C. parapsilosis | A. fumigatus | Histoplasma capsulatum |
| E2-11(b) R = ethyl HCl salt | 0.001 | 0.156 | 0.312 | 0.02 |
| E2-11(c) R = n-propyl HCl salt | 0.312 | 1.25 | 0.156 | 0.312 |
| E2-12 | 0.01 | 0.312 | 0.156 | 0.039 |
| E2-13 (isomer 1) | 0.078 | 2.5 | 0.625 | 1.25 |
| E2-13 (isomer 2) | 0.156 | 20 | 1.25 | 10 |

Example 3 further illustrates the insertion of a new unit to yield an analog of an Echinocandin-type compound.

Example 3

CbzNHCH$_2$CH$_2$SH was prepared as described in I. Shinkai, T. Liu, R. Reamer, M. Sletzinger, *Synthesis*, 924, 1980.

N-BOC-O-toluenesulfonyl serine methyl ester was prepared as described in N. A. Sasaki, C. Hashimoto, P. A. Potier, *Tetrahedron Lett.*, 28, 6069–6072, 1987.

Preparation o(R)-2-[(tert-Butoxy-carbonyl)amino]-3-[(2'-N-benzyloxycarbonyl amino)ethanethio]methyl propiolate (E3-1)

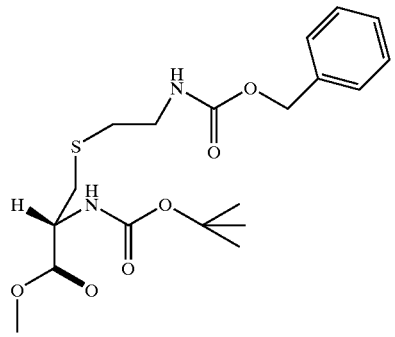

E3-1

Sodium hydride (72 mg, 1.8 mmol, 60% suspension in mineral oil) was triturated with hexanes under a nitrogen atmosphere in a 3-necked round bottomed flask. The flask was placed in a 0° C. bath and a solution of CbzNHCH—$_2$CH$_2$SH (470 mg, 1.87 mmol, 85% pure) in DMF (5 ml) was added. The resulting mixture was stirred at 0° C. for 20 min which resulted in a colorless solution. N-BOC-O-toluenesulfonyl serine methyl ester (671 mg, 1.8 mmol) was added as a solid and washed into the flask with an additional 2 ml of DMF. The resulting mixture was stirred at 0° C. for 3 hours then poured into water and extracted twice with ethyl acetate. The combined organic extracts were washed with water, 1N sodium hydroxide solution, water, and brine, then dried over MgSO$_4$ and concentrated in vacuo to give 900 mg of an oil. Radial chromatography eluting with 25%→50% ethyl acetate in hexanes gave 570 mg 76% of the desired (R)-2-[(tert-Butoxy-carbonyl)amino]-3-[(2'-N-benzyloxycarbonyl amino)ethanethio]methyl propiolate.

Anal. calculated for C$_{19}$H$_{28}$N$_2$O$_6$S, C: 55.32, H: 6.84, N: 6.79; Found C: 55.26, H: 6.95, N: 6.94. [α]$_D$–1.9° (c=10).

Preparation of (R)-2-[(tert-Butoxycarbonyl)amino]-3-[(2'-N-benzyloxycarbonyl amino)ethanethio]propiolic acid. (E3-2)

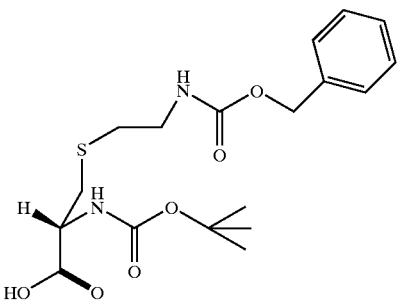

E3-2

Compound E3-1 (520 mg, 1.26 mmol) in dioxane (3 ml) was treated with 0.5M LiOH solution (3 ml) and stirred at room temperature overnight. The dioxane was removed in vacuo and the residue partitioned between 1N hydrochloric acid solution and ethyl acetate. The organic extract was washed with brine, dried over MgSO$_4$ and concentrated in vacuo to give 500 mg of a colorless oil corresponding to compound E3-2. Anal. calculated for C$_{18}$H$_{26}$N$_2$O$_6$S+ 0.4H$_2$O, C, 53.29; H, 6.65; N, 6.90. Found C, 53.61; H, 6.82; N, 6.85. [α]$_D$–0.9° (c=10). MS: (m+1) 399.

Preparation of (R)-2-[(tert-Butoxycarbonyl)amino]-3-[(2'-N-benzyloxycarbonyl amino)ethanesulfonyl]propiolic acid (E3-3)

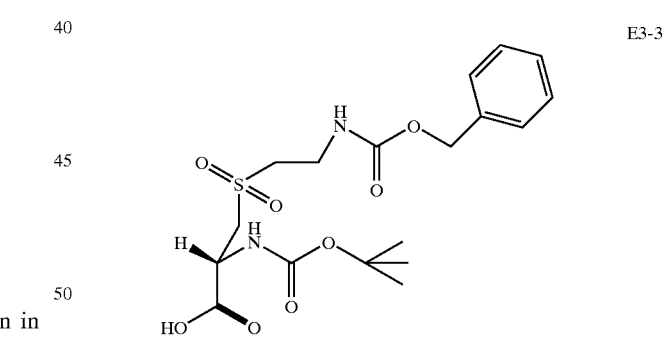

E3-3

Compound E3-2 (0.95 g, 2.38 mmol) was dissolved in MeOH (15 ml) and cooled to 0° C. A solution of Oxone® (1.77 g, 5.7 mmol) in water (15 ml) was added and the resulting mixture stirred at 0° C. for 1 hour then at room temperature overnight. The MeOH was removed in vacuo and the residue partitioned between ethyl acetate and water. The aqueous phase was extracted several more times with ethyl acetate. The combined organic extracts were washed with brine, dried over MgSO$_4$ and concentrated in vacuo to give 800 mg (78%) of a colorless foam corresponding to compound E3-3. Anal. calculated for C$_{18}$H$_{26}$N$_2$O$_8$S, C, 50.22; H, 6.09; N, 6.51. Found, C: 50.13; H, 5.86; N, 6.45. [α]$_D$–7° (c=10). MS: (m+1) 431.

Preparation of Compound E3-4

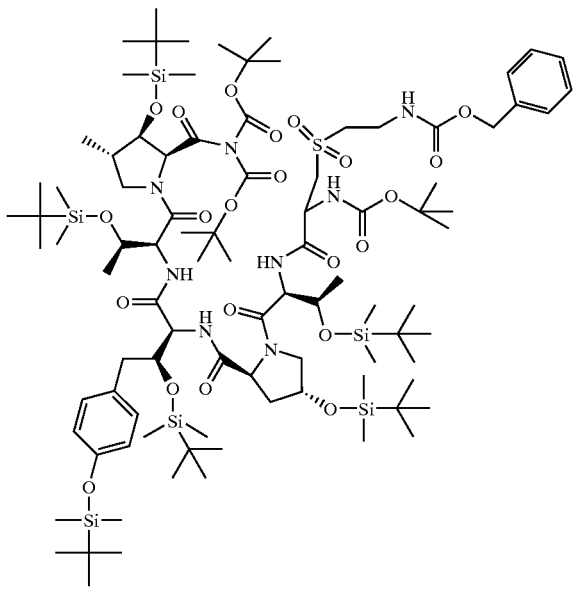

To a solution of Compound E3-3(160 mg, 0.37 mmol) and N-hydroxysuccinimide (43 mg, 0.37 mmol) in dry THF (5 ml) was added dicyclohexylcarbodiimide (76 mg, 0.37 mmol) and an additional 2 ml of THF. The mixture was stirred at room temperature for 3 hours then cooled to 0° C. to help precipitate dicyclohexyl urea. In the meantime, the DiBOC CBZ silyl pentapeptide I-6(565 mg, 0.337 mmol) was dissolved in absolute ethanol (10 ml) and glacial acetic acid (95 ml), degassed and then 10% Pd/C (160 mg) was added to the mixture. The mixture was stirred under an atmosphere of $H_2$ (balloon pressure) for 3 hrs. The catalyst was removed by filtration and the filtrate concentrated in vacuo to a thick oil. THF (10 ml) and acetic acid (1 ml) were added and the solvents again removed in vacuo to remove all residual ethanol. The above prepared NHS active ester of compound E3-3 was filtered directly into the flask containing the deblocked pentapeptide through a sintered glass funnel, washing the precipitated DCU with an additional 3 ml of THF. The resulting solution was made basic to Litmus paper by dropwise addition of triethyl amine. The mixture was stirred at room temperature for an additional 3 hours, then diluted with ethyl acetate, washed with saturated sodium bicarbonate solution, and brine, then dried over $MgSO_4$ and concentrated in vacuo. Flash chromatography eluting with 7:2:1 hexane:ethyl acetate:methylene chloride gave the desired coupling product E3-4 as a mixture of isomers. The less polar isomer yielded 140 mg having a MS=1950.9 (m+). Mixed fractions: 224 mg. The more polar isomer yielded 155 mg having a MS=1951.9 (m+1). Total yield 519 mg, 78%.

This reaction was repeated on a 0.6 mmol scale to give 400 mg of the desired product as a mixture of isomers. Anal. calculated for $C_{93}H_{168}N_8O_{22}SSi_6$, C, 57.25; H, 8.68; N, 5.75. Found C, 57.55; H, 8.63; N, 5.79.

(The stereocenter of acid E3-3 racemized in the coupling reaction.)

Preparation of Compound E3-5

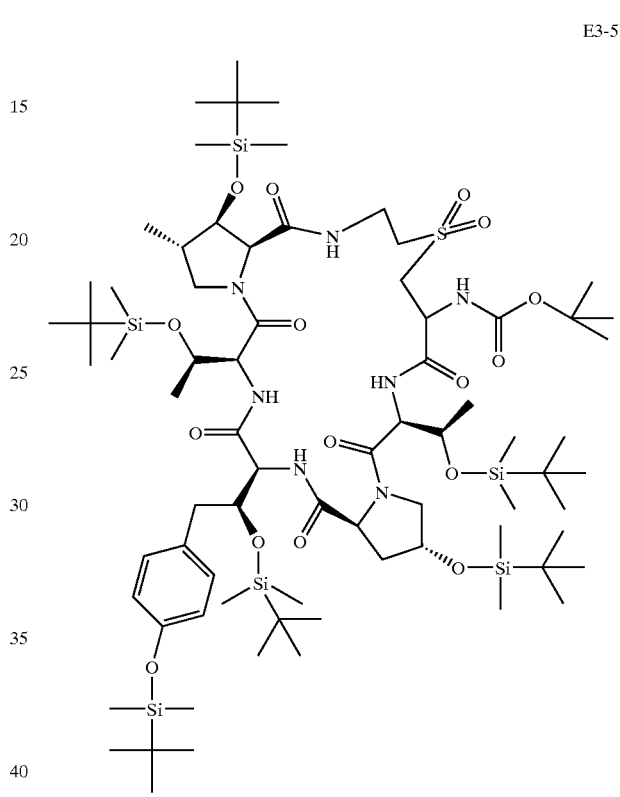

A solution of compound E3-4 (390 mg, 0.2 mmol, mixture of diastereomers) in absolute ethanol (10 ml) and glacial acetic acid (10 ml) was degassed and then treated with 10% Pd/C (390 mg). The mixture was stirred under an atmosphere of $H_2$ (balloon pressure) for 2 hrs. The catalyst was removed by filtration through Celite and the filtrate concentrated in vacuo being careful to leave some acetic acid present. The residue was diluted with diethyl ether (175 ml) and triethylamine was added until the mixture was basic to Litmus paper (approximately 1 ml was required). The resulting solution was stirred at room temperature overnight, then washed with 0.1N hydrochloric acid solution, brine, dried over $MgSO_4$, and concentrated in vacuo to give a foam. Flash chromatography on silica gel eluted with 30% ethyl acetate in hexanes gave the desired ring closed material E3-5. The less polar isomer yielded 105 mg of a foam having a MS: (m+) 1599.9. The more polar isomer yielded 110 mg of a foam having a MS=1599.8(m+). Total yield was 215 mg, 67%.

Preparation of Compound E3-6

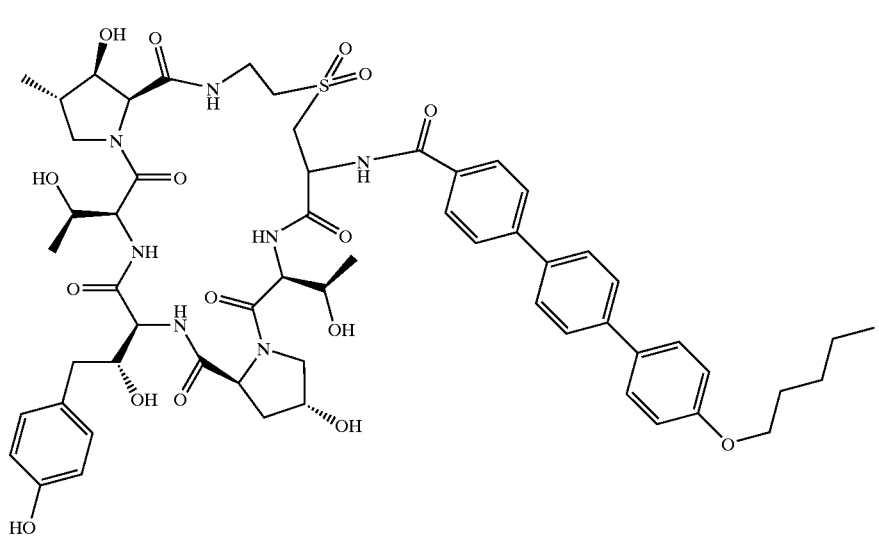

E3-6

The more polar isomer of compound E3-5 (160 mg, 0.1 mmol) was dissolved in trifluoroacetic acid (5 ml) that had been cooled to 0° C. After 30 min water (0.5 ml) was added and the mixture stirred an additional 30 min at 0° C. The mixture was concentrated in vacuo, the residue dissolved in THF and concentrated in vacuo. The residue was dissolved in THF (3 ml), 1N hydrochloric acid solution (1 ml) was added, and the mixture placed in the refrigerator overnight. The solvent removed in vacuo then additional THF was added and the mixture re-concentrated to azeotrope off the water. This treatment provided a white solid. This white solid was dissolved in DMF (5 ml) and the terphenylhydroxybenzotriazole active ester (58 mg, 0.12 mmol) was added followed by triethylamine (60 □1, 0.4 mmol). The resulting solution was stirred at room temperature overnight, then the solvent was removed in vacuo. The residue was purified by preparative RP-HPLC (step gradient 50%–70% AcN in water over 45 min). The major peak was analyzed by HPLC (C-18 u-bondpak column, 60% AcN, 0.1% TFA in water) and the fractions containing the material which eluted at 4 min were combined and freeze dried to give 65 mg (56% yield) of E3-6 as a white powder having a MS=1156.6 (m+).

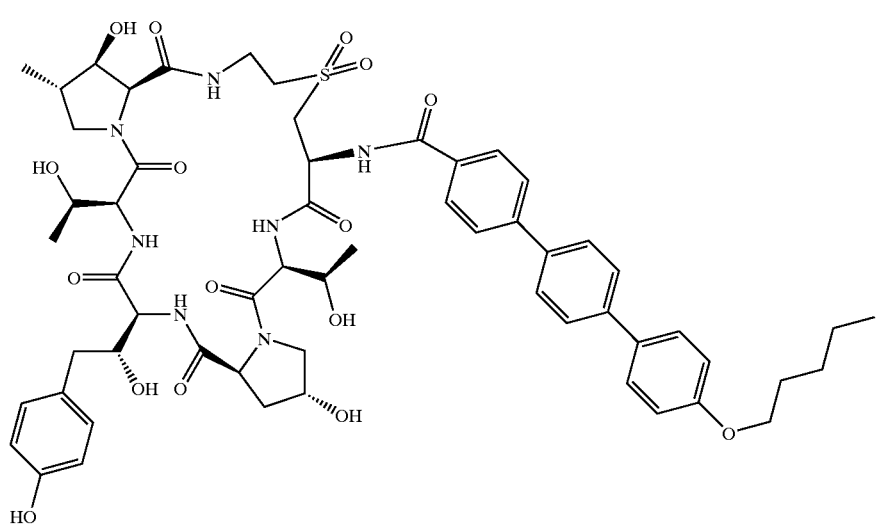

E3-7

In analogous fashion the less polar isomer was converted to E3-7 (material eluted in 7 min under the above described analytical conditions) to give 13 mg (11% yield) of the desired E3-7.

FAB MS (M), calculated for $C_{58}H_{74}N_7O_{16}S$ 1156.4913. found=1156.4924.

The following set of examples illustrate the further cleavage of the linear pentapeptide to a tetrapeptide and subsequent insertion of new units onto the linear peptide chain prior to closing.

Example 4

E4-1

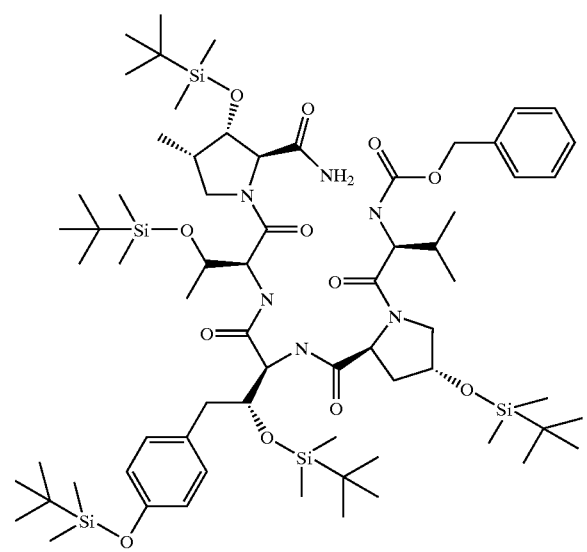

E4-2

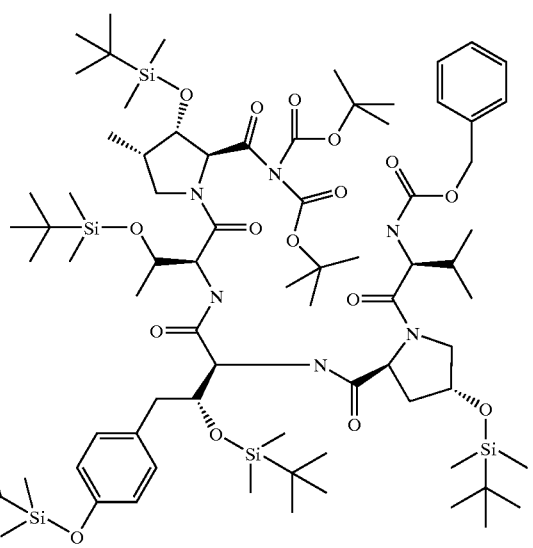

To a solution of Compound E4-1 (700 mg, 0.51 mmol) in anhydrous THF (0.6 ml) and acetonitrile (4 ml) was added N-t-Boc anhydride (0.24 ml, 1.03 mmol) and dimethylaminopyridine (7 mg, 0.05 mmol). The solution was stirred for 3 hrs. Following removal of the solvents in vacuo, flash chromatography (eluting with 17% EtOAc/hexane) gave 307 mg of product, 38% yield. The $^1$H NMR (300 MHz) spectrum was consistent with the structure E4-2. FAB MS (M$^+$ of free base)=1556.

To a solution of Compound I-7 (732 mg, 1.1 mmol) in anhydrous THF (25 ml) was added PyBOP® (572 mg, 1.1 mmol), N-Cbz-L-valine (304 mg, 1.21 mmol), diisopropylethyl amine (0.57 ml, 3.3 mmol), and anhydrous DMF (1.0 ml) to dissolve remaining solids. The solution was stirred at room temperature for 2 hrs. followed by removal of the solvents in vacuo. The residue was dissolved in anhydrous THF (40 ml), followed by addition of t-Butyldimethyl-silylchloride (1.66 g, 11.0 mmol) and imidazole (750 mg, 11.0 mmol). The solution was stirred at room temperature for 18 hrs. The reaction was concentrated in vacuo and the residue was dissolved in Et$_2$O, washed twice with 0.1N HCl, dried over MgSO$_4$, and the solvent removed in vacuo. Flash chromatography (eluting with 35% EtOAc/hexane) gave 690 mg of product, 46% yield. The $^1$H NMR (300 MHz) spectrum was consistent with the structure E4-1. FAB MS (M+)=1356.

E4-3

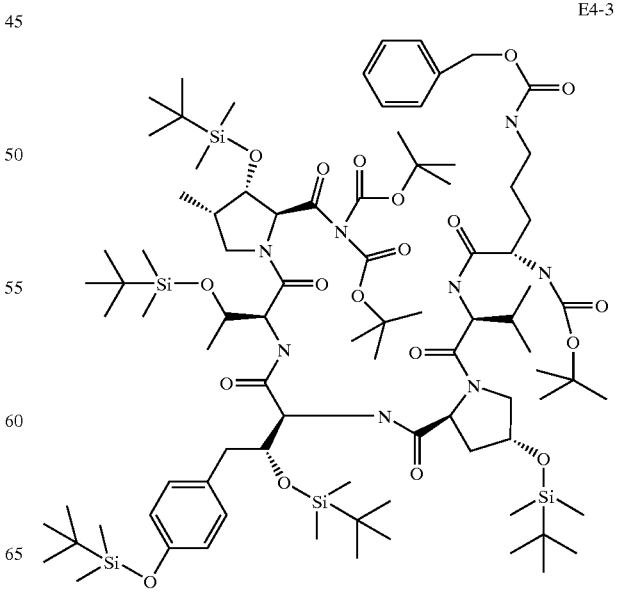

To a solution of 5% Pd/C (150 mg) in EtOH (15 ml) and AcOH (15 ml) under an $N_2$ atmosphere was added Compound E4-2 (307 mg, 0.20 mmol). The solution was purged/filled with $H_2$ (×8) and subjected to constant $H_2$ pressure for 2.0 hrs., then filtered over Celite to remove the catalyst. The solution was concentrated in vacuo to remove solvents, the residue dissolved in anhydrous THF (30 ml), followed by addition of α-N-t-Boc-γ-N-Cbz-L-ornithine (80 mg, 0.22 mmol), PyBOP® (103 mg, 0.20 mmol), and diisopropylethyl amine (0.10 ml, 0.59 mmol). The reaction was stirred at room temperature for 18 hrs., followed by removal of the solvent in vacuo. Flash chromatography (eluting with 30% EtOAc/hexane) gave 284 mg of a white solid, 81% yield. The $^1$H NMR (300 MHz) spectrum was consistent with the structure E4-3. FAB MS ($M^+$ of free base)= 1771.

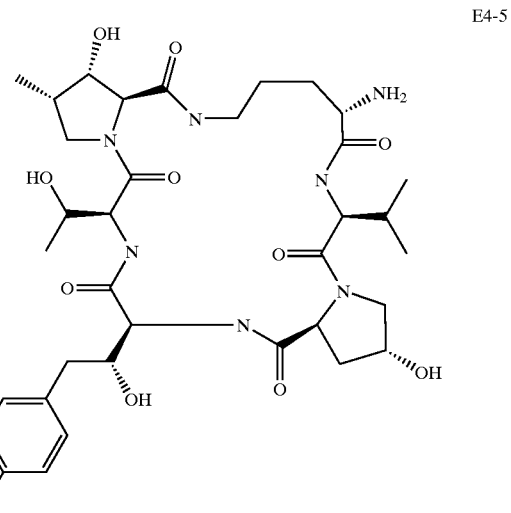

E4-5

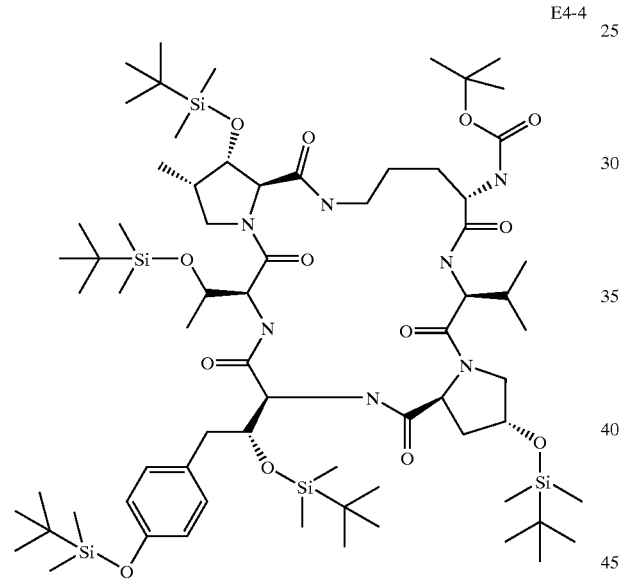

E4-4

A solution of Compound E4-4 (93 mg, 0.07 mmol) in ice cold TFA (2 ml) was placed in a 0° C. freezer for 2 hrs., followed by addition of ice cold water (2 ml) and was then stirred in an ice bath for 2 hrs. The solution was concentrated in vacuo to yield 66 mg white solids, which were dissolved in THF (1.5 ml) and HCl (1.5 ml, 1.0N) and stirred at room temperature for 16 hrs. Toluene was added and the solution was concentrated in vacuo three times to assist in removal of TFA, giving 44.5 mg of an off-white solid, 91% yield. The $^1$H NMR (300 MHz) spectrum was consistent with the structure E4-5. FAB MS ($M^+$ of free base)=748.

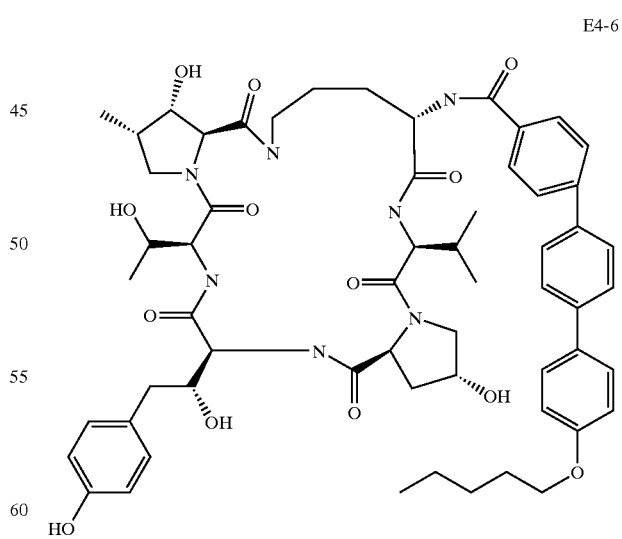

E4-6

To an $N_2$ purged solution of Compound E4-3 (279 mg, 0.16 mmol) in EtOH (13 ml) and AcOH (12 ml) was added 5% Pd/C (150 mg). The reaction was purged/filled with $H_2$ (×10) and left under constant $H_2$ pressure for 2 hrs., followed by removal of the catalyst by filtration over Celite and removal of solvents in vacuo. The resulting oil was dissolved in $Et_2O$ (75 ml) followed by addition of triethylamine (5 ml, 35.9 mmol). After 18 hrs., the reaction was concentrated in vacuo, and flash chromatography (eluting with 34% EtOAc/hexane) gave 96 mg of product, 43% yield. The $^1$H NMR (300 MHz) spectrum was consistent with the structure E4-4. FAB MS ($M^+$ of free base)=1420.

To a solution of Compound E4-5 (44 mg, 0.06 mmol) in anhydrous DMF (2 ml), was added diisopropylethyl amine (0.03 ml, 0.18 mmol) and the hydroxybenzotriazole active ester of the terphenyl side chain (34 mg, 0.07 mmol). The solution was stirred at room temperature for 40 hrs. Solvent was removed in vacuo and the residue was treated with Et₂O (10 ml), sonicated, and a brown solid was isolated by filtration. RP-HPLC (eluting with 30–70% ACN/0.1% TFA/H₂O) and freeze drying gave 18.7 mg of a white solid, 29% yield. The ¹H NMR (300 MHz) spectrum was consistent with the structure E4-6. FAB MS (M⁺ of free base)=1090.

Example 5

Example 5 further exemplifies the insertion of new units onto a tetrapeptide chain followed by ring closure to produce a new cyclic peptide Echinocandin-type structure.

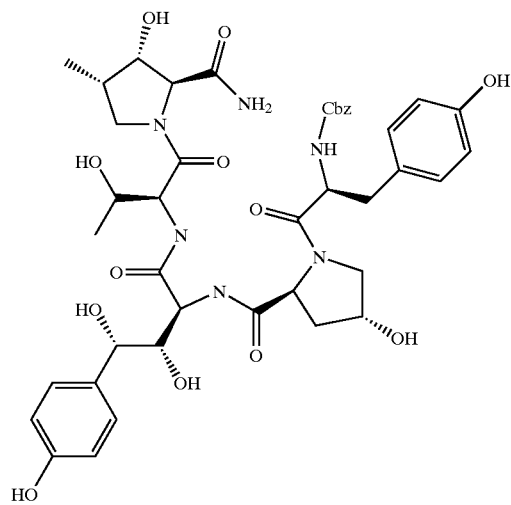

E5-1 removal of the solvents in vacuo. Used directly in the next reaction.

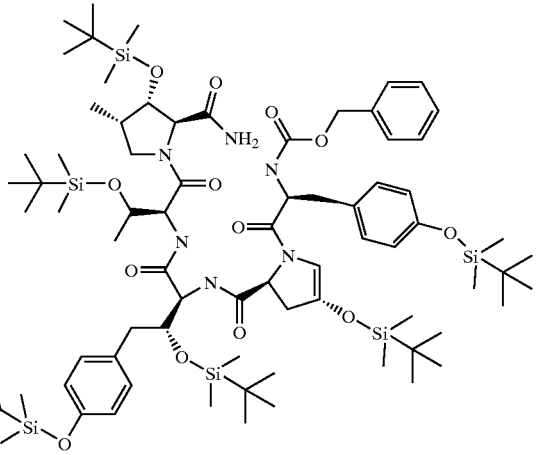

E5-2

The above residue E5-1 was dissolved in anhydrous DMF (10 ml), followed by addition of t-Bu-dimethylsilyl chloride (1.90 g, 12.6 mmol) and imidazole (860 mg, 12.6 mmol) and the solution was stirred at room temperature for 18 hrs. The reaction was concentrated in vacuo and the residue was dissolved in Et₂O, washed twice with cold 0.1N HCl, once with H₂O, 10% aq. sodium bicarbonate, brine and dried over MgSO₄, filtered and the solvent removed in vacuo to give 2.0 g crude oil. Purified by radial chromatography (eluting with 35% EtOAc/hexanes) to give 700 mg (43% yield) of product. The ¹H NMR (300 MHz) spectrum was consistent with the structure E5-2. FAB MS (M⁺)=1534.

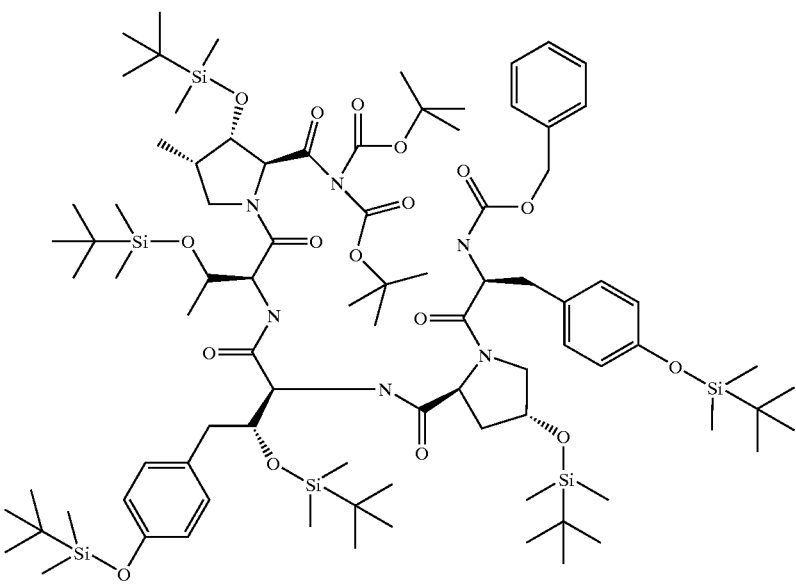

E5-3

To a solution of tetrapeptide I-7 (700 mg, 1.05 mmol) in anhydrous THF (20 ml) was added PyBOP® (547 mg, 1.05 mmol), N-Cbz-L-tyrosine (364 mg, 1.16 mmol), N,N-diisopropylethylamine (0.55 ml, 3.15 mmol). The solution was stirred at room temperature for 3 hrs. followed by To a solution of Compound E5-2 (700 mg, 0.46 mmol) in anhydrous THF (10 ml) was added N-t-Boc anhydride (0.41 ml, 1.78 mmol) in portions and dimethylaminopyridine (7 mg, 0.05 mmol), and the solution was stirred for 3 hrs. at ambient temperature. Following removal of solvents in vacuo, purification by radial chromatography (eluting with 20% EtOAc/hexanes) gave 460 mg of product, 58% yield. The $^1$H NMR (300 MHz) spectrum was consistent with the structure E5-3. FAB MS (M$^+$ of free base)=1735.

(30 ml), followed by addition of α-N-t-Boc-γ-N-Cbz-L-ornithine-N-hydroxysuccinimide ester (172 mg, 0.37 mmol), and triethylamine to pH 8 (≈5 ml). The reaction was stirred at room temperature for 3 hrs. Diluted the reaction

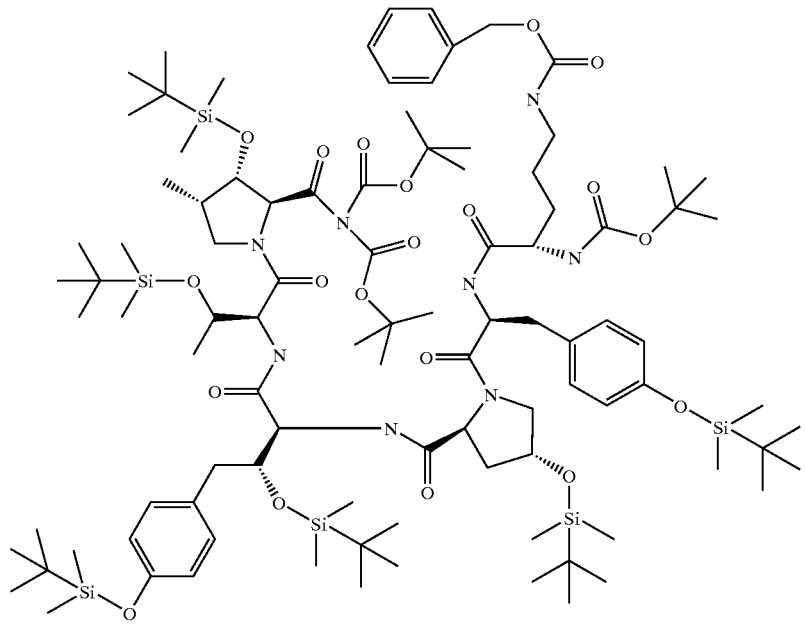

E5-4

To a solution of 10% Pd/C (270 mg) in EtOH (10 ml) and AcOH (10 ml) under an N$_2$ atmosphere was added Compound E5-3 (460 mg, 0.27 mmol). The solution was purged/filled with H$_2$ (×4) and subjected to constant H$_2$ pressure for 2.0 hrs. at ambient temperature, then filtered over Celite to remove catalyst. The solution was concentrated in vacuo to remove solvents, the residue dissolved in anhydrous THF with ether and washed with saturated sodium bicarbonate, 0.1N HCl, saturated sodium bicarbonate, and dried over magnesium sulfate. Filtered and concentrated in vacuo. Radial chromatography (eluting with 30% EtOAc/hexanes) gave 280 mg of a white solid, 54% yield. The $^1$H NMR (300 MHz) spectrum was consistent with the structure E5-4. FAB MS (M$^+$ of free base)=1949.

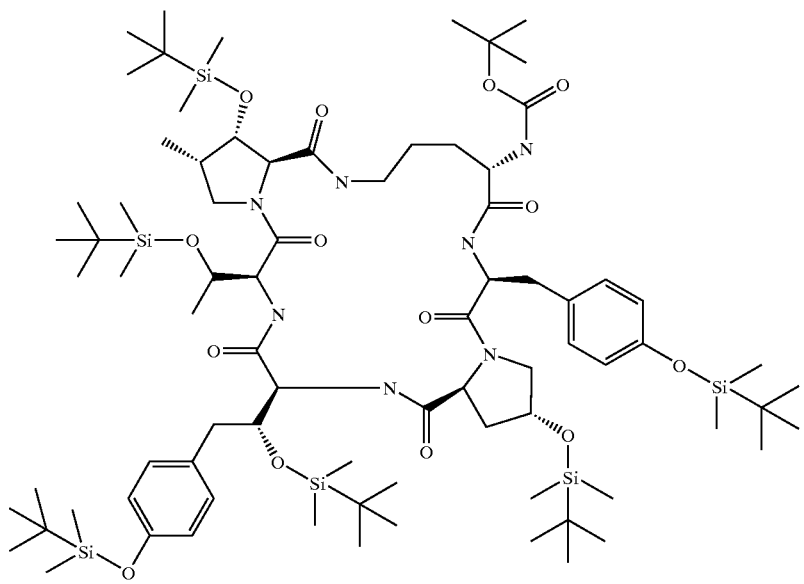

E5-5

To an N₂ purged solution of Compound E5-4 (280 mg, 0.14 mmol) in EtOH (10 ml) and AcOH (5 ml) was added 10% Pd/C (200 mg). The reaction was purged/filled with H₂ (×4) and left under constant H₂ pressure for 2 hrs., followed by removal of the catalyst by filtration over Celite. The resulting oil was dissolved in Et₂O (10 ml) followed by addition of triethylamine (4 ml, 28.7 mmol). After 18 hrs., the reaction was concentrated in vacuo, and purified by radial chromatography (eluting with 40% EtOAc/hexanes) gave 130 mg of product, 57% yield. The ¹H NMR (300 MHz) spectrum was consistent with the structure E5-5. FAB MS (M⁺ of free base)=1597.

E5-6

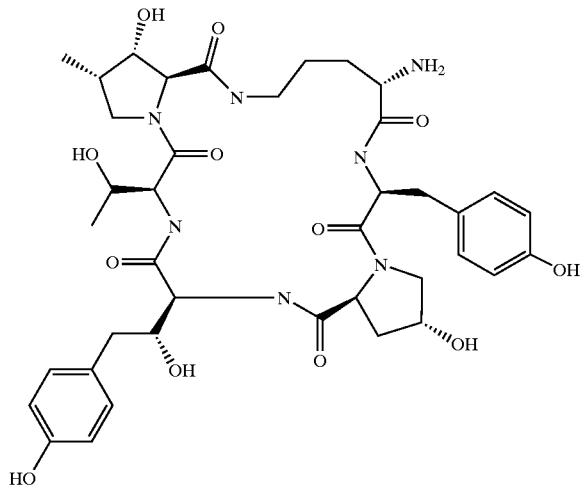

A solution of Compound E5-5 (128 mg, 0.08 mmol) in ice cold TFA (2 ml) was placed in 0° C. freezer for 2 hrs., followed by addition of ice cold water (2 ml) and was then stirred in an ice bath for 2 hrs. The solution was concentrated in vacuo, then dissolved in THF (1.5 ml) and 1N HCl (1.5 ml) and stirred at room temperature for 16 hrs. Toluene was added and the solution was concentrated in vacuo three times, giving 70 mg of a dihydrochloride white solid, 100% yield. The ¹H NMR (300 MHz) spectrum was consistent with the structure E5-6. FAB MS calculated for M+H $C_{39}H_{54}N_7O_{12}$=812.3830. found=812.3837.

E5-7

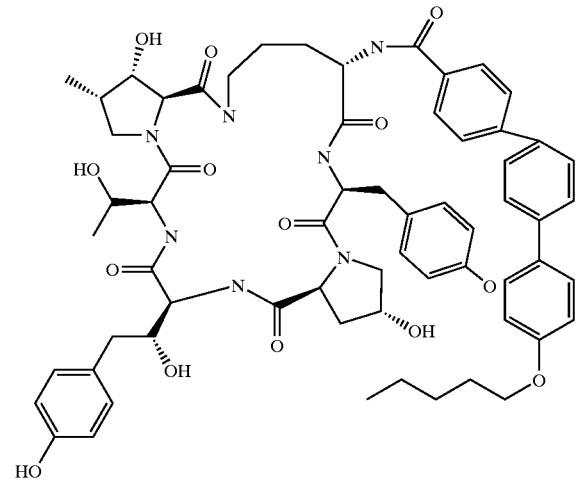

To a solution of Compound E5-6 (65 mg, 0.08 mmol) in anhydrous DMF (5 ml), was added N,N-diisopropylethyl-amine (2.0 ml, 11.5 mmol) and the hydroxybenzotriazole active ester of the terphenyl side chain (50 mg, 0.11 mmol), and the solution was stirred at room temperature for 18 hrs. Solvent was removed in vacuo and the residue was treated with Et₂O (10 ml), sonicated, and a beige solid was isolated. The methanol soluble portion was purified by RP HPLC (Waters Bondapak C-18, eluting with 58% AcN/0.1% TFA/H₂O at a flow of 20 ml/min) and freeze drying gave 35 mg of a white solid, 38% yield. The ¹H NMR (300 MHz) spectrum was consistent with the structure E5-7. FAB MS calculated for M+H $C_{63}H_{76}N_7O_{14}$=1154.5450. found=1154.5458.

Example 6 illustrates the introduction of a water solubilizing group onto the tetrapeptide intermediate prior to cyclization.

Example 6

E6-1

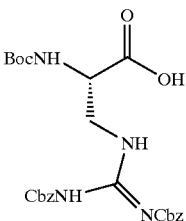

N-α-Boc-L-α,β-diaminopropionic acid (0.5 g, 2.45 mmol)(available from Bachem) and 1,3-Bis(benzyloxycarbonyl)-2-methyl-2-thiopseudourea (0.88 g, 2.45 mmol) were combined in 15 ml of anhydrous DMF. Triethylamine (1.0 ml, 7.3 mmol) was added and stirred for 3 days at ambient temperature. The reaction was diluted with 100 ml of 0.1 N NaOH and extracted into ether. The aqueous layer was then acidified with cold saturated citric acid and extracted with ethyl acetate (3×200 ml). The combined organics were dried over MgSO₄, filtered and concentrated to a quantitative yield of a thick colorless oil. The ¹H NMR (300 MHz) spectrum was consistent with structure E6-1. FD MS (M⁺ of free base)=515.

E6-2

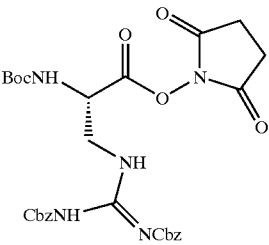

To the above acid E6-1 (310 mg, 0.60 mmol) in anhydrous THF (10 ml) was added N-hydroxysuccinimide (69 mg, 0.60 mmol) and DCC (123 mg, 0.60 mmol). A white precipitate began to form after about 1 hr. The reaction was allowed to stir overnight at ambient temperature. The reaction was filtered and the crude solution used directly in the next coupling.

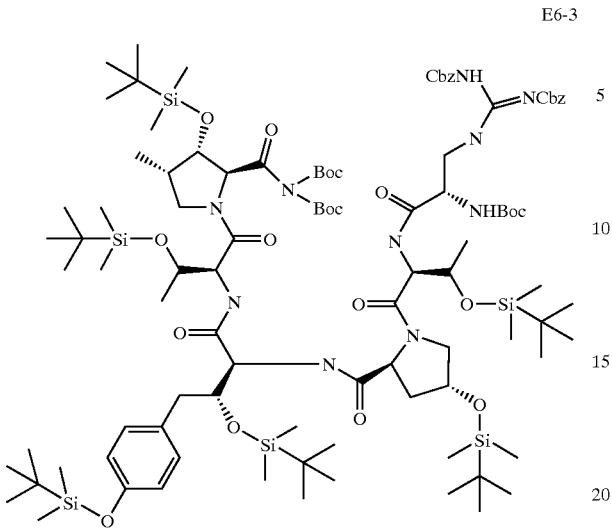

E6-3

To a solution of the above activated ester E6-2 (366 mg, 0.60 mmol) in anhydrous THF (10 ml) and ether (10 ml) was added Compound E5-3 (920 mg, 0.60 mmol) and triethylamine (3 ml). The solution was allowed to stir overnight (18 hrs.) at ambient temperature. The reaction was diluted with ether and washed with saturated sodium bicarbonate (1×250 ml), 0.1 N HCl (1×250 ml), saturated sodium bicarbonate (1×250 ml), dried over magnesium sulfate, filtered and concentrated to 1.0 g crude white solid. The product was purified by radial chromatography (eluting with 30/70 ethyl acetate/hexanes) to give 550 mg (46% yield) of a white solid. The $^1$H NMR (300 MHz) spectrum was consistent with structure E6-3. FAB MS (M$^+$ of free base)=2036.

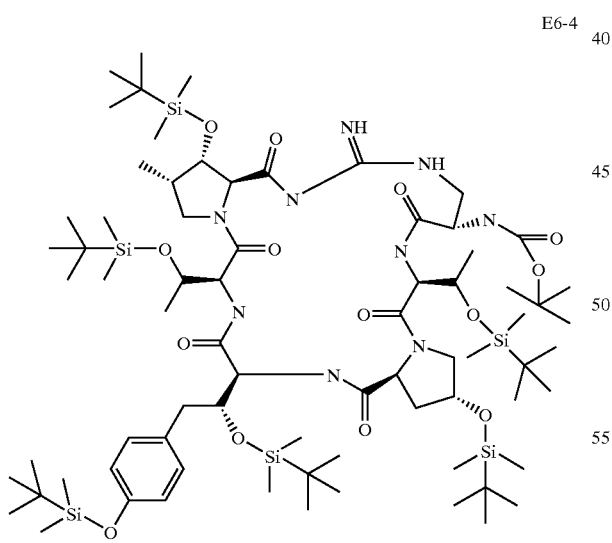

E6-4

To a solution of 5% Pd/C (150 mg) in EtOH (15 ml) and AcOH (15 ml) under an N$_2$ atmosphere was added Compound E6-3 (550 mg, 0.27 mmol). The solution was purged/filled with H$_2$ (×4) and subjected to constant H$_2$ pressure for 2.0 hrs., then filtered over Celite to remove the catalyst. The solution was concentrated in vacuo to remove the solvents, the residue dissolved in acetonitrile (10 ml) and ether (3 ml), followed by addition of 2 ml of triethylamine. The mixture was sonicated for 4 hours and the temperature allowed to reach 40° C. The reaction mixture was concentrated and purified by radial chromatography (eluting with 40/60 ethyl acetate/hexanes) to give 57 mg of the desired compound (14% yield). The $^1$H NMR (300 MHz) spectrum was consistent with the structure E6-4. FAB MS (M$^+$ of free base)= 1549.

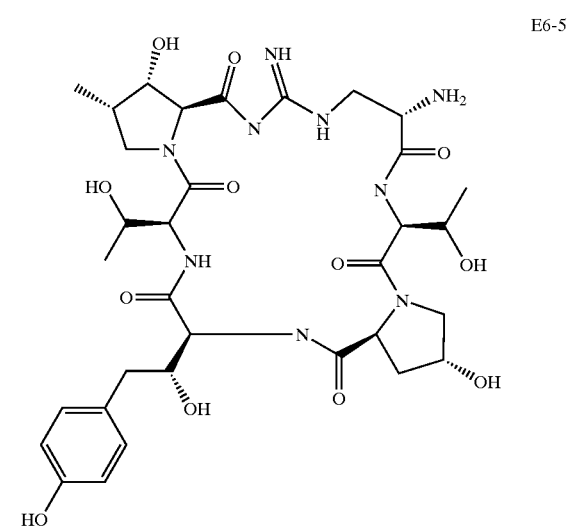

E6-5

To the above compound E6-4 (77 mg, 0.05 mmol) was added 3 ml of neat trifluoroacetic acid while cooling to 0° C. After 45 minutes, 0.5 ml of water was added while maintaining the reaction at 0° C. After 30 minutes, the mixture was concentrated to a colorless oil. To this oil was added 2 ml of THF and 2 ml of 1N HCl and refrigerated overnight. Toluene was stripped from the mixture to give a quantitative yield of the free amine as the trihydrochloride salt. The $^1$H NMR (300 MHz) spectrum was consistent with the structure E6-5. FAB MS (M$^+$ of free base)=764.

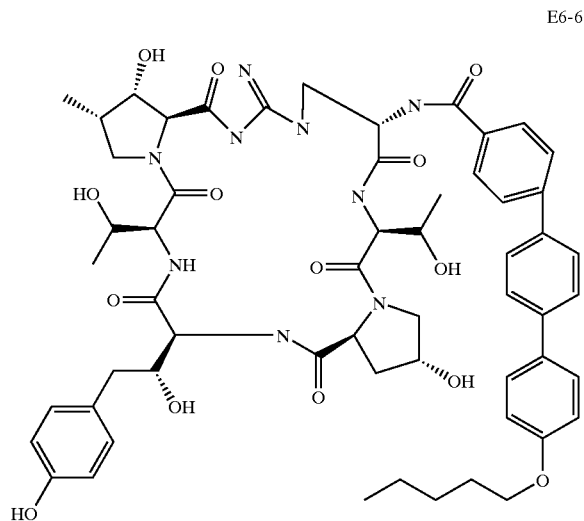

E6-6

To a solution of Compound E6-5 (50 mg, 0.06 mmol) in anhydrous DMF (5 ml), was added N,N-diisopropylethylamine (2 ml) and the hydroxybenzotriazole active ester of the terphenyl side chain (44 mg, 0.09 mmol), and the solution was stirred at room temperature for 18 hrs. The solvent was removed in vacuo and the residue was triturated with a mixture of acetonitrile and ether. The solid was dried to 25 mg of a crude white solid. The product was purified by RP HPLC on a Waters Bondapak C-18 column eluting with 55% AcN/0.1% TFA/H$_2$O at a flow of 20 ml/min. The appropriate fractions were freeze dried to give 10.0 mg of a white solid, 18% yield. The $^1$H NMR (300 MHz) spectrum was consistent with the structure E6-6. FAB MS calculated for (M+H)C$_{57}$H$_{72}$N$_9$O$_{14}$=1106.5199; found=1106.5185

Table 3 summarizes the activity data for compounds E3-6, E4-6, E5-7 and E6-6 in comparison with the comparative semi-synthetic Echinocandin compound C1. The same testing procedures were used as described in Example 1 above.

TABLE 3

| | Minimal Inhibitory Concentration (MIC) µg/ml | | | |
|---|---|---|---|---|
| Example No. | C. albicans | C. parapsilosis | A. fumigatus | Histoplasma capsulatum |
| Comparative C1 | 0.01 | 0.156 | 0.02 | 0.01 |
| E3-6 | 10 | >20 | 20 | 10 |
| E3-7 | >20 | >20 | >20 | >20 |
| E4-6 | 1.25 | >20 | >20 | >20 |
| E5-7 | >20 | >20 | >20 | >20 |
| E6-6 | 0.078 | >20 | >20 | >20 |

Example 7

Example 7 illustrates the formation of a cyclic heptapeptide from the intermediate linear pentapeptide (I-6).

Preparation of N-α-BOC-D-2,3-diaminopropionic acid (E7-1)

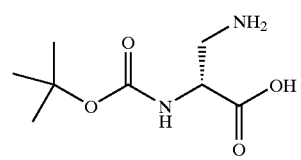

E7-1

To a 1:1 dimethylformamide:water solution (170 ml) of [bis(trifluoroacetoxy)iodo]benzene (12.89 g, 32.29 mmol, 1.5 equiv) was added N-α-BOC-D-asparagine (5 g, 21.53 mmol, 1 equiv). This solution stirred at room temperature for 0.5 h before pyridine (3.4 g, 43.06 mmol, 2 equiv) was added. After 18 h the reaction was concentrated in vacuo and the residue was redissolved in water before being washed with diethyl ether (2×, 50 ml). The aqueous layer was concentrated in vacuo and the crude product was recrystallized from hot acetonitrile to give E7-1 (1.10 g, 25% yield).

Preparation of N-α-BOC-D-2,3-diaminopropionic acid-N-CBZ-glycine Dipeptide (E7-2)

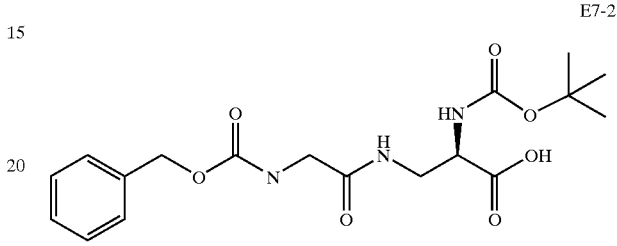

E7-2

An aqueous solution (12 ml) of N-α-BOC-D-2,3-diaminopropionic acid E7-1 (1.114 g, 5.45 mmol, 1 equiv) and NaHCO$_3$ (0.458 g, 5.45 mmol, 1 equiv) was stirred rapidly for 15 minutes until complete salvation. To this was added a 1,2-dimethoxyethane solution (22 ml) of N—CBZ-O—N-hydroxysuccinimide glycine ester. After stirring at room temperature for 18 hours the reaction was concentrated in vacuo. The residue was redissolved in water, acidified to pH 3 with 1N aqueous HCl, and partitioned between ethyl acetate and water. The aqueous layer was washed 3× with additional water before organics were combined, dried over MgSO$_4$, and concentrated. The crude white foam was purified on reverse phase, C-18 column, preparative HPLC (gradient 5:95 AcN/0.01% TFA to 100% AcN elution scheme) to afford 1.46 g (3.69 mmol, 68% yield) of E7-2.

Preparation of N-α-BOC-D-2,3-diaminopropionic acid-N-CBZ-glycine Dipeptide-O-NHS Active Ester (E7-3)

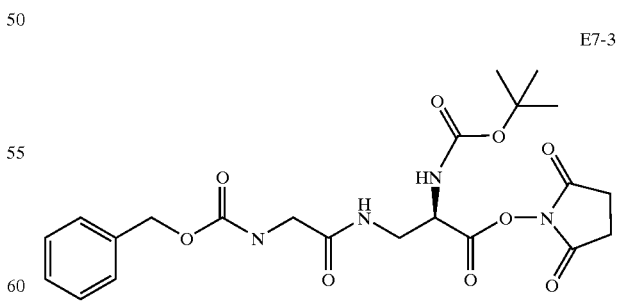

E7-3

To a 1,2-dimethoxyethane solution (40 ml) of E7-2 (1.40 g, 3.54 mmol, 1 equiv) and N-hydroxysuccinimide (0.448 g, 3.89 mmol, 1.1 equiv) cooled to 0° C. was added dicyclohexylcarbodiimide (0.804 g, 3.89 mmol, 1.1 equiv). After stirring for 1 h at 0° C. it was set in the refrigerator for 18 hours. The solution was then filtered and the filtrate was stripped to dryness and placed on high vacuum for 2 hours to give approximately 2 g of product (contained some DCU byproduct) which was used without further purification.

DiBOC Silyl N(α)BOC-D-2,3-diaminopropionic acid-glycine-CBZ heptapeptide (E7-4)

lamine until the solution was basic to pH paper. After stirring for 16 hrs., the solution was extracted with saturated NaHCO$_3$ solution followed by dilute HCl solution and then another portion of saturated NaHCO$_3$ solution. The organic layer was dried over MgSO$_4$ and reduced in vacuo to give 1.194 g of the crude product. Purification by flash chromatography (30% ethyl acetate/hexane) gave 0.674 g (59% yield) of coupled product E7-4. FAB MS=1916.5 (M+1)

Cyclization of E7-4 to BOC Silyl Cycloheptapeptide (E7-5)

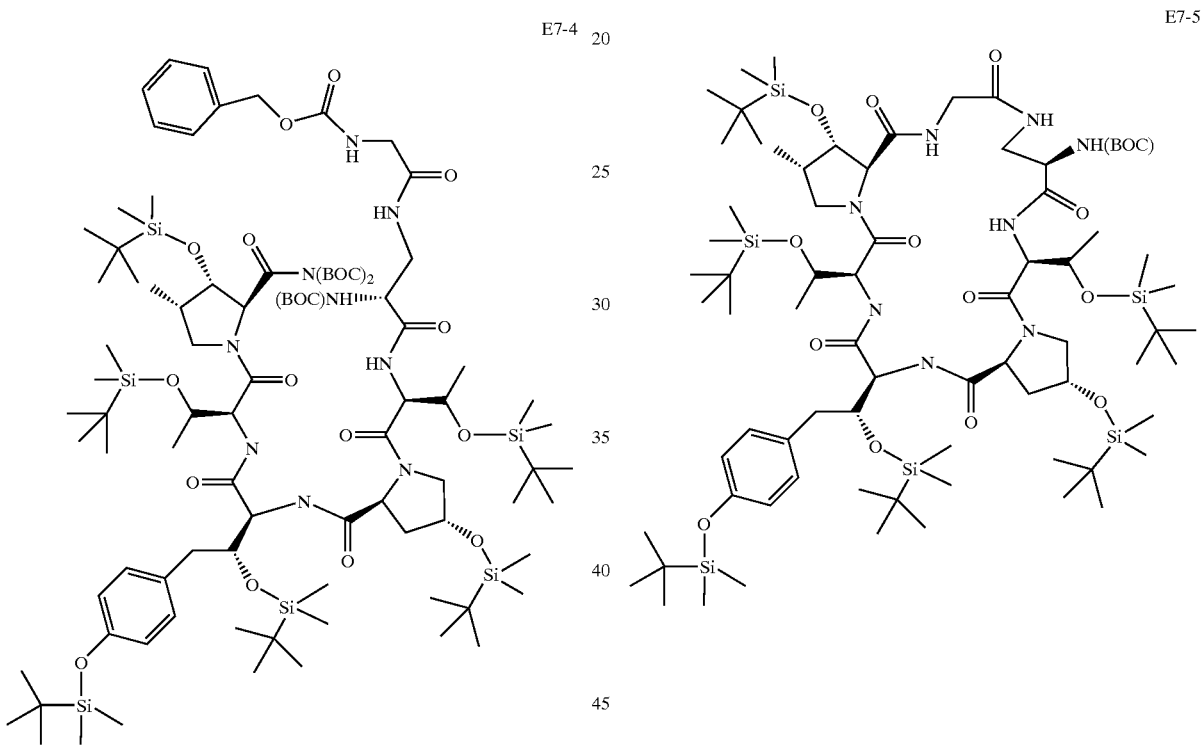

A solution of linear peptide intermediate I-6 (1.0 g, 0.598 mmol) in ethanol (5 ml) was added to a slurry of 10% Pd/C (250 mg) in 5 ml of ethanol followed by 10 ml of glacial acetic acid. The mixture was put under a balloon of H$_2$ and after 1 hr the starting material was gone (TLC 25% ethyl acetate/hexane). The catalyst was removed by filtration through a Celite plug and the solution was carefully reduced (but not to dryness) under high vacuum keeping the temperature under 40° C. The resulting oil was dissolved in 25 ml of ether and a 10 ml tetrahydrofuran solution of dipeptide active ester E7-3 (O-Suc-Nα-BOC-D-2,3-diaminopropionic acid-N-CBZ-glycine) was added followed by excess triethy- An ethanol/acetic acid solution (10 ml of each) of E7-4 (0.665 g, 0.34 mmol) with 10% Pd/C (200 mg) was placed under a balloon of hydrogen. After 1.5 hrs., TLC (30% ethyl acetate/hexane) indicated a complete reaction. The catalyst was removed by filtration through a plug of Celite and the solvent reduced in vacuo (but not to dryness) at 40° C. until the residue was a thick oil. This material was dissolved in ethyl ether (150 ml) and excess triethylamine (~8 ml) was added. After 18 hrs., TLC (30% ethyl acetate/hexane) indicated one major product spot. The solvent was removed in vacuo and the residue was redissolved in ethyl acetate and washed several times with water. The organics were combined and dried over MgSO$_4$ and the solvent removed in vacuo to give 0.800 g of crude product. This was purified over a flash column (silica gel eluted with 30% ethylacetate/hexanes) to provide 293 mg (54% yield) of E7-5 as a white solid. FAB MS=1564.9

Removal of Protecting Groups and Coupling of the Side Chain to Give E7-6

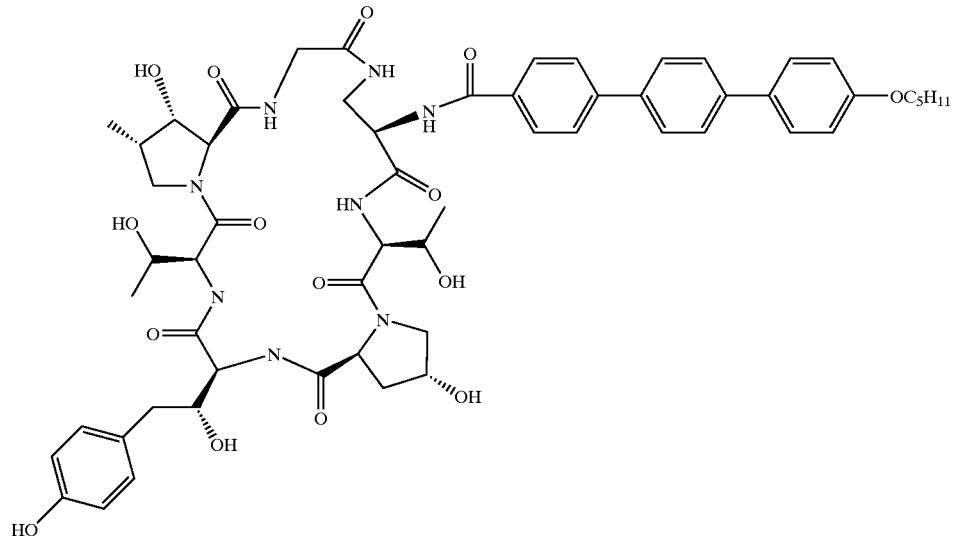

E7-6(a)

Compound E7-5 (288 mg, 0.181 mmol) was dissolved in trifluoroacetic acid (3 ml) and cooled to 0° C. After 0.5 hrs., water was added (0.5 ml) and the mixture was stirred for 0.6 hrs longer. The solvent was removed in vacuo and the residue was dissolved in 1N HCl (2 ml) and tetrahydrofuran (3 ml). This solution was stirred at room temperature for 1.5 hr after which time it was set in the refrigerator overnight. The solvent was removed under high vacuum giving a foam residue which was dissolved in anhydrous dimethylformamide (3 ml). Terphenyl hydroxybenzotriazole active ester (108 mg, 0.276 mmol) and triethylamine (0.11 ml, 0.78 mmol) were added to the solution. After stirring overnight at room temperature the solvents were removed under high vacuum and the crude material (380 mg) was purified by preparative RP-HPLC (C-18 column eluted with a 50% AcN/0.01% TFA aqueous solution). Lyophilization of the pure fractions gave 97 mg (48% yield) of E7-6(a) as a white solid. FAB MS=1121.5 (M) calc. for $C_{58}H_{72}N_8O_{15}$=1121.21

Preparation of E7-6(b)

In a similar manner, N-α-BOC-L-asparagine was converted to E7-6(b).

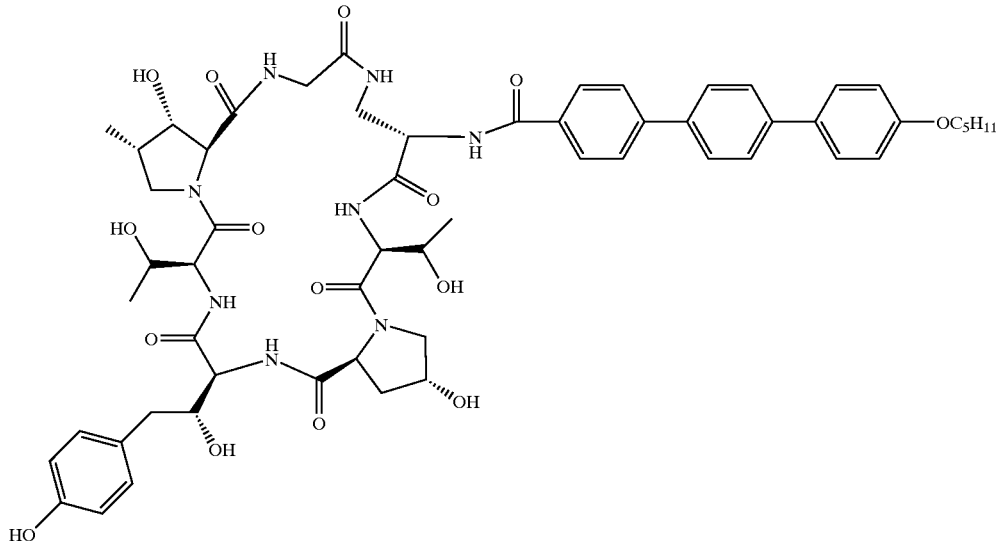

E7-6(b)

The H-NMR data was consistent with the structure E7-6 (b). MS(FAB)=1121 (M+)

Preparation of N-α-CBZ-D-2,3-diaminopropionic acid (E7-7)

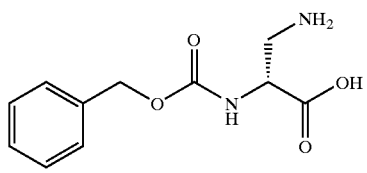

E7-7

Compound E7-7 was prepared in a similar manner to N-α-BOC-diamino propionic acid E7-1. MS FAB (M+1)= 239

Preparation of N-α-CBZ-N-β-BOC-D-2,3-diaminopropionic acid (E7-8)

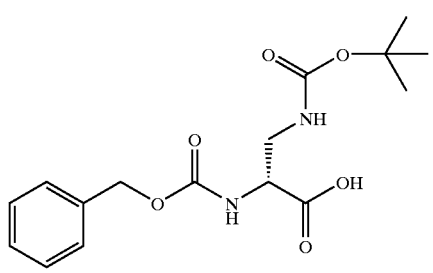

E7-8

To a stirring solution of sodium hydroxide (148 mg, 3.69 mmol, 1.1 equiv) in water (5 ml) was added N-α-CBZ-diamino propionic acid E7-7. The reaction was stirred for 10 minutes before tert-butyl alcohol (4 ml) was added. The reaction was cooled to 0° C. and di-tert-butyl dicarbonate (807 mg, 3.69 mmol, 1.1 equiv) was added slowly over 0.5 h. After stirring overnight at room temperature, the reaction was diluted with water (5 ml) and washed 3× with 10 ml ethyl ether. The organics were then combined and washed several times with saturated aqueous sodium bicarbonate. The aqueous layers were combined, cooled to 0° C., and acidified to pH 3 with aqueous potassium hydrogen sulfate (30 g in 200 ml stock solution). This cloudy solution was then extracted several times with ethyl acetate. The organics were combined, dried over MgSO$_4$, and concentrated in vacuo to give after overnight high vacuum 0.990 g (2.9 mmol, 87% yield) of E7-8. The $^1$H NMR was consistent with structure E7-8. MS FAB (M+1)=339

Preparation of N-β-BOC-D-2,3-diaminopropionic acid (E7-9)

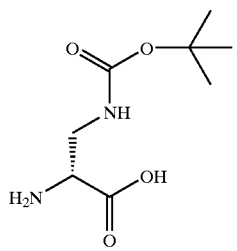

E7-9

To an ethyl alcohol solution (20 ml) of N-α-CBZ-N-β-BOC-D-2,3-diaminopropionic acid E7-8 was added 10% palladium on carbon catalyst (approx. 200 mg). The mixture was placed under an H$_2$ atmosphere and stirred vigorously. Due to gel like formation, the reaction required additional ethyl alcohol (total volume of 75 ml) to facilitate easy stirring. After several hours, the reaction was filtered through a plug of Celite and then concentrated in vacuo to give 259 mg (1.27 mmol, 32% yield) of E7-9.

Preparation of N-β-BOC-D-2,3-diaminopropionic acid-N-CBZ-glycine dipeptide (E7-10)

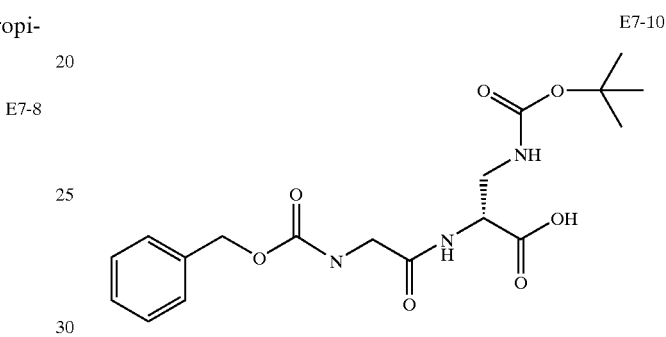

E7-10

Compound E7-10 was prepared in a similar manner as N-α-BOC-D-2,3-diaminopropionic acid-N-CBZ-glycine dipeptide E7-2.

The $^1$H NMR was consistent with the structure E7-10.

Preparation of N-β-BOC-D-2,3-diaminopropionic acid-N-CBZ-glycine dipeptide-O-NHS active ester (E7-11)

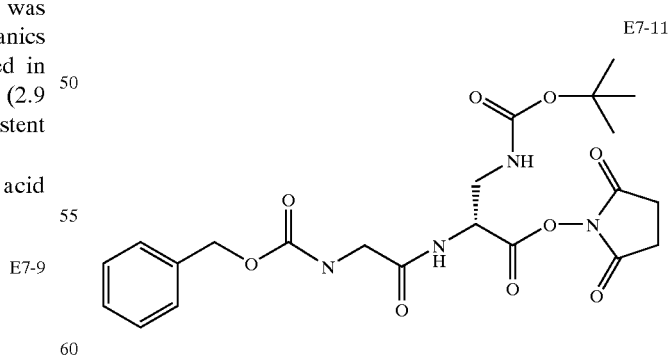

E7-11

Compound E7-11 was prepared in a similar manner as N-α-BOC-D-2,3-diaminopropionic acid-N-CBZ-glycine dipeptide-O-NHS active ester E7-3.

Preparation of DiBOC Silyl N(β)BOC-D-2,3-diaminopropionic acid-glycine-CBZ heptapeptide (E7-12)

Preparation of BOC Silyl Cycloheptapeptide (E7-13)

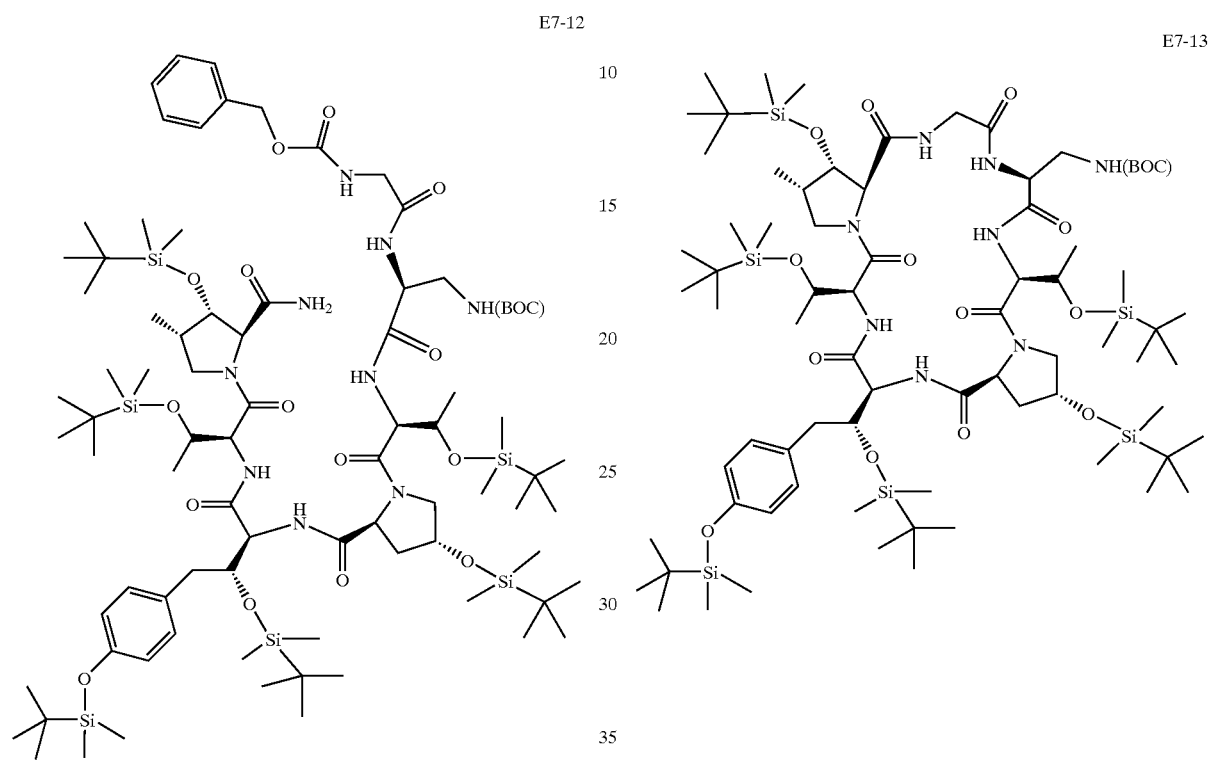

Compound E7-12 was prepared in a similar manner as DiBOC silyl N(α)BOC-D-2,3-diaminopropionic acid-glycine-CBZ heptapeptide E7-4. MS FAB (M+1)=1917

Compound E7-13 was prepared in a similar manner as BOC silyl cycloheptapeptide E7-5.

Preparation of Cycloheptapeptide E7-14(a)

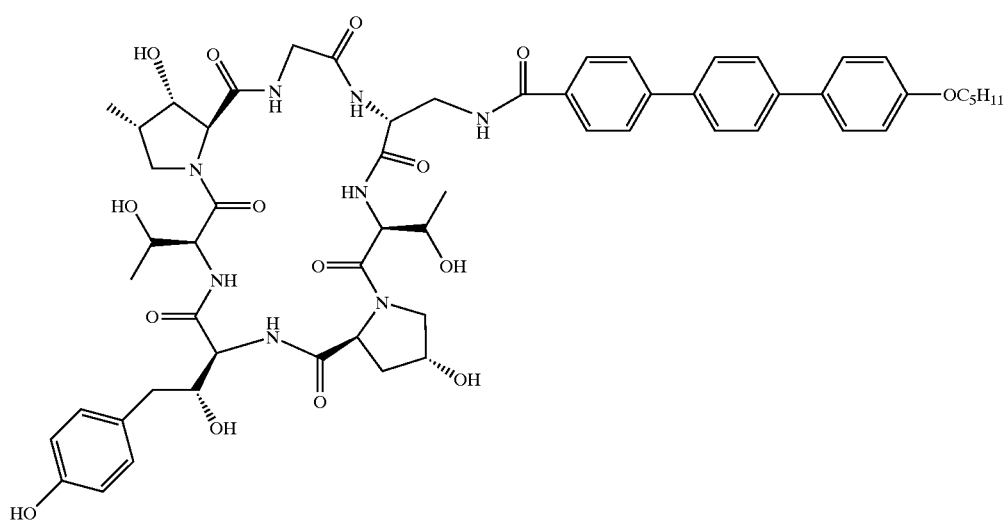

Compound E7-14 was prepared in a similar manner as cycloheptapeptide E7-6. MS FAB (M)=1121.6

Preparation of Cycloheptapeptide E7-14(b)

In a similar manner as E7-14(a), E7-14(b) was prepared from N-α-CBZ-L-2,3-diamino propionic acid.

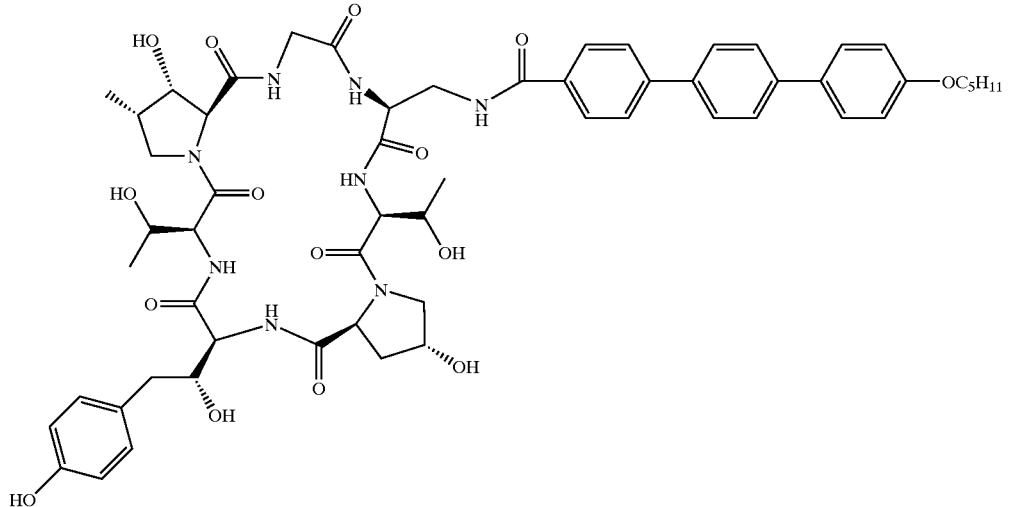

E7-14(b)

The H$^1$-NMR data was consistent with structure E7-14 (b). MS(FAB)=1121 (M+)

Example 8

Preparation of (-L-)-(α)-N-CBZ-(β)-N-trifluoroacetyl 2,3-diaminopropionic acid (E8-1)

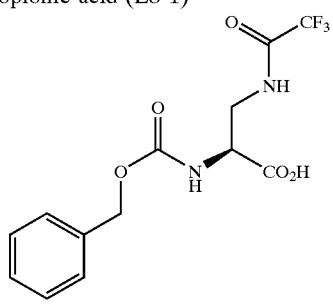

E8-1

The procedure of Curphey et al., *J. Org. Chem.*, 44, 2805, (1979) was utilized as follows. A suspension of (-L-)-(α)-N-CBZ-2,3-diaminopropionic acid (2.0 g, 8.39 mmol) and triethylamine (0.84 g, 8.39 mmol) in methanol (10 ml) at ambient temperature was treated with ethyl trifluoroacetate (1.49 g, 10.49 mmol) and the mixture stirred for 48 hrs. The resulting solution was diluted with methanol (5 ml), cooled to 0° C., and treated with Dowex 50W resin(3.30 g). After stirring for 10 min., the suspension was filtered and the filtrate concentrated in vacuo to produce 2.74 g of a white solid (98% yield) that was used without further purification. H$^1$ NMR data was consistent with the structure E8-1. MS(FD)=334 (M+)

Preparation of the N-hydroxysuccinimide ester (E8-2) from E8-1

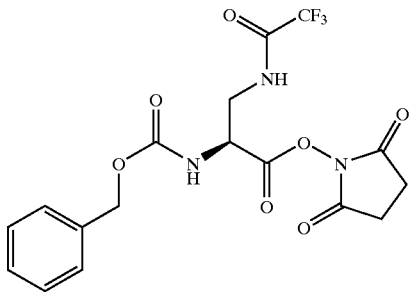

E8-2

To a solution of E8-1 (1.20 g, 3.59 mmol) and N-hydroxysuccinimide (0.45 g, 3.95 mmol) in 1,2-dimethoxyethane (20 ml) at 0° C. was added N,N'-dicyclohexylcarbodiimide (0.81 g, 3.95 mmol). The mixture was stirred at cold bath temperature for 2 hr followed by overnight storage in the refrigerator. Filtration of the suspension and subsequent concentration of the filtrate gave a crude solid product which was recrystallized from ethyl acetate/hexanes to produce 0.78 g of a crystalline solid (50% yield, one crop). The H$^1$ NMR data was consistent with structure E8-2. MS(FD)=431 (M+)

Preparation of Dipeptide (E8-3) from Amino Acid Active Ester E8-2

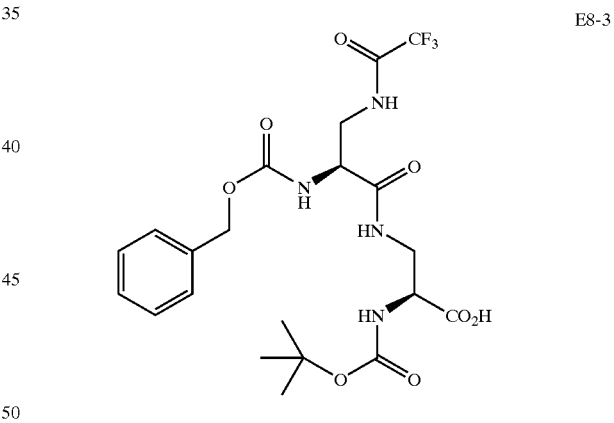

E8-3

(-L-)-(α)-N-BOC-2,3-diaminopropionic acid (0.52 g, 2.55 mmol) was dissolved in aqueous sodium bicarbonate solution (prepared from dissolving 0.22 g, 2.55 mmol of sodium bicarbonate in 10 ml of water). This solution was added to a solution of active ester E8-2 (1.1 g, 2.55 mmol) in 1,2-dimethoxyethane (23 ml) and the mixture stirred for 24 hrs. After concentration in vacuo to remove 1,2-dimethoxyethane, the residual suspension was adjusted to pH 5 with 1N aqueous citric acid, then extracted with ethyl acetate (2×). The combined organic extracts were washed successively with water and brine, dried over MgSO$_4$ and reduced in vacuo to give 1.4 g of a crude foam. Trituration with methylene chloride gave 1.05 g of a flocculent solid (75% yield). Additional product in mother liquor was not recovered.

H$^1$ NMR data was consistent with structure E8-3. MS(negative ion electrospray)=519 (M−H)

Preparation of Dipeptide Active Ester (E8-4) from Dipeptide E8-3

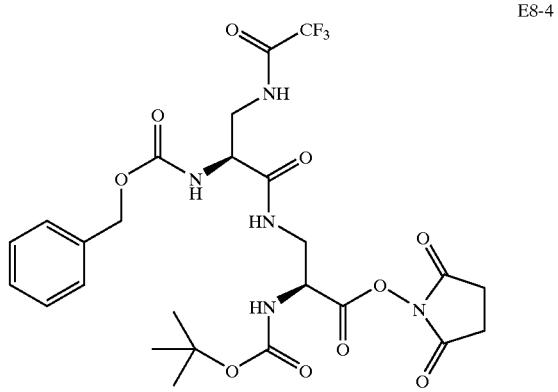

To a solution of E8-3 (0.65 g, 1.24 mmol) and N-hydroxysuccinimide (0.16 g, 1.37 mmol) in tetrahydrofuran (5 ml) at 0° C. was added N,N'-dicyclohexylcarbodiimide (0.28 g, 1.37 mmol). The mixture was stirred at cold bath temperature for 2 hrs followed by overnight storage in the refrigerator. Filtration of the suspension and subsequent concentration of the filtrate gave 0.70 g of a crude foam (89% yield). $H^1$ NMR data was consistent with structure E8-4. MS(FD)=631 (M+)

Preparation of DiBOC silyl (-L-)-(α)-N-BOC-2,3-diaminopropionic acid-(-L-)-(α)-N-CBZ-(β)-N-trifluoroacetyl 2,3-diaminopropionic acid linear heptapeptide (E8-5)

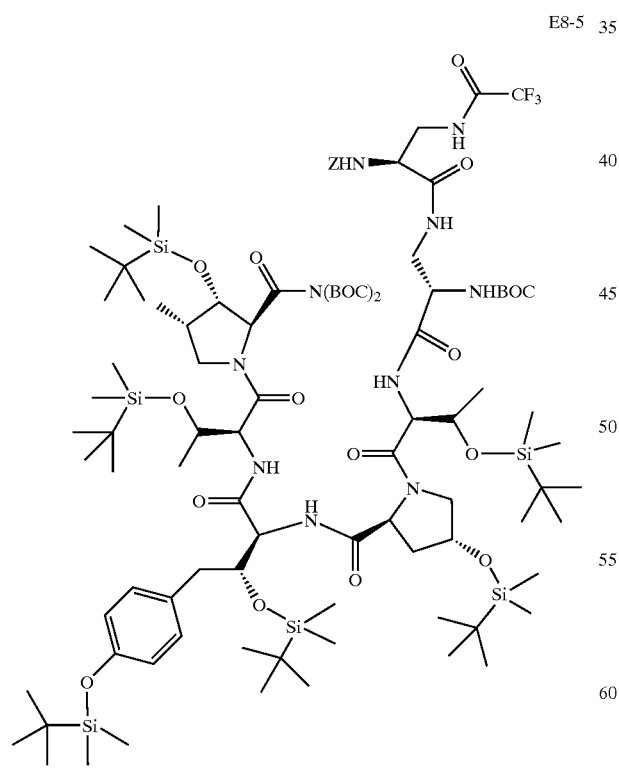

A solution of linear pentapeptide intermediate I-6 (2.0 g, 1.19 mmol) in ethyl acetate (10 ml) was added to a slurry of 10% Pd/C (400 mg) in ethyl acetate (15 ml) followed by 20 ml of glacial acetic acid. The mixture was put under a balloon of $H_2$ and after 1 hr the starting material was gone. The catalyst was removed by filtration and the solution was carefully reduced under high vacuum keeping the temperature under 40° C. The resulting oil was dissolved in THF (15 ml) and the dipeptide active ester, N-(-L-)-(α)-CBZ-N-(β)-trifluoroacetyl 2,3-diaminopropionic acid-N-(L)-(α)-BOC 2,3-diaminopropionic acid-Osu E8-4, was added followed by excess triethylamine until the solution was basic to pH paper. After stirring for 18 hrs., the solution was reduced in vacuo and the residue partitioned between ethyl ether and water. The ether layer was washed with saturated $NaHCO_3$ solution, followed by successive washings with water, 1N aqueous citric acid, water, saturated $NaHCO_3$ and brine. The organic layer was dried over $MgSO_4$ and reduced in vacuo to give 2.36 g of the crude product. Purification by silica flash chromatography (25% ethyl acetate/hexane) gave 1.22 g of coupled product E8-5 as a foam (56% yield). $H^1$ NMR data was consistent with structure E8-5. MS(FAB)=2041.5 (M+)

Cyclization of E8-5 to BOC Silyl Cycloheptapeptide (E8-6)

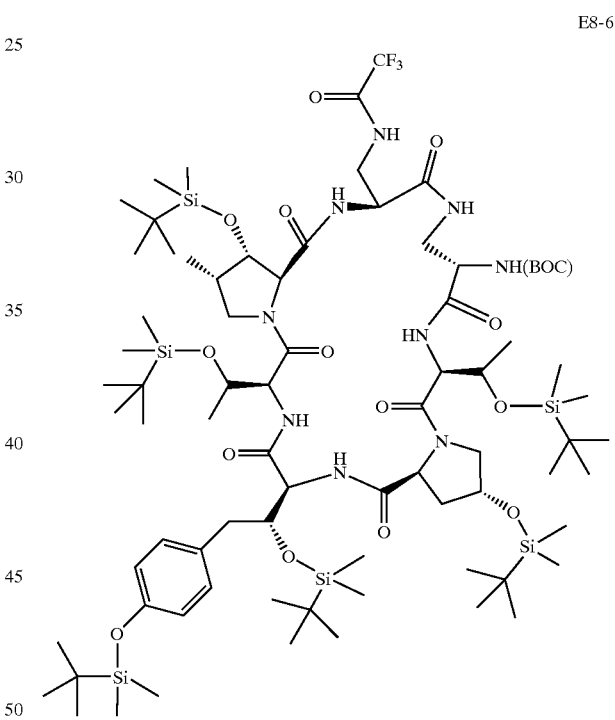

An ethyl acetate/acetic acid solution (20 ml each) of E8-5 (1.20 g, 0.58 mmol) with 10% Pd/C (290 mg) was placed under a balloon of hydrogen. After 1.5 hrs., TLC indicated deprotection was complete. The catalyst was removed by filtration and the filtrate concentrated in vacuo to a thick slurry. This material was dissolved in ethyl ether(120 ml) and excess triethylamine was added until the solution was basic to pH paper(~5 ml). After 36 hrs., TLC indicated one major product. The solution was washed successively with water, 1N aqueous citric acid, water, and brine. The organic layer was dried over $MgSO_4$ and reduced in vacuo to give 1.14 g of crude product. Purification by silica flash chromatography (25% ethyl acetate/hexane) gave 0.69 g of E8-6 as a foam (70% yield). $H^1$ NMR data was consistent with structure E8-6.

MS(FAB)=1690.0 (M+H)

Removal of Protecting Groups and Coupling of the Side Chain to Generate E8-7

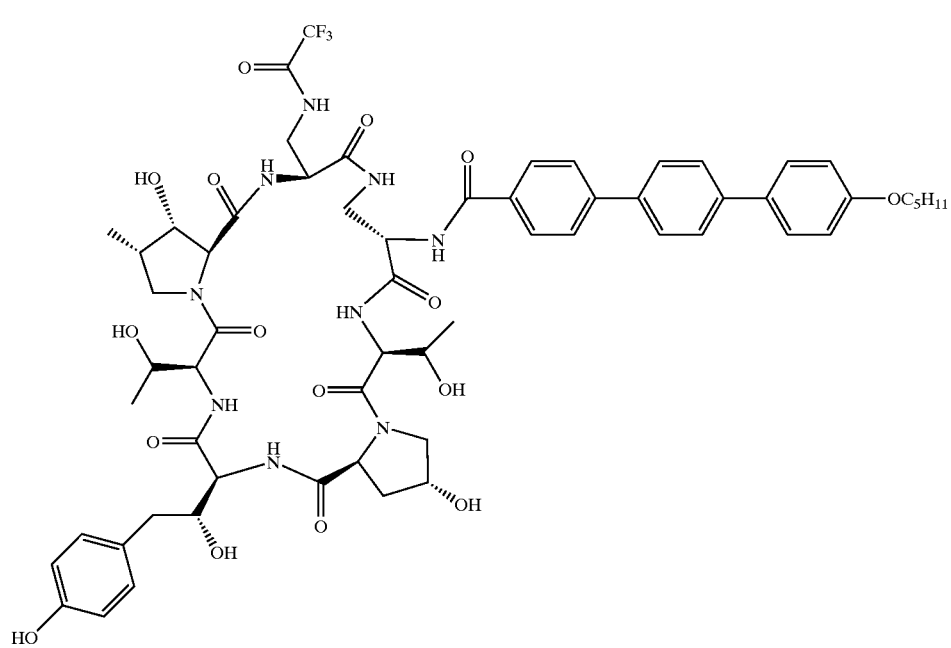

E8-7

A solution of E8-6 (0.69 g, 0.40 mmol) in trifluoroacetic acid (23 ml) at 0° C. was stirred for 0.5 hr after which time water (2 ml) was added and the stirring continued for an additional 0.75 hr at 0° C. The solvent was removed in vacuo and the residue was dissolved in tetrahydrofuran (9 ml) and treated with 1N HCl (4 ml). This solution was stirred at ambient temperature for 1.25 hr and then refrigerated for 18 hr. HPLC showed one major product peak. Concentration in vacuo produced a residual foam which after dissolution in dimethylformamide (12 ml) was treated with the terphenyl hydroxybenzotriazole active ester (0.25 g, 0.52 mmol) and triethylamine (0.28 ml, 2.0 mmol). After stirring at ambient temperature for 17 hrs., the solvent was removed under high vacuum and the crude residue purified by preparative RP-HPLC (linear gradient 60%–100% AcN/0.1% TFA elution scheme) to produce 0.37 g of a white solid (75% yield). $H^1$ NMR data was consistent with structure E8-7. MS(FAB)=1246.7 (M+)

Final Deprotection of E8-7 to Generate E8-8

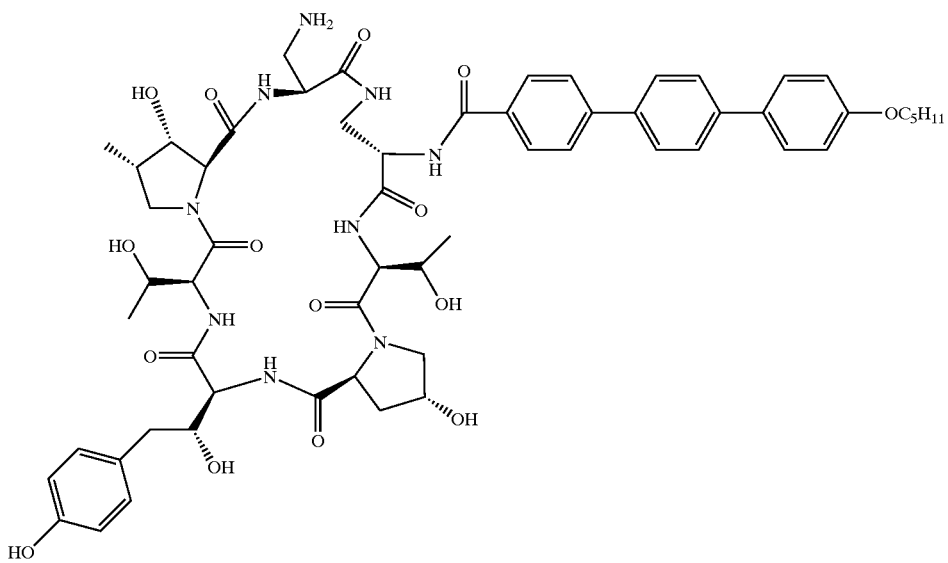

E8-8

To a solution of E8-7 (250 mg, 0.20 mmol) in methanol (12 ml) was added a solution of potassium carbonate (138 mg, 1.0 mmol) in water (6 ml), and the resulting mixture stirred at ambient temperature for 20 hrs. Solvent removal in vacuo followed by purification via preparative RP-HPLC (linear gradient 60–100% AcN/0.1% TFA elution scheme)

gave 218 mg of a white solid (94% yield). $H^1$ NMR data was consistent with structure E8-8. MS(FAB)=1150.6 (M+)
Reductive Alkylation of E8-8 to Generate E8-9 ent 40–100% AcN/0.1% TFA elution scheme) to yield 19 mg of a white solid (45% yield). $H^1$ NMR data was consistent with structure E8-9. MS(FAB)=1247.6 (M+)

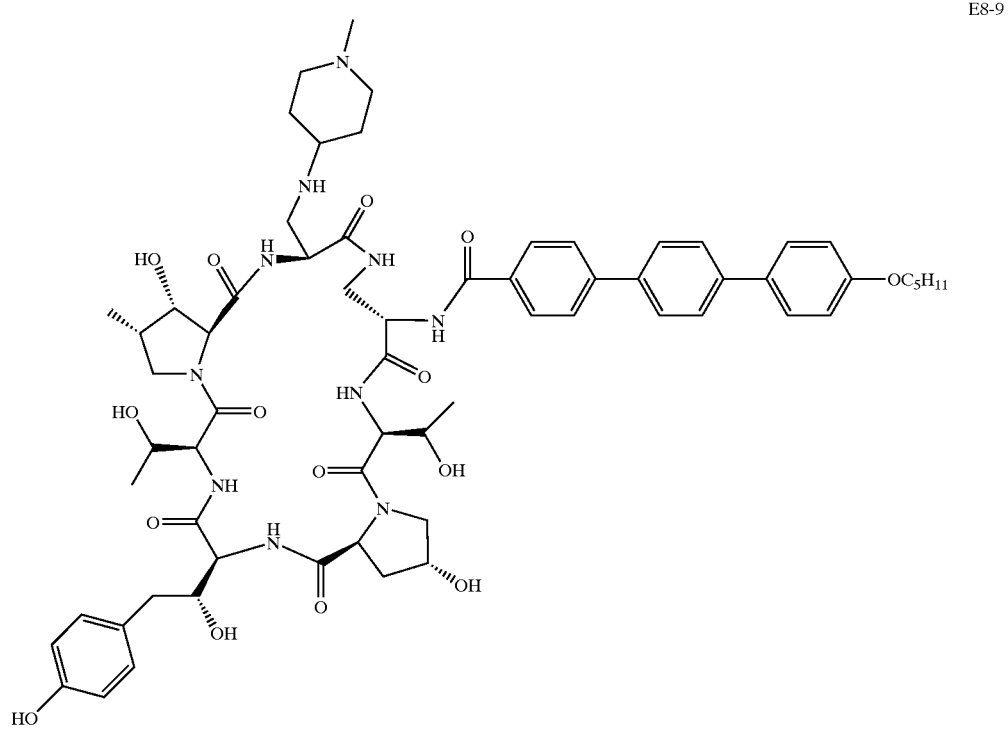

E8-9

To a solution of E8-8 (40 mg, 0.0347 mmol) in methanol (2 ml) at ambient temperature was added 1-methyl-4-piperidone (7.85 mg, 0.0694 mmol) and glacial acetic acid (2 µl, 0.0347 mmol). The solution was treated with sodium cyanoborohydride (3.27 mg, 0.0520 mmol) and the mixture stirred for 16 hrs. After concentration in vacuo, the crude product was purified via preparative RP-HPLC (step gradi- Table 4 summarizes the activity data for compounds E7-6(a), E7-6(b), E7-14(a), E7-14(b), E8-8 and E8-9 in comparison with the comparative semi-synthetic Echinocandin compound C1 and Amphotericin B. The same testing procedures were used as described in Example 1 above.

TABLE 4

| Example No. | Minimal Inhibitory Concentration (MIC) µg/ml ||||| 
|---|---|---|---|---|---|
| | Candida albicans | Candida parapsilosis | Aspergillus fumigatus | Cryptococcus neoformans | Histoplasma capsulatum |
| Comparative C1 | 0.01 | 0.156 | 0.02 | >20 | 0.01 |
| Ampho B | 0.078 | 0.038 | 0.312 | 0.039 | 0.039 |
| E7-6(a) (22 membered ring) | >20 | >20 | >20 | >20 | >20 |
| E7-6(b) (22 membered ring) | 0.312 | >20 | 5.0 | >20 | 1.25 |
| E7-14(a) (21 membered ring) | 0.312 | >20 | >20 | >20 | 0.312 |
| E7-14(b) (21 membered ring) | 0.156 | >20 | >20 | >20 | 0.078 |
| E8-8 (22 membered ring) | 0.078 | 0.625 | 5.0 | >20 | 0.312 |
| E8-9 (22 membered ring) | 0.156 | 5.0 | 5.0 | >20 | 0.625 |

We claim:

1. A process for modifying a cyclic peptide ring nucleus comprising the steps of:
   (i) providing a cyclic peptide compound comprising a peptide unit having a γ-hydroxyl group;
   (ii) opening the ring of said cyclic peptide compound to provide a first linear peptide wherein said peptide unit having a γ-hydroxyl group is the N-terminus peptide unit of said first linear peptide;
   (iii) cleaving-off said peptide unit having a γ-hydroxyl group to provide a second linear peptide;
   (iv) attaching at least one amino acid, dipeptide unit or synthetic unit to said second linear peptide to produce a third linear peptide;
   (v) cyclizing said third linear peptide to produce a modified cyclic peptide compound having a modified ring nucleus;
   wherein said modified cyclic peptide compound is represented by formula I or II:

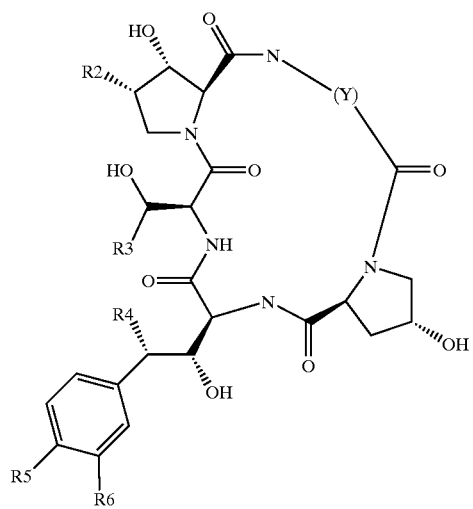

I

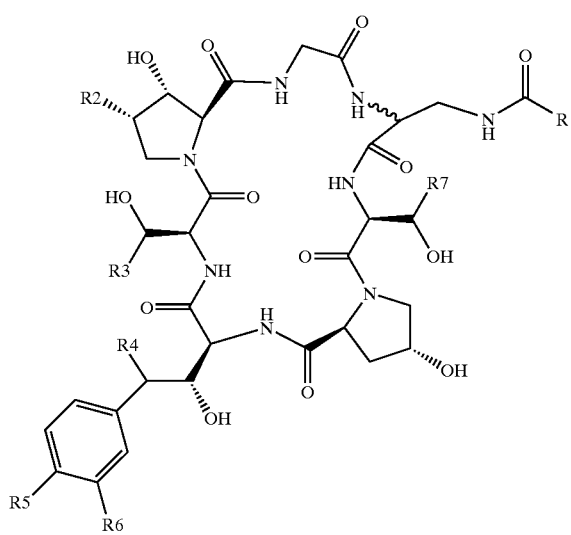

II wherein
R is an alkyl group, an alkenyl group, an alkynyl group, an aryl group, or heteroaryl group;
R2 is —H or —CH$_3$;
R3 is —H, —CH$_3$, —CH$_2$CONH$_2$ or —CH$_2$CH$_2$NH$_2$;
R4 is —H or —OH;
R5 is —OH, —OPO$_3$H$_2$, or —OSO$_3$H;
R6 is —H or —OSO$_3$H;
R7 is —CH$_3$ or —H;
(Y) is represented by the following formula

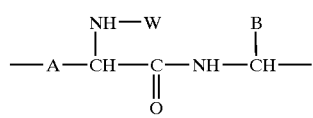

wherein
A is —(CH$_2$)$_a$— where a=1–4
—CHR'—CHR"—(CH$_2$)$_b$—, where R' and R" are independently —H, —OH, C$_6$H$_5$O—, —SH, —NH$_2$, C$_n$H$_{2n+1}$NH—, C$_n$H$_{2n+1}$O—, C$_n$H$_{2n+1}$S— or C$_n$H$_{2n+1}$, where n=1–4 and b=0–1,
—(CH$_2$)$_c$—C(O)NH(CH$_2$)$_d$—, where c=1–2 and d=1–2,
—N=CH—(CH$_2$)$_e$— where e=0–2,
—NR'"(CH$_2$)$_f$—, where R'" is —H, —C(O)CH$_2$NH$_2$, —C(O)CH(NH$_2$)CH$_2$NH$_2$ or C$_n$H$_{2n+1}$ where n=1–4 and f=1–3,
—(CH$_2$)$_g$—SO$_2$—(CH$_2$)$_h$— where g=1–2 and h=1–2,

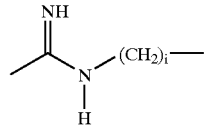

where i=1 or 2, or

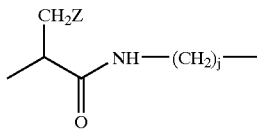

where j is 1 or 2 and Z is an amino group, alkylamino group, or piperidyl amino group; and
B is a substituted or unsubstituted C1 to C6 alkyl group;
W is a hydrogen or C(O)R where R is as defined above; and pharmaceutically acceptable salts, esters or hydrates thereof.

2. The process of claim 1 wherein said cyclic peptide compound is an Echinocandin-type compound.

3. The process of claim 2 wherein said modified cyclic peptide compound is a 19-, 20-, 21-, or 22-membered ring compound.

4. The process of claim 2 wherein said Echinocandin-type compound is a semi-synthetic derivative.

5. The process of claim 2 wherein said Echinocandin-type compound is a natural product.

6. The process of claim 5 wherein said natural product is Echinocandin B, Echinocandin C, Aculeacin Nγ, Mulundocandin, Sporiofungin A, WF11899A, Cilofungin or Pneumocandin B$_0$.

7. The process of claim 1 wherein R is an aryl or heteroaryl group.

8. The process of claim 7 wherein R is an aryl group.

9. The process of claim 8 wherein the aryl group is a chain of aromatic moieties.

10. The process of claim 9 wherein R is a terphenyl group represented by the structure

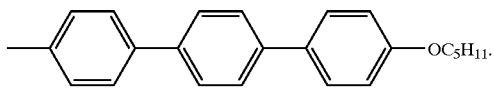

11. The process of claim 1 wherein said amino acid, said dipeptide unit or said synthetic unit of step (iv) comprises a protected amino group.

12. The process of claim 11 further comprising (vi) deprotecting said protected amino group to provide a deprotected amino group;

(vii) acylating said deprotected amino group.

13. The process of claim 11 or claim 12 further comprising cleaving another peptide unit from said second linear peptide in step (iii) before attaching said at least one amino acid, dipeptide unit or synthetic unit in step (iv).

14. The process of claim 1 wherein step (iii) is performed by adding trifluoroacetic acid or hydrochloric acid to said first linear peptide in an organic solvent.

15. The process of claim 14 wherein said organic solvent is selected from the group consisting of methylene chloride, toluene and dioxane.

16. The process of claim 11 or 12 wherein a second amino acid, dipeptide or synthetic unit is attached to said third linear peptide in step (iv) prior to cyclizing in step (v).

17. The process of claim 13 wherein a second amino acid, dipeptide or synthetic unit is attached to said third linear peptide in step (iv) prior to cyclizing in step (v).

18. The process of claim 1 wherein said cyclic peptide compound is a cyclic hexapeptide.

* * * * *